(12) United States Patent
Solinsky

(10) Patent No.: US 9,470,763 B2
(45) Date of Patent: Oct. 18, 2016

(54) SYSTEMS AND METHODS FOR SENSING BALANCED-ACTION FOR IMPROVING MAMMAL WORK-TRACK EFFICIENCY

(71) Applicant: James C. Solinsky, Fleetwood, NC (US)

(72) Inventor: James C. Solinsky, Fleetwood, NC (US)

( * ) Notice: Subject to any disclaimer, the term of this patent is extended or adjusted under 35 U.S.C. 154(b) by 499 days.

(21) Appl. No.: 14/073,826

(22) Filed: Nov. 6, 2013

(65) Prior Publication Data

US 2015/0100251 A1     Apr. 9, 2015

Related U.S. Application Data

(63) Continuation-in-part of application No. 13/570,152, filed on Aug. 8, 2012, which is a continuation-in-part of application No. 12/805,496, filed on Aug. 3, 2010, now Pat. No. 8,626,472.

(60) Provisional application No. 61/723,132, filed on Nov. 6, 2012, provisional application No. 61/344,260, filed on Jun. 21, 2010, provisional application No. 61/344,026, filed on May 10, 2010, provisional application No. 61/282,527, filed on Feb. 25, 2010, provisional application No. 61/521,278, filed on Aug. 8, 2011, provisional application No. 61/556,365, filed on Nov. 7, 2011, provisional application No. 61/617,424, filed on Mar. 29, 2012.

(51) Int. Cl.
| | |
|---|---|
| G06F 19/00 | (2011.01) |
| G01R 33/06 | (2006.01) |
| G01C 21/00 | (2006.01) |
| G01C 21/16 | (2006.01) |
| G01L 9/00 | (2006.01) |
| G01L 19/00 | (2006.01) |

(52) U.S. Cl.
CPC .............. *G01R 33/06* (2013.01); *G01C 21/005* (2013.01); *G01C 21/16* (2013.01); *G01L 9/0073* (2013.01); *G01L 19/0092* (2013.01)

(58) Field of Classification Search
CPC ................ E21B 43/2401; G01N 2035/00326; G01N 2035/00495; A61B 5/681
USPC .................................. 702/160, 155, 182–188
See application file for complete search history.

(56) References Cited

U.S. PATENT DOCUMENTS

| | | |
|---|---|---|
| 6,305,221 B1 | 10/2001 | Hutchings |
| 2007/0032748 A1 | 2/2007 | McNeil et al. |
| 2007/0250286 A1 | 10/2007 | Duncan et al. |

(Continued)

OTHER PUBLICATIONS

International Preliminary Report on Patentability mailed Feb. 20, 2014 in corresponding International Application No. PCT/US2012/050041.

(Continued)

*Primary Examiner* — Edward Raymond
(74) *Attorney, Agent, or Firm* — Nixon & Vanderhye, P.C.

(57) ABSTRACT

An example system includes one or more sleeves, each configured for attachment to a leg and comprising a pressure sensor, an accelerometer and a magnetometer. A processor processes sensor signals from the pressure sensor, the accelerometer and the magnetometer to estimate action (A) and work (W) using event detections of peak stance and valley swing events associated with leg movement, for optimizing energy efficiency for maintaining a balance of the body leaning forward in a gravity pull-down force, with the periodic upward force of the sequential foot-thrusts with the toes.

5 Claims, 44 Drawing Sheets

(56) References Cited

U.S. PATENT DOCUMENTS

2007/0273504 A1* 11/2007 Tran .................... A61B 5/0022
                                                         340/539.12
2009/0198155 A1    8/2009  Bonnet
2010/0070193 A1    3/2010  Solinsky
2011/0054358 A1    3/2011  Kim et al.
2014/0278229 A1*   9/2014  Hong .................. A61B 5/7455
                                                         702/160

OTHER PUBLICATIONS

Notice of Acceptance dated May 24, 2016 in counterpart Australian Patent Application No. 2011219024.

Final Office Action dated Jun. 2, 2016 in parent U.S Appl. No. 13/570,152.

* cited by examiner

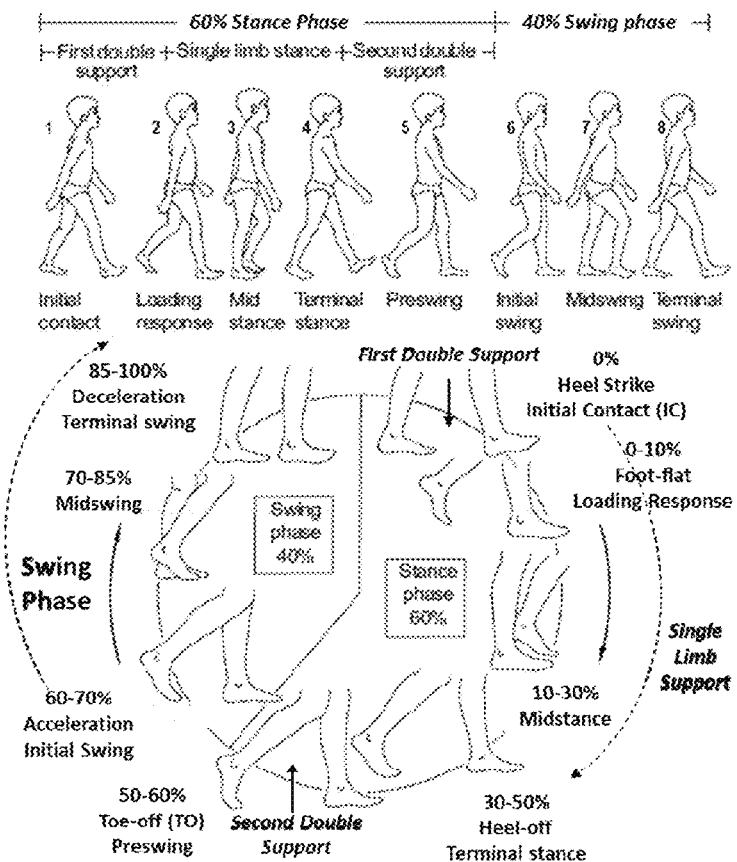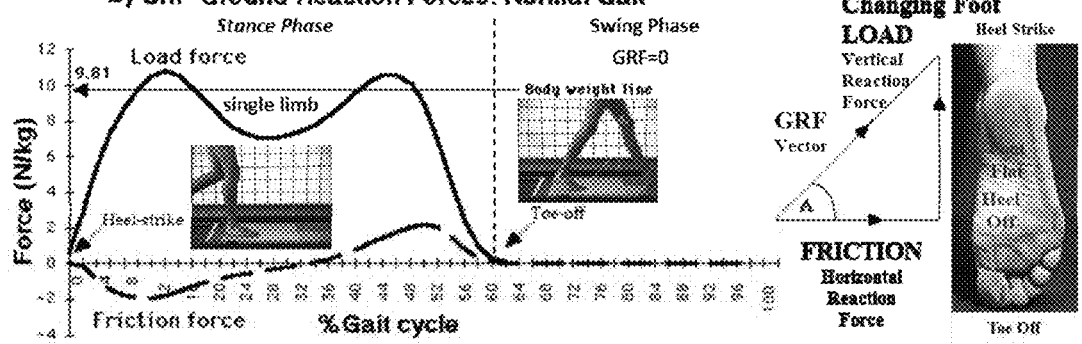
FIG. 1

FIG. 21b-1
10-30 msec
50 msec
333 msec
FIG. 21b-2
0.5 sec
2 sec
5 sec
FIG. 21b-3
2 sec
32 sec
17 sec
FIG. 21b-4
0.3 min
2 min
1.1 min
FIG. 21b-5
1 min
10 min
5 min
Solinsky Sleeve Data:
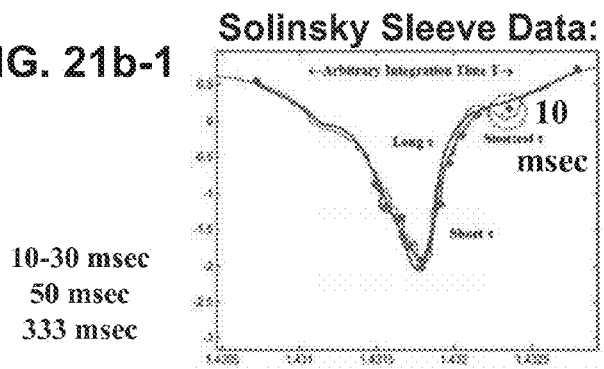
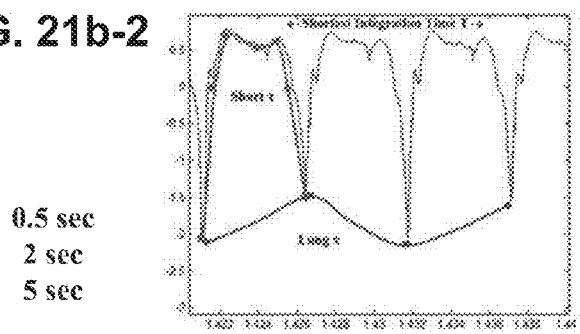
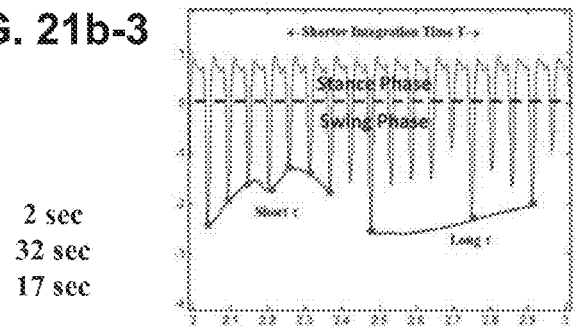
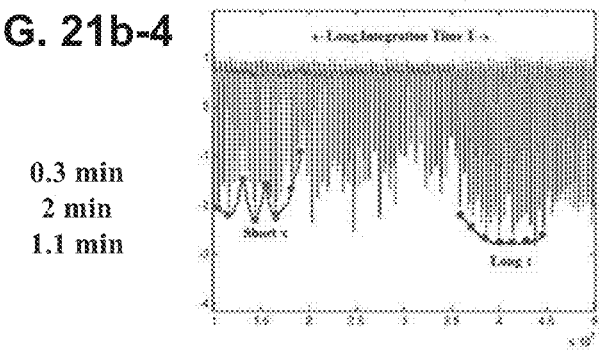
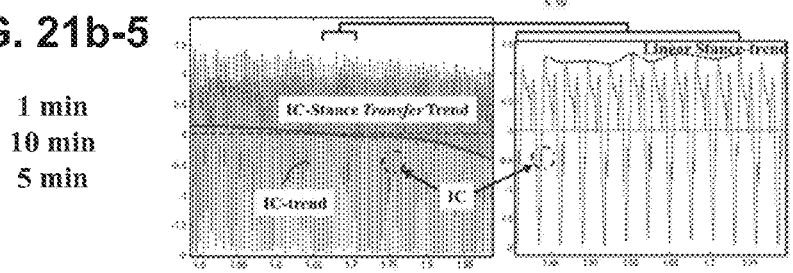
5-Time Scales
(0.01 sec to months)
Pressure Data
single/multi Event ($\tau$)
Integration (T)
Nonlinear Stance
Data

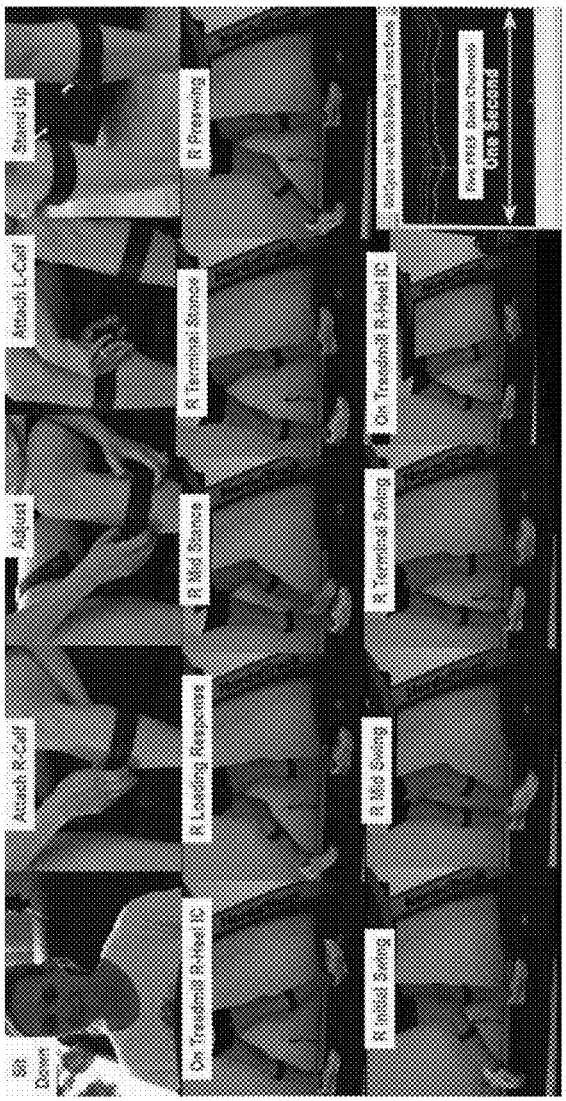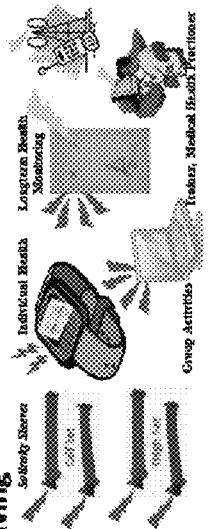
FIG. 24

Table 1 | Proprioceptive reflexes suggested to be involved in locomotion

| Appropriate stimulus | Receptor pathway | Afferent connection | Reflex | Suggested function |
|---|---|---|---|---|
| Dynamic muscle stretch (small amplitude) | Muscle spindles (nuclear bag) | Group I | Monosynaptic stretch reflex | Compensation for ground irregularities, running/ hopping (?) |
| Muscle stretch (large amplitude, static) | Muscle spindles (nuclear chain) | Group I, II | Polysynaptic spinal reflex | Compensation for perturbations of gait |
| Change in body's centre of mass | Golgi tendon organs | Group Ib | Polysynaptic, convergence spinal interneurons | Control of body's centre of mass |
| Joint-movement position | Muscles around joint, mechano-sensors of joint capsule | Group I, II | Polysynaptic, convergence spinal interneurons | Influence on locomotor pattern (hip); local compensation (other leg joints) |
| Skin deformation | Mechanoreceptors of skin | Group II, III | Polysynaptic, convergence spinal interneurons | Adaptation to actual ground conditions |
| Noxious stimulus, pressure | Free endings; Pacini corpuscles | Group III, IV | Spinal interneurons (CPG); flexor reflex | Withdrawal reflex |

CPG, central pattern generator.

Proprioception, Muscle Stretch, CM and Joint Dynamics Measured in PST

FIG. 32

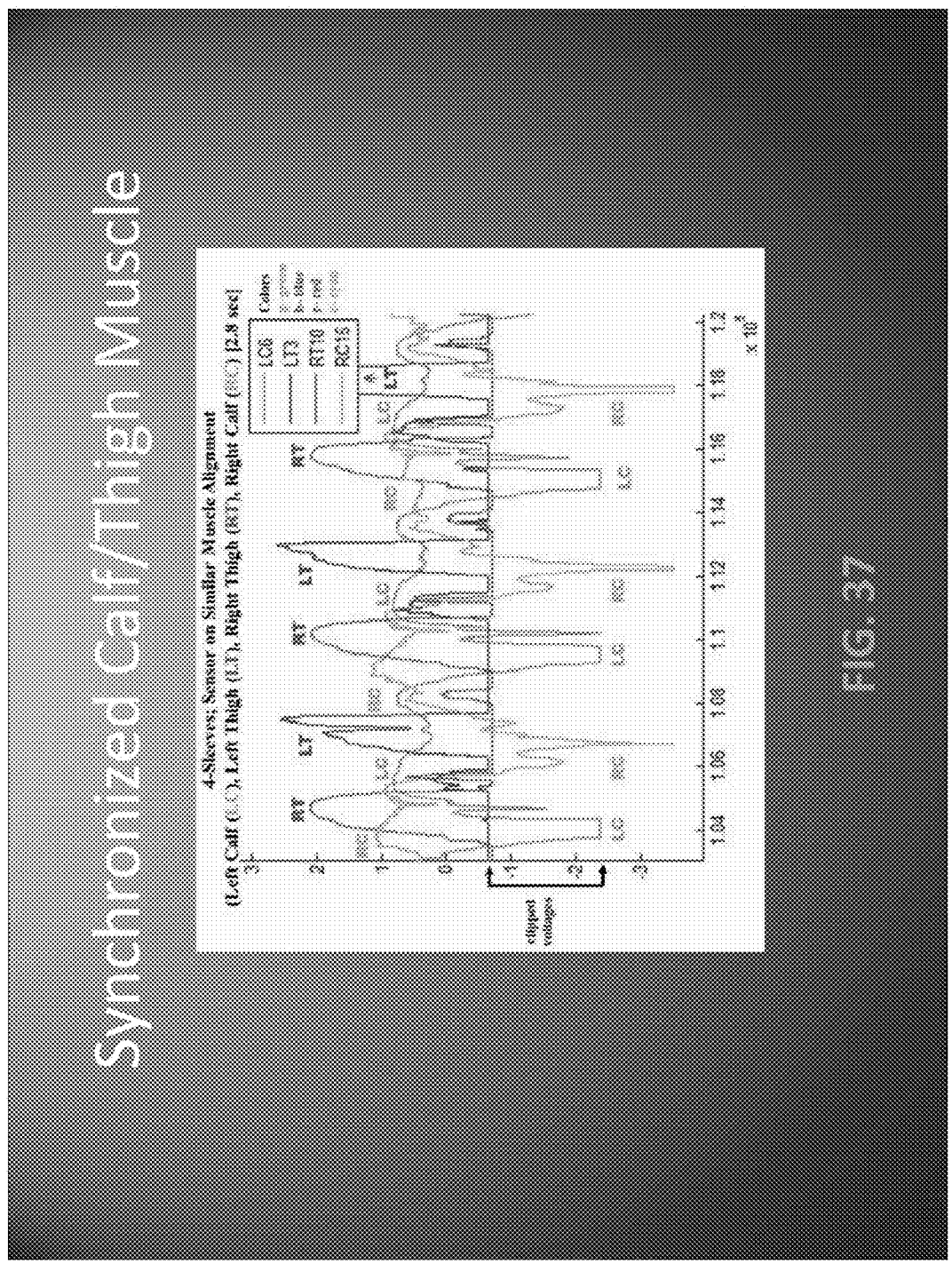

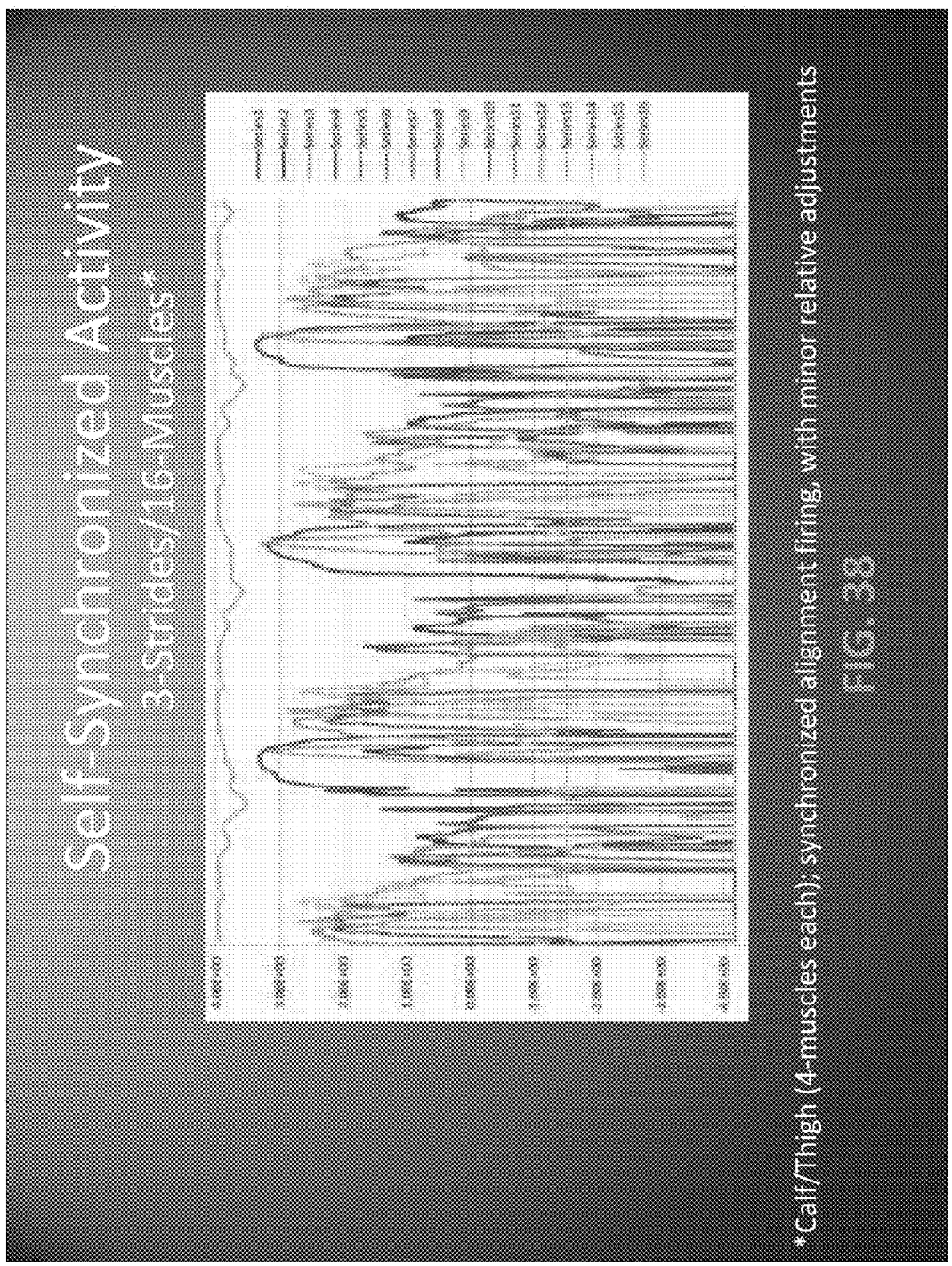

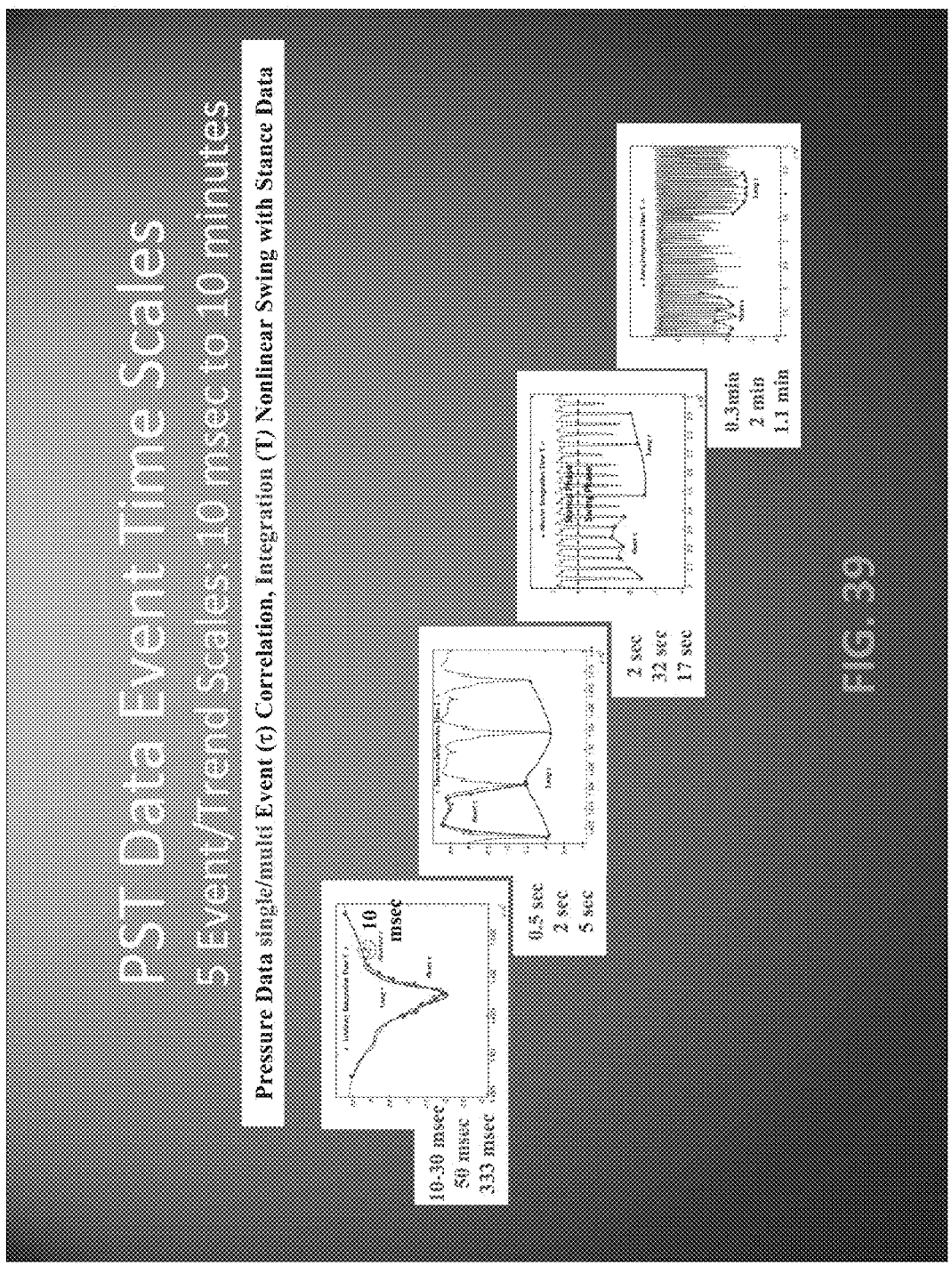

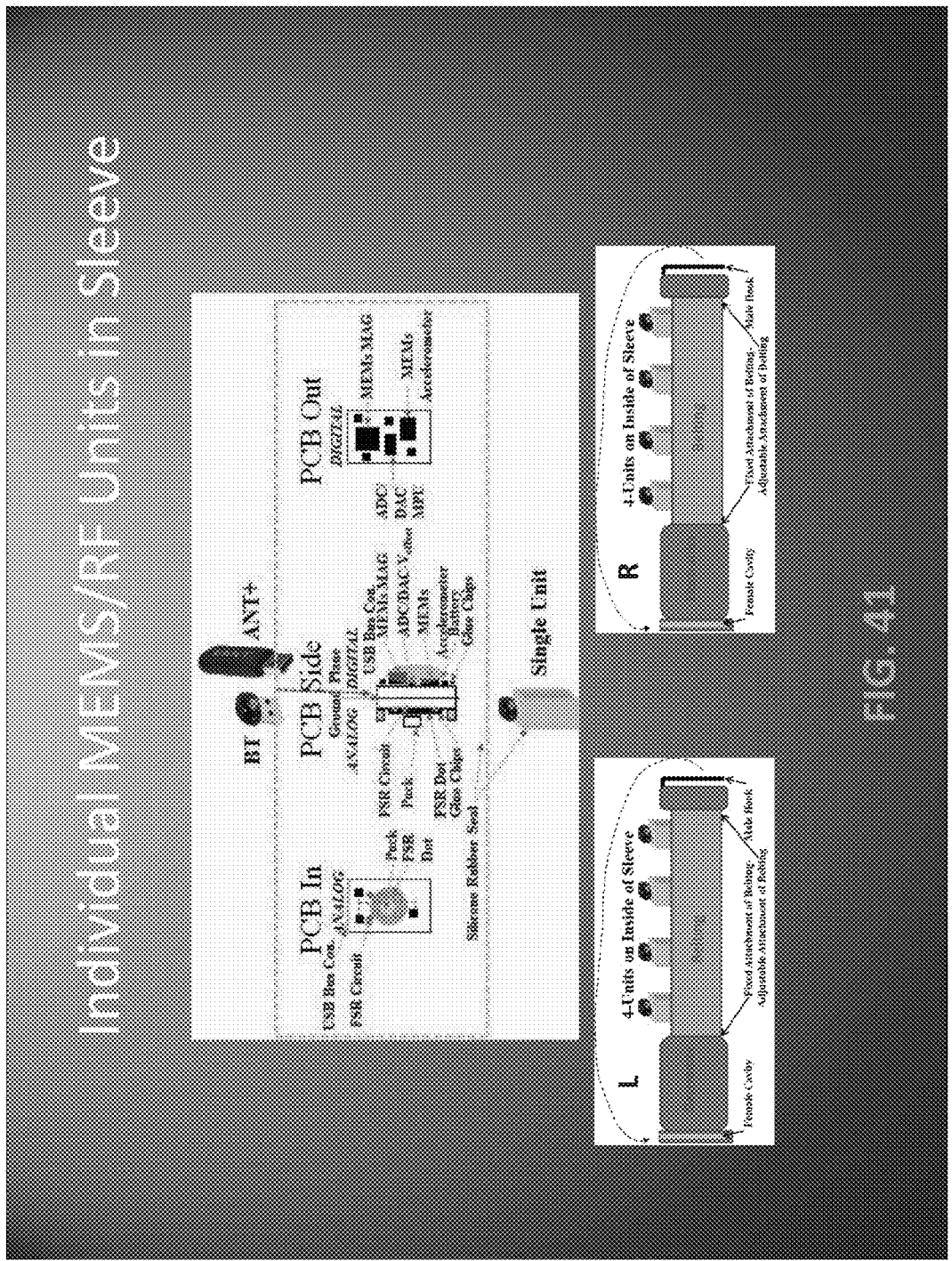

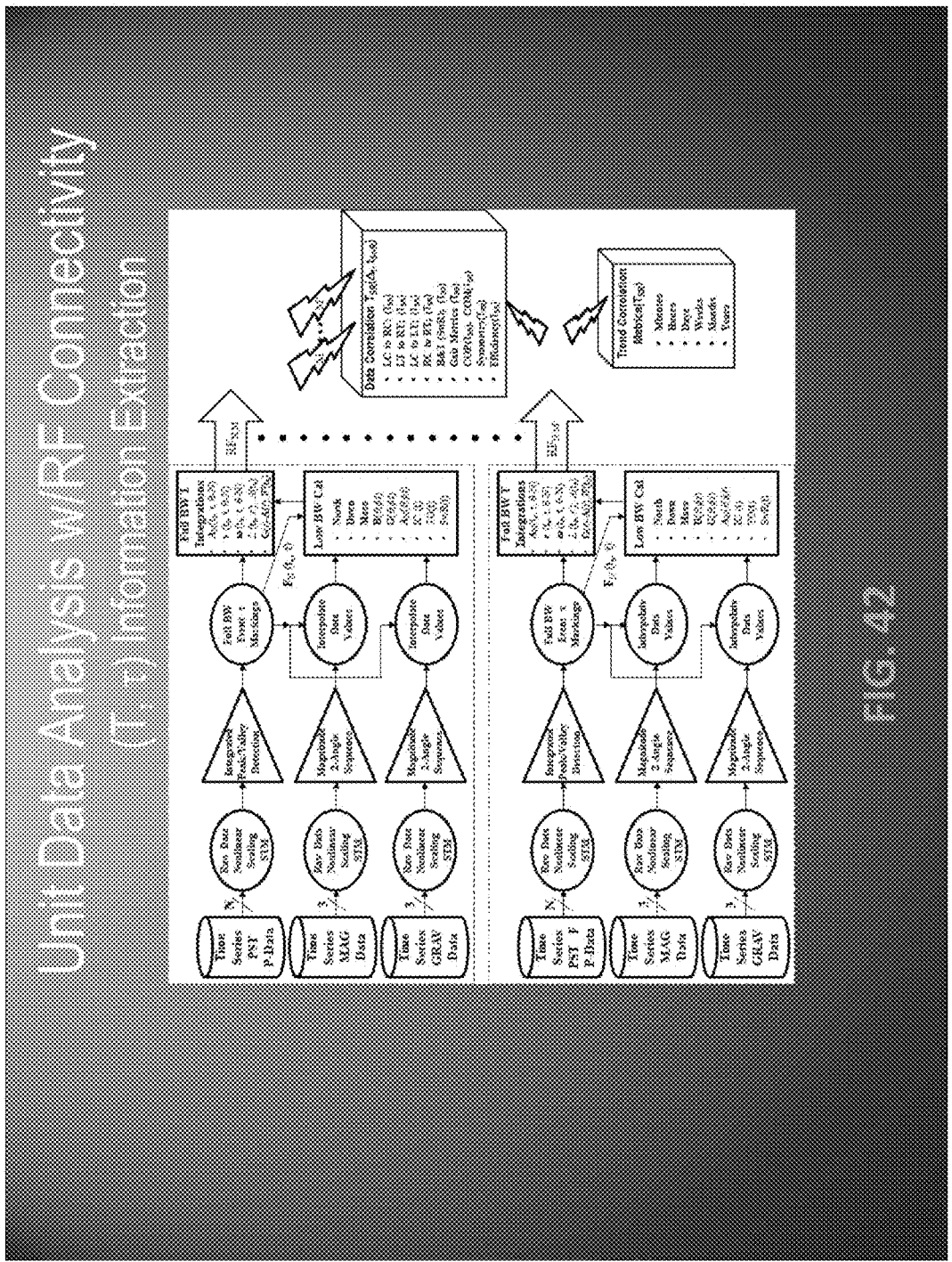

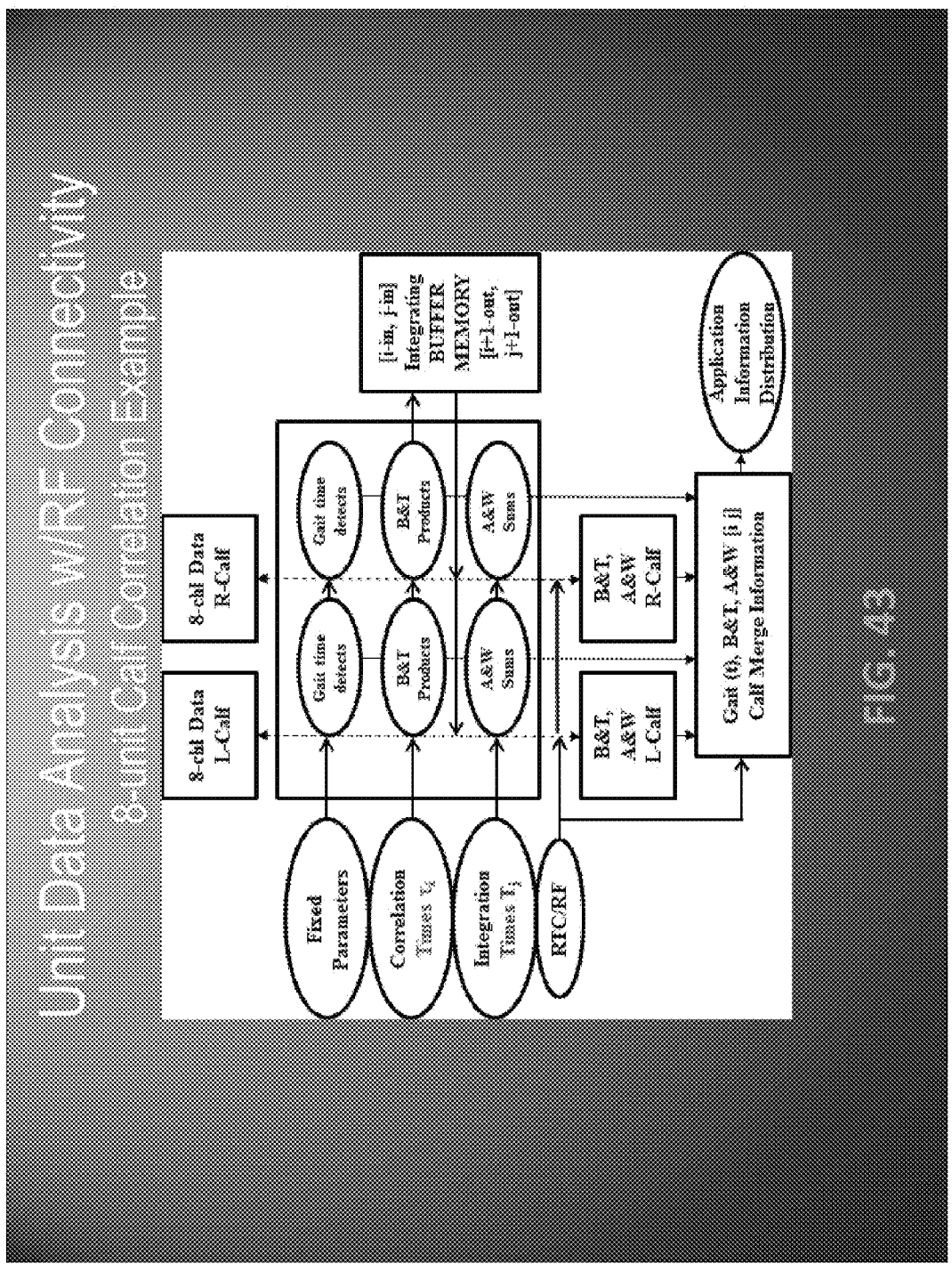

ly driven internal leg-forces, using two strap-on bands around the lower body limb muscles. Note that 'plethysleeve' refers to, for example, technology generally described in the '166 patent and '444 publication, and not compressional fabrics currently in use by sports runners.
SYSTEMS AND METHODS FOR SENSING BALANCED-ACTION FOR IMPROVING MAMMAL WORK-TRACK EFFICIENCY

CROSS-REFERENCE TO RELATED APPLICATIONS

This application claims the benefit of provisional application No. 61/723,132, filed on Nov. 6, 2012.

This application is also a continuation-in-part of application Ser. No. 13/570,152, filed Aug. 8, 2012, which is a continuation-in-part of application Ser. No. 12/805,496, filed on Aug. 3, 2010, which claims the benefit of provisional application No. 61/344,260, filed on Jun. 21, 2010; of provisional application No. 61/344,026, filed on May 10, 2010; and of provisional application No. 61/282,527, filed Feb. 25, 2010.

Application Ser. No. 13/570,152 claims the benefit of provisional application No. 61/521,278, filed on Aug. 8, 2011; of provisional application No. 61/556,365 filed on Nov. 7, 2011; and of provisional application No. 61/617,424 filed on Mar. 29, 2012.

The contents of each of these applications are incorporated herein in their entirety.

BACKGROUND AND SUMMARY

Unlike the typical motion analysis for external observation of body movement using video cameras and force plate measurements, i.e., as currently used in gait analysis for clinical human locomotion research, the plethysleeve technology (PST) as generally described in U.S. Pat. No. 7,610,166 and U.S. Patent Publication No. 2011/0208444 (the contents of each of which are incorporated herein in their entirety) measures instead, instinctually driven internal leg-forces, using two strap-on bands around the lower body limb muscles. Note that 'plethysleeve' refers to, for example, technology generally described in the '166 patent and '444 publication, and not compressional fabrics currently in use by sports runners.

As further described herein, the instrumentation of recreational runners is a newer product technology involving a simplified type of gait analysis, primarily using arrays of sensors on the feet and upper body parts to locate relative motion for extracting gait parameters. But, since the muscle force measured by PST is generated from cognitive awareness, it is similar to what might be derived from human sensing of perceived force differences, as cues in dynamic motion that efficiently moves one forward on a path. PST is modeled as a foot step placement in making a TRACK, and 'falling-forward' with gravity's pull to the next step, while maintaining stability in an upright posture by efficient appendage motion (e.g., non-translational motion or BALANCE). PST incorporates Micro Electro Mechanical System (MEMS) sensors with RF intra-connectivity and onboard processing to automatically provide locomotion efficiency information. This force sensing 'perception' is measured in real-time and is efficiently distilled into accurate parameters automatically.

As described below by way of example and without limitation, one aspect of PST measurements is continuously monitoring important muscle activity with pressure sensors in the sleeve band, such as during the swing phase, when typical gait analysis with Ground Reaction Force measurements are absent. PST is like the internal view of driving a car, by turning the wheels and pushing the gas pedal, vs. watching the wheels turn from outside with a video camera used in gait analysis. Here, PST provides a unique 'signal' of the full body dynamic, useful for medical diagnosis of deviations from normality in body function to avoid physiological failures, in mental control disruptions to prevent injury, and in deviations from normality in the elderly due to hidden disease. The technology is self-powered, using smart, inexpensive RF-networked sensor-components, being economically feasible and useful for group activities. PST scales across many event and trend time periods beyond a stride cycle, being useful to many applications, by automatically providing simple, situational assessments products for trainer/therapists. Uses range from reducing recreational injuries, improving health care for the elderly, and improving sport performance prediction and improvement using assessment feedback. This automated locomotion information extraction can be provided directly to the individual user as performance and health feedback from audio-earbud/visual-wristwatch. Or, it can be provided to a trainer's field laptop, assessing teams of instrumented players, and also as an uploaded information stream to network reporting for remote assessments, and then finally being warehoused for database mining. This further improves the locally specific cueing of information for the individual as it relates to a more global population. PST is also useful for realtime, mission reporting of military combatants, for health-assessment as Balance distortion in gait, and with potential in GPS-denied navigation, by using Track placement as location changes to augment inertial measurements.

BRIEF DESCRIPTION OF THE DRAWINGS

FIGS. 1a and 1b show Normal Gait Stance/Swing Time Periods in the R-L-R GRF Gait Cycle Stride.

FIGS. 5a and 5b show Gait Cycle Period Components Related to Energy Absorption and Generation in Running and Sprinting Relative to Leg Positions.

FIGS. 21a and 21b-1, 21b-2, 21b-3, 21b-4 and 21b-5 show Algorithm w/Realtime Hardware Architectures, Extracting PST Data Example Metrics Under Parametric Event Selection.

FIG. 24 Shows PST Sleeve Preproduction Video Gait Images, and PST Calf/Thigh Sleeve Pairs Products for Watch/Laptop Information Display and Networked Doctor/Trainer Access.

FIG. 36 shows a more detailed view of the cycle shown in FIG. 35.

FIG. 37 shows example PST data for calf/thigh muscles.

FIG. 38 shows other example PST data for calf/thigh muscles.

FIG. 39 shows example PST data event time scales.

FIG. 41 shows an example stand-alone PST device.

FIG. 42 shows example unit data analysis with RF connectivity.

FIG. 43 shows example unit data analysis with parametric control.

GLOSSARY

Figure 2:
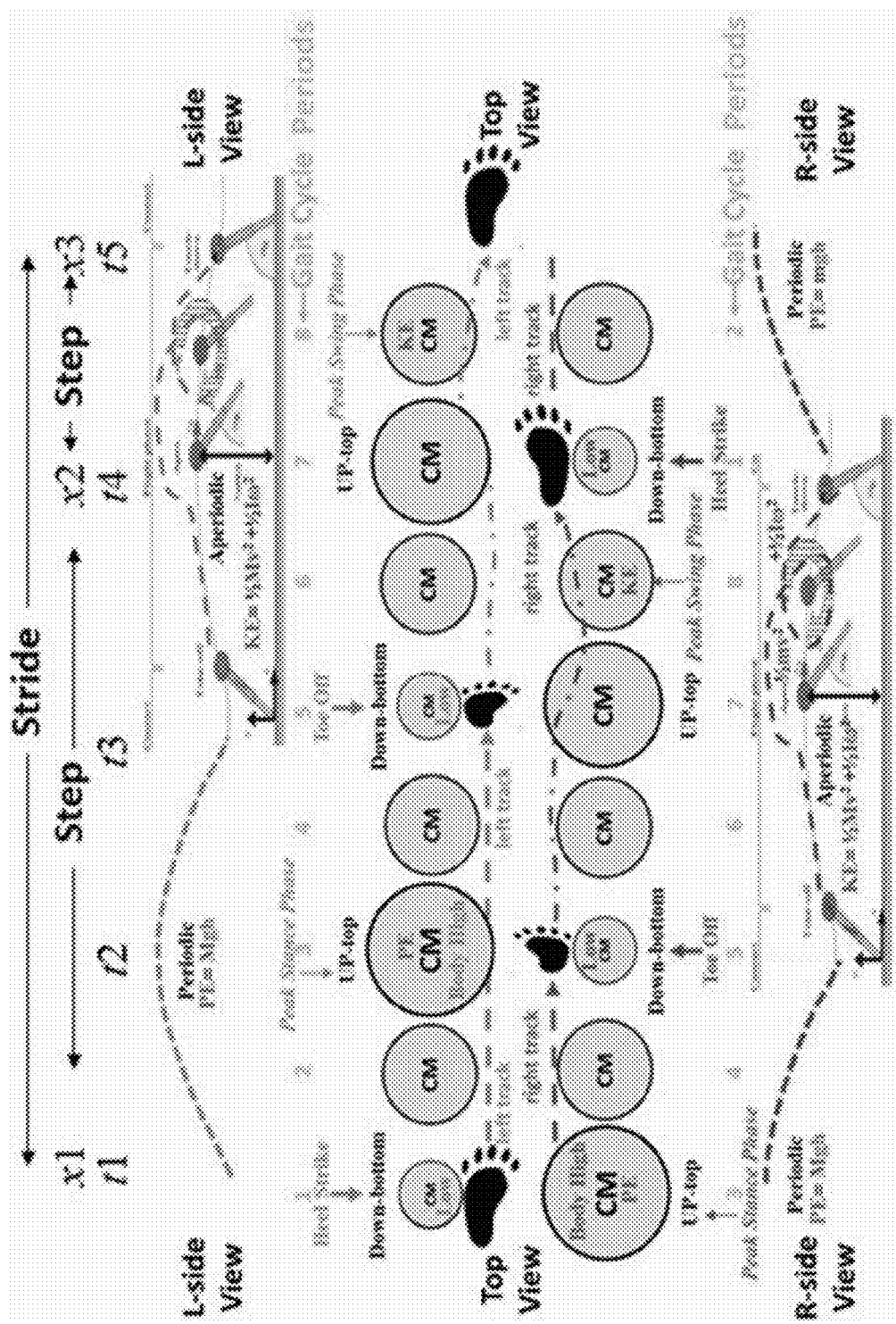
FIG. 2 Shows a Spatiotemporal COG and Foot Dynamics for a Gait Stride Cycle of Two Steps in Top and Side Views.

PST—Plethysleeve Technology
MEMS—Micro Electro Mechanical Systems
RF—Radio Frequency
GRF—Ground Reaction Force
R—Right
L—Left
ACL—Anterior Cruciate Ligament
IC—Initial Contact, e.g., heel strike
TO—Toe Off
EMG—Electromyographic (EMG) potentials
COG—Center of Gravity; also Center of Mass (CM)
ACM—About CM dynamics being motion around the body centered CM point
M—Total 'point mass' replacement location for CM force modeling
G—Earth's gravitational field vector
g—Earth's G field as acceleration
CP—Gait cycle time period
PE—Potential Energy, e.g., Mgh
KE—Kinetic Energy, e.g., $\frac{1}{2}M|v|^2$ and $\frac{1}{2}I|\omega|^2$
h—Relative vector height in PE for g (scalar distance from the ground)
t1, t2, t3, t4, t5—Sequential time markers in a gait cycle time periods for a stride
x1, x2, x3—Sequential positions in a gait cycle as space positions for a stride
I—Moment of inertia for the angular motion of the upper body
v—CM vector motion velocity for KE computations
ω—About CM angular motion velocity vector
Hz—Hertz units for frequency
SRV—Stride-to-stride variability
IR—Infrared
EOM—Equation of Motion
B—Earth's magnetic field vector
A—Foot step force vector onto ground, as measured with GRF
P—PST sleeve pressure sensor voltage measurement ($i^{th}$ indexing, as $P_i$)
COP—Center of Pressure, a pointing vector (A) to the CM location from the ground contact
L—Lagrangian Energy defined as L=KE—PE
a—General vector notation for an accelerating force vector (F) on a mass m; F=ma
Ab—Absorption
Gen—Generation
St—Stance
Sw—Swing
PCB—Printed Circuit Board
MAG—Magnetic sensors
GRAV—Accelerometer sensors of gravity
PRES—Pressure sensors
Hg—Mercury; in earlier patents for measuring pressure as a loop of Hg-filled, rubber tubing
2D—Two dimensional geometry
3D—Three dimensional geometry
Bx, By—Magnetic field components measured in a 2D XY plane
Gx, Gy—Gravitational field components measured in a 2D XY plane
FFT—Fast Fourier Transform for spectral analysis of time series data t—Scalar representing a time lag used in the time delay of a correlation calculation t—Vector of torque, pointing usually from the intersection of two other vectors in contact A—Action as the time integration of L W—Work as the vector dot product path integration of a force vector with path distance vector dx +L, −L—Notation for action and reaction in minimizing the Lagrangian time integrations RTC—Real Time Clock LF—Low Frequency HF—High Frequency B&T—Balance and Track A&W—Action and Work

DETAILED DESCRIPTION OF EXAMPLE EMBODIMENTS

The movement dynamics of mammals is a complex process of multiple limbs and muscles exerting forces to create forward locomotion. Much of the lower human leg motion is described in the dynamics of the gait cycle with stance and swing phases, as sketched in FIG. 1 to define the three body steps in a stride sequence, right (R)-to-left (L)-back-to-right (R). Many applications involving human sports performance assessment, physical therapy, lower body injury assessment, diagnosis, treatment, and recovery assessment (e.g., ACL injuries), stroke, Alzheimer's disease, etc., utilize Gait Analysis techniques that are dominated by video and treadmill/force-plate data collection in gait labs, followed by human analysis of the data. PST measures Balance and Track (B&T) of human locomotion, beyond the simple gait analysis parameters from the stance phase, but without instrumented treadmills and force plates, or video cameras, because the sleeve acquires, along with stance phase data, a unique measurement of the swing phase information without foot sensors, and automatically produces a combined metric of locomotion from additional correlation between both calf sleeves. The discussion below summarizes a simplified gait analysis representation, in order to show the uniqueness of the PST measurements, and its use in complex locomotion applications.

Gait Cycle

The gait cycle is modeled for a person walking, shown in FIG. 1a, as if in a video sequence, with numbered event periods 1 through 8, sketched with the first stance phase component as a time point (i.e., starting at 0% of the stride cycle time), for the R-foot heel strike of:

1) initial contact (IC) beginning the stance phase with the ground creating a Ground Reaction Force (GRF) to the body from this supporting limb, involving specific pelvis, hip, knee, and ankle joint positions; while these body locomotion positions change, the following, three sequential components occur after IC, for 2) loading response (from the downward body response pressure from the ground, as a spring compression from the 'falling' energy absorption), 3) mid stance from single limb support, and 4) terminal stance, of heel-off, and then moving on into the next component of 5) toe off (TO) that leads into pre-swing, for the next three swing phase components of 6) initial swing, 7) mid swing, and finally, 8) terminal swing, just before the cycle begins again, to complete the 8 gait periods.

The lower part of FIG. 1a, repeats this same motion as a circular sequence, with walking time periods spent in nominally 60% of the gait cycle in the stance phase, and 40% spent in the swing phase. Comparing the eight gait cycle periods, clockwise around the circle, the percentage of time spent in part of the cycle is shown. The stance phase begins with a double-support mode from L with R legs at IC (R-leg heel strike), and then a single-support mode from just the R-leg at mid stance (R, swing-L), moving back to the double-support from the R with L legs, just before the toe-off (TO) component of the R-leg is at preswing (i.e., L-leg moving into stance IC). Here, begins the swing phase, with the acceleration of the R-leg into the swing from behind the body and then being moved forward, through the remaining cycle. Note that two feet are on the ground in a double support stance, in the transfer between the L-to-R foot in the beginning, and this is repeated for the R-to-L foot in the termination (IC to TO to IC). It is also instructive to watch a video of human locomotion on a treadmill (e.g., FIG. 24 shows the 8-component frames), because while these phases are fundamental to gait analysis, humans have many other, eventful changes in locomotion, such as rotating the foot slightly for a particular step, only discovered from human study of the gait videos.

In summary, walking locomotion is modeled as an eight time period sequence for each leg spending 40% in the swing phase of one limb (synched with the other in single, along with double limb stance totaling 60%), and then moves into stance phase while the previous limb moves into swing. These percentages change to an increased swing with running Thus, lower body dynamics require considerable balance to maintain effective locomotion in making a track as sequenced footprints placed on the ground. Walking can be described as an evolving falling down process, while balanced on one leg, with a recovery by quickly moving the other leg forward to catch the fall in the swing phase. The GRF in FIG. 1b is measured with gait analysis force plates, varying with vector components of loading and friction during the cycle, where the foot force pressure moves down the sole, as shown on the right side of the figure (i.e., heel strike, flat foot to heel off, then toe off; shown also in two foot pictures on a treadmill for heel strike and toe off), with the left side showing a GRF loading force, and a stance phase GRF-dip during single limb support (while the other leg is swinging), and then during swing the leg shows a GRF=0. The GRF plot shows only 36% of this walking stance phase has both feet on the ground for stability.

Considerable research in gait analysis using force plates that measure GRF, as a three dimensional loading vector with friction components, is used to understand the body dynamics, and the dynamics of this force determine the three dimensional momentum of the foot as well. The body vertical force exhibits the double peaked curve during the stance phase of the gait cycle shown in FIG. 1; i.e., it increases from zero to 10% above the body weight during the stance phase, decreases to 60% of the body weight during transfer, and then increases back-up again to 10% above, and then decreases back to zero at TO during the swing phase initiation of the other foot. There are over 20 muscles involved with the gait cycle, including dominance within all phases from five: gluteus maximus, gluteus medius, vasti, soleus, and gastrocnemius, with stability being brought from muscles that do not span joints and contribute to the contact loading force, as measured indirectly with the PST pressure sensors around the thigh and calf of the lower body regions described in a later section.

Electromyographic (EMG) potentials, measured using electrical probes inserted in the muscle tissue or placed on the skin, display further action of the muscles during the gait cycle. This EMG data is the standard model for gait analysis of a force representation using GRF measurements to understand various muscle contributions.

Modeled Two-legged Gait Cycle Dynamics

The gait cycle is shown more specifically in Side and Top Views in FIG. 2 (with the same gait cycle numbers shown just below the "L-side View" legend at the top, and just above the "R-side View" at the bottom, as used in FIG. 1a), in order to see L-R leg synchronization, including the up/down body motion of the center of gravity (COG, as Earth's gravitational force vector G).

In FIG. 2, the G vector force is an acceleration g, on the body's center of mass (M, abbreviated as CM), beginning at the lowest height (h) position for lowest Potential Energy (PE) "bounce-down" time t1 and x1 (L-foot step) in heel strike for the first step (indicated as a top view footprint, gait cycle time period (CP) #1, with a gray circle indicating body height by the diameter as if it is at a distance away from the viewer). The stance PE "bounce-up" is drawn in the L-side View at the top of the figure as an inverse pendulum, swinging in a half sinusoid, beginning at time t1 in the drawing, peaking at t2 (mid stance, CP #3, with PE increasing as the circle appears closer to the viewer), and returning back at time t3 (toe off, CP #5, with a top view "toe-print," beginning the aperiodic, nonlinear swing motion CP #5 to CP #8). Here, the R-foot is in heel strike at x2, time t4 for the second R-foot step (#7), with the Kinetic Energy (KE) maximized (CP #8) from the inertial (I) component of angular swing velocity ($\omega$) momentum ($\frac{1}{2}I\omega^2$), added to the linear velocity (v) forward momentum ($\frac{1}{2}Mv^2$). The third step in the left foot sequence is the return of the L-foot to the new cycle as a beginning heel strike.

Muscle Brain Control Functionality

The model for locomotion is that of the cognitive brain process commanding specific direction to engage groups of muscles in a synchronized completion of locomotion actions. It will be shown in the example embodiments of the PST that the muscle groups appear to operate in a self-synchronizing manner, particularly in the running phase. In an examination of the neurophysiological basis of adaptive behavior through EEG measurements, Freeman has shown a mass action model for collections of neural "masses," with time-space behavior in a feedback loop control, which includes limit or terminal cycles, from impulse driven oscillations having characteristic frequencies from a periodic driven nature, or an aperiodic behavior at the sub-system levels. On a global scale, these brain-commanded sequences are brain wave frequencies of alpha (8-12 Hz), theta (3-7 Hz), beta (13-30 Hz), and gamma (30-100 Hz), which are steady state, self-sustaining activities, but show a very short spectral resolution, as an inverse square frequency roll-off for temporal correlation. Freeman proposes the aperiodic activity as stochastic chaos, which is a "ringing" of limit cycle attracters. One can extend this model to dynamic locomotion muscle actions as being impulse driven, aperiodic behavior at the local level, which is globally maintained in a more periodic control function based on the cognitive intentions of the brain. Such behavior might arise from training as 'muscle memory.'

Hence, in gait analysis, one can see stride-to-stride rate variability (SRV), representing human walking locomotion as an interaction of the central nervous system in the neural functions of the brain, and the intraspinal nervous system with the mechanical periphery at the bones and muscle levels, as a biomechanical model. This is a proprioception sense of locomotion, because there is a feedback from the limb tendons, muscles, and articular joints. However, kinesthesia is distinguished from locomotion by excluding the sense of balance. Proprioception is considered a feed-backward perception by making post-action adjustments with 100 msec delays; however the feed-forward component for balance is also postulated in proprioception, where it is used for more rapid actions based on a pre-action knowledge of the limb locations, such as used in placing the fingers on the nose during a sobriety test to be within 20 mm. Various training mechanisms can improve this balance sensing, such as juggling or standing on a wobble board, which is enhanced with the eyes closed. Thus, locomotion is a combination of footfall placement knowledge after steps occur, and a sense of balance is used for the next footfall placement, creating a track motion. Gait analysis using IR stroboscopic photometry has shown that elderly subjects had up to 20% reduction in velocity and length of stride (with stooped posture, faster cadence, and increased double limb stance) over young adults, and which also included reductions in toe-floor clearance, arm swing, and hip and knee rotations. This is a combined reduction of cadence and stride that normally reduces the expenditure of energy, under the criteria of energy conservation. While this reduced action can be considered that of a change in the neurological health of the elderly, this is why the combined determination of track and balance, when studying the conservation of energy in gait analysis, is critical to avoid artificial effects from stiff joints or absence of breath in the elderly (i.e., requiring a normalization within a variety of studied gaits).

There are five basic temporal patterns in locomotion conditions, and when studied with four walking conditions (normal, kicking a ball, stepping over an obstacle, and stooping right and left while grasping an object), using EMG muscle recordings from between 16 to 31 ipsilateral limb and trunk muscles in a set of 8 subjects, results showed that muscle activation associated with voluntary tasks was either synchronized with the locomotion, or had additional activations supporting a superposition model of compound movements. This complexity can be modeled with nonlinear mathematics shown in multifractal and chaotic Equations of Motion (EOM), and exhibit periodic and aperiodic behavior, which also exhibits irregular SRV, leading to falls in young children.

Unsteady locomotion is a sign of poor integration of muscle function with whole body dynamics and neuromuscular voluntary control, where fast-motion (e.g., running) depends more on local control that can be best modeled with spring-mass dynamics, which creates stabilization during unsteady running from changes in terrain, lateral impulsive perturbations, and changes in substrate stiffness. These stabilization modes might be based on initial conditions, as seen in chaotic models, where the conditions arise from proximo-digital (i.e., length of the humerus) differences in limb muscle architecture, function, and control strategy. Nonlinear fractal exponent modeling for the data has supported correlation with forced pace gait conditions (i.e., metronome pace) having similar fractal exponent values to Parkinson's disease.

There is also a feedback that compensates for length dependent neural control, using ground contact sensing from GRF, which cause a redistribution of energy by the distal muscles through their tendons. The optimization, of this energy use in locomotion, can allow mammals to achieve stability under a variety of conditions. Comparisons between GRF and kinematic (ultrasound) gait measurements of heel-strike and toe-off identification show high correlation, with slight differences with gait speed. This basic locomotion biomechanics is a vaulting over stiff legs in walking and compliant legs in running, but further analysis of these models with data requires a compliant leg for both, and shows that gait is but one of many legged motion solutions accessed by energy and speed, and is useful in stable animal and robotic locomotion. Another element of stability is in the use of a retraction of the swing leg through rotation, just prior to contact with the ground, changing the spring-mass angle-of-attack in responses to disturbances of stance-limb stiffness and forward speed. Robotic studies of four-legged locomotion in simulated and real environments are optimized to minimize energy use in gait locomotion.

Locomotion Upper/Lower Body Dynamics

Figure 3:
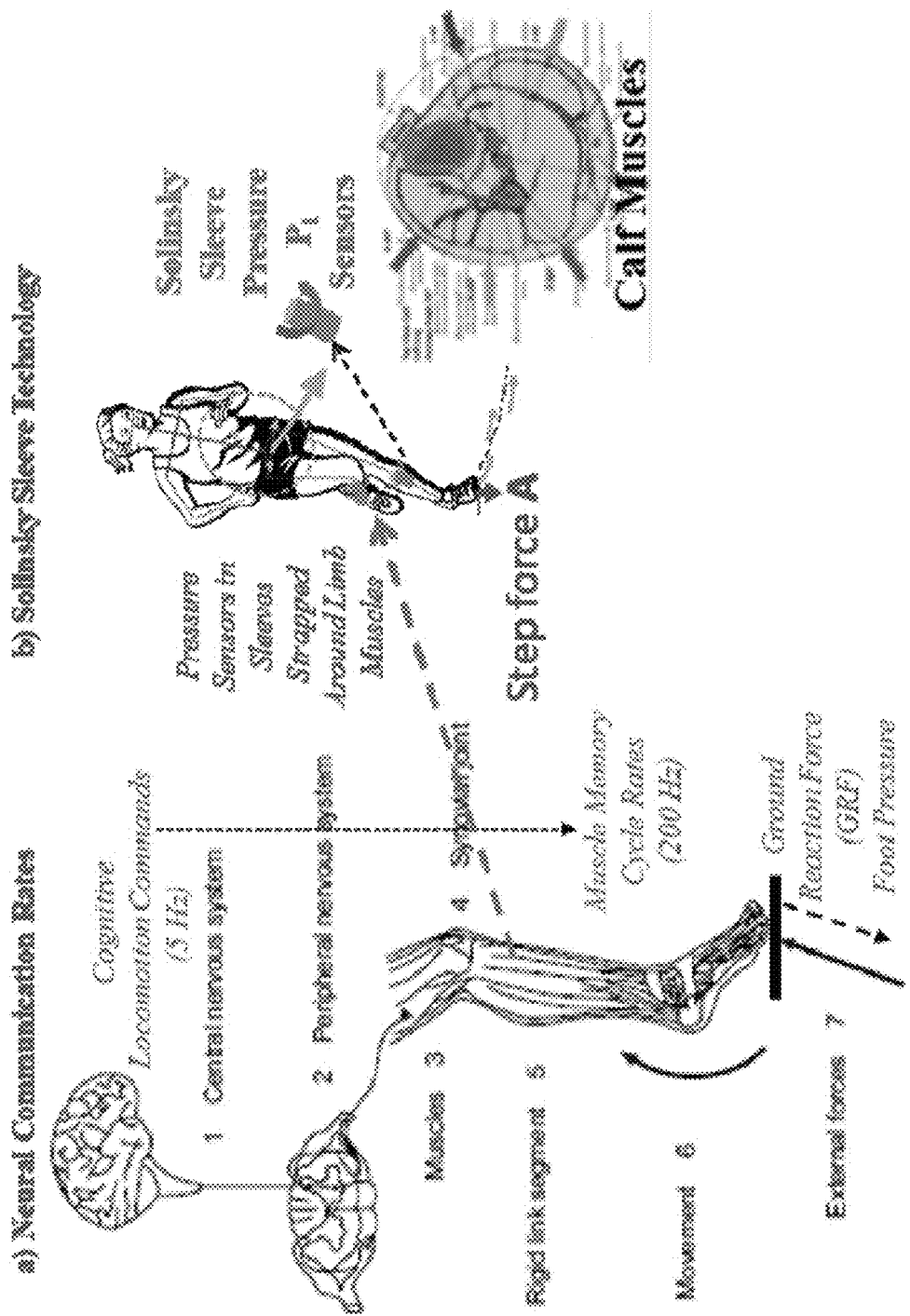
FIG. 3 Shows Modeled Interaction of Cognitive System Commands, Executing Calf Muscle Memory Pressures for L-Foot Step Force.

This gait cycle locomotion action by the lower body can be modeled as an action of the body CM movement in the earth's gravitational field, G, while exerting angular momentum from the upper body motion through the pelvis, about the body CM, as an about center of mass (ACM) motion. The ACM angular changes were measured with respect to the Earth's magnetic field vector (B). Finally, the GRF of the foot thrusts, made during the gait stance as a transfer of CM weight between the two feet, and also as a balance of one foot, while the other foot was in swing, creates a reactive force vector (A) in response to the Earth's force G. This is a vertical pressure component, and two lateral shear components (shown in FIG. 1b as loading and friction). A pressure sensor can be used to actively measure these force amplitudes as determined by the circumferential pressure changes at the lower body calf positions. FIG. 3b shows these muscle size changes, measured by the PST sleeve shown on the right calf as pressure $P_i$ for each $i^{th}$ muscle sensor measurement (shown in the inset of a calf-muscle cross section). These muscles are being commanded by the cognitive brain (FIG. 3a, e.g., 5 Hz rate), and exerted with 'muscle memory' training (FIG. 3a, e.g., 200 Hz rates), creating a foot thrust, step force vector (A) onto the ground.

Importance of Muscle Energy Absorption/Generation

Figure 4:
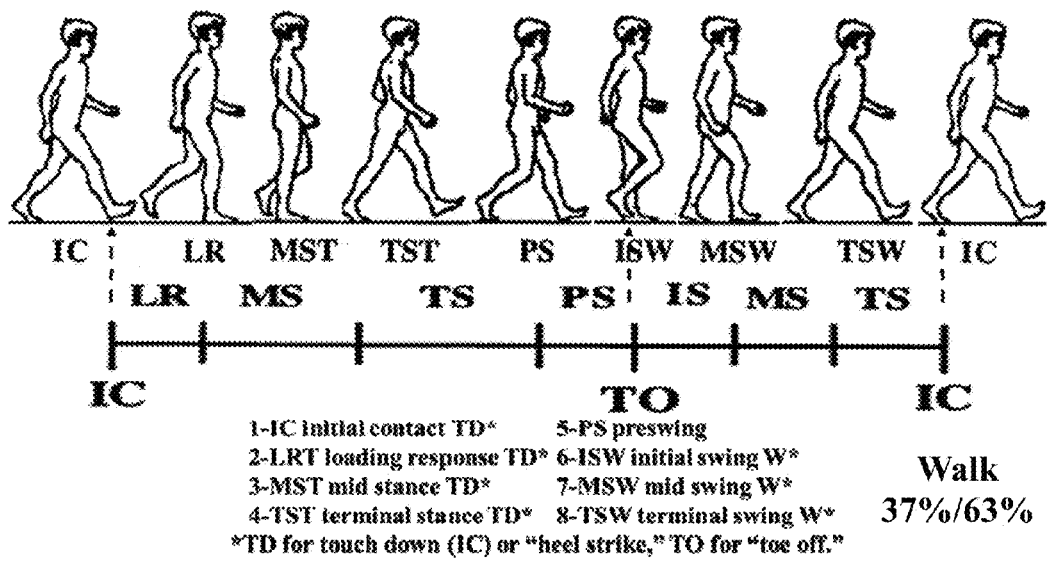
FIG. 4 Shows Eight Gait Cycle Periods in Stance/Swing Walking, Beginning and Ending at Initial Contact (IC) During a Stride Cycle.
Figure 5:
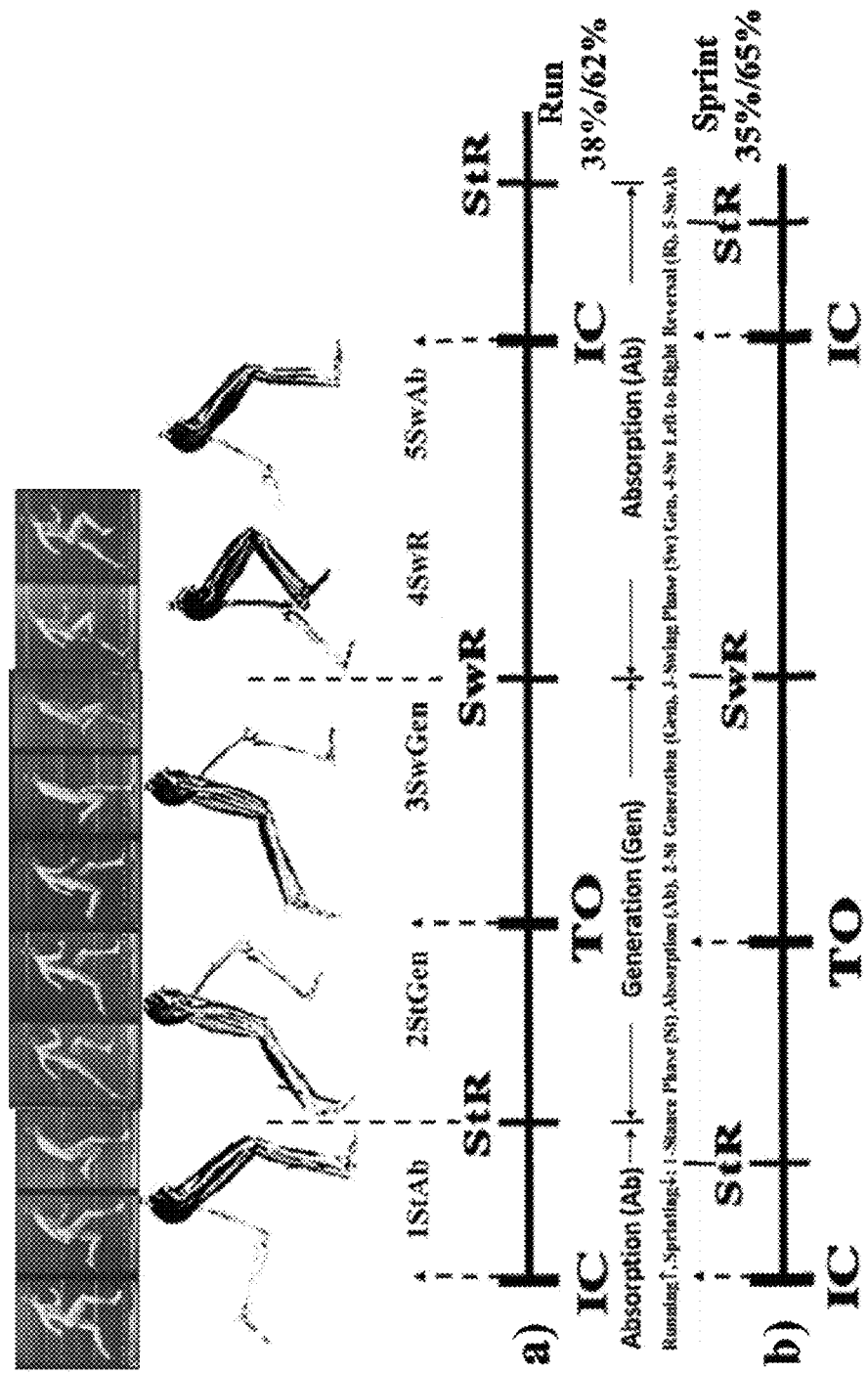

FIG. 4, taken from a more recent description of walking, shows the common modeling of the gait cycle with a similar, sketched human walking in the 8-definable dynamic periods, i.e., the stance phases defined here in the figure as LRT, MST, TST after foot touching the ground, IC, and the swing phases of ISW, MSW, TSW, with the most important dynamic being the preswing, PS, which precedes the foot-thrusting toe off dynamic, TO. The walking gait cycle is contained within the two steps of IC-R, TO-L, IC-R, shown as swing to stance percentages at (37%/63%) respectively. Here, during the PS, the cognitive commands to the lower body muscles, are supplying a derivative of sensing upper body dynamics by the brain and perceived forward motion dynamics, to inform the brain how to create the magic of swinging the lower body limb to re-engage the stance phase of Track, again in Balance. Improper Balance creates problems in Track, and Track problems create improper balance. FIG. 5 is a rescaling of FIG. 4, for running (FIG. 5a, upper) and sprinting (FIG. 5b, lower) dynamics, showing energy absorption and generation within the gait cycle (using abbreviations defined in the figure). There is also shown at the top of FIG. 5, an overlay of the famous Muybridge still photographs of a runner, here cut into a different sequence to match up with the stick figure drawings. The temporal cycle retains the IC-TO-IC gait cycle markers (with other markers; i.e., a reversal in stance being R-to-L shown with feet and lower body muscle drawings, noted by StR, and a reversal in swing being L-to-R, noted by SwR). These other markers have placement in time distinguishing between running (upper linearly marked bar) and sprinting (lower, linearly marked bar). Here, the swing to stance percentage ratio increases, for running as (38%/62%) and sprinting as (35%/65%). Notice also in the photographs, the elaborate extension and compression of the calf limb relative to the thigh limb, by the lower body muscles, beginning in the StR point, into just before the IC point occupying over 8-frames of the runner pictures (e.g., maybe 11, with angular changes in degrees of roughly 180° to 30°, and back to close to 170° at the end of 11 frames, or on the order of 700 degrees/sec!).

However, in FIG. 5, the difference from walking, shows only 5-phases, which focus on the absorption (Ab) and generation (Gen) of the energy being transferred by the leg forces within the gate cycle, indicated by Ab/Gen in stance (St), i.e., 1StAb, 2StGen, and in swing (Sw), i.e., 3SwGen, 5SwAb, and the swing phase reversal, 4SwR, occurring right after the SwR marker. This modeling is closer to the representation in the '166 patent, which measures the muscle action with pressure sensing at muscle locations circumferential around the PST band, shown in FIG. 6, and discussed in the next section. Specific sleeve sensors on individual printed circuit boards (PCBs) measure the angular motion with a magnetometer (MAG), the gravitational forces with an accelerometer (GRAV), and the muscle forces with a pressure sensor (PRES), around the sleeve band, as indicated in FIG. 3b for the six sensor boards, located with arrows around the calf muscle cross-section.

Sleeve Information from Correlation Metrics

Figure 6:
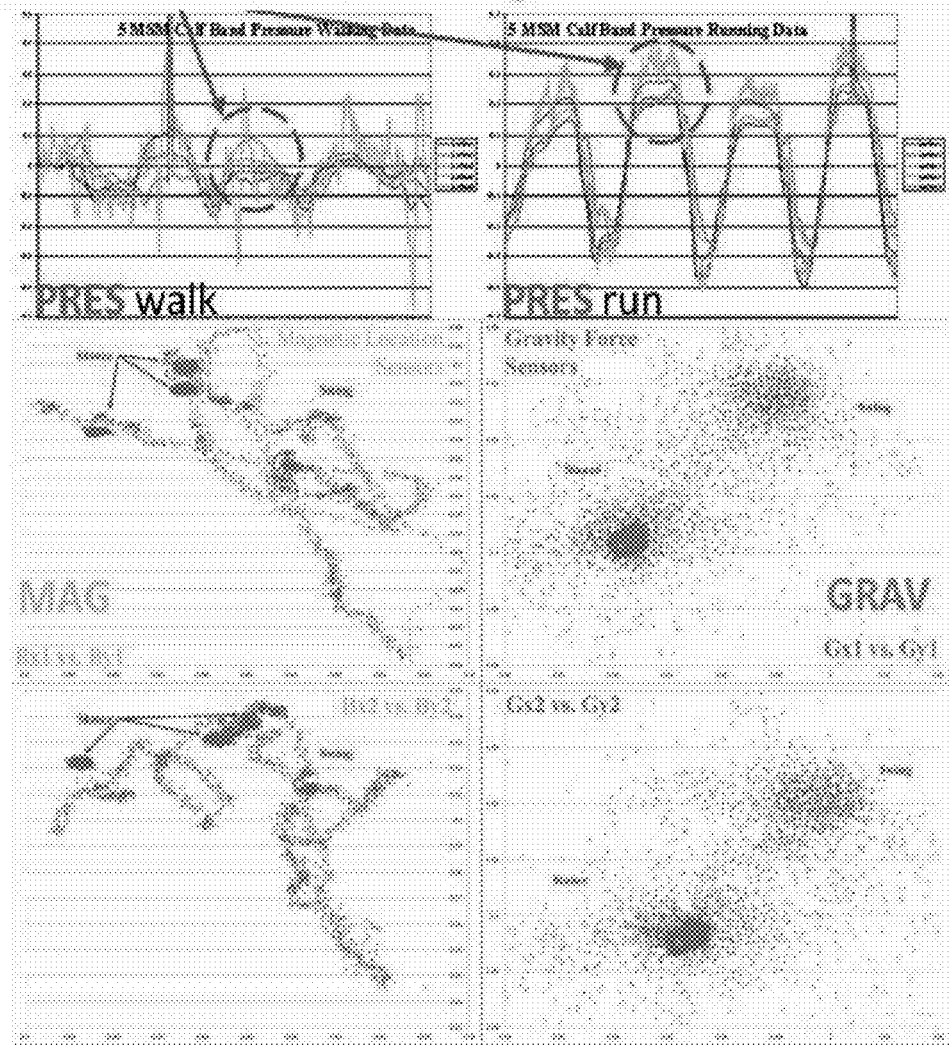
FIGS. 6a and 6b reproduce an Earlier Plot of PST Tri-MEMS Recorded Data in Gait Walking/Running Examples for Collocated PCBs on the Sleeve.
Figure 7:
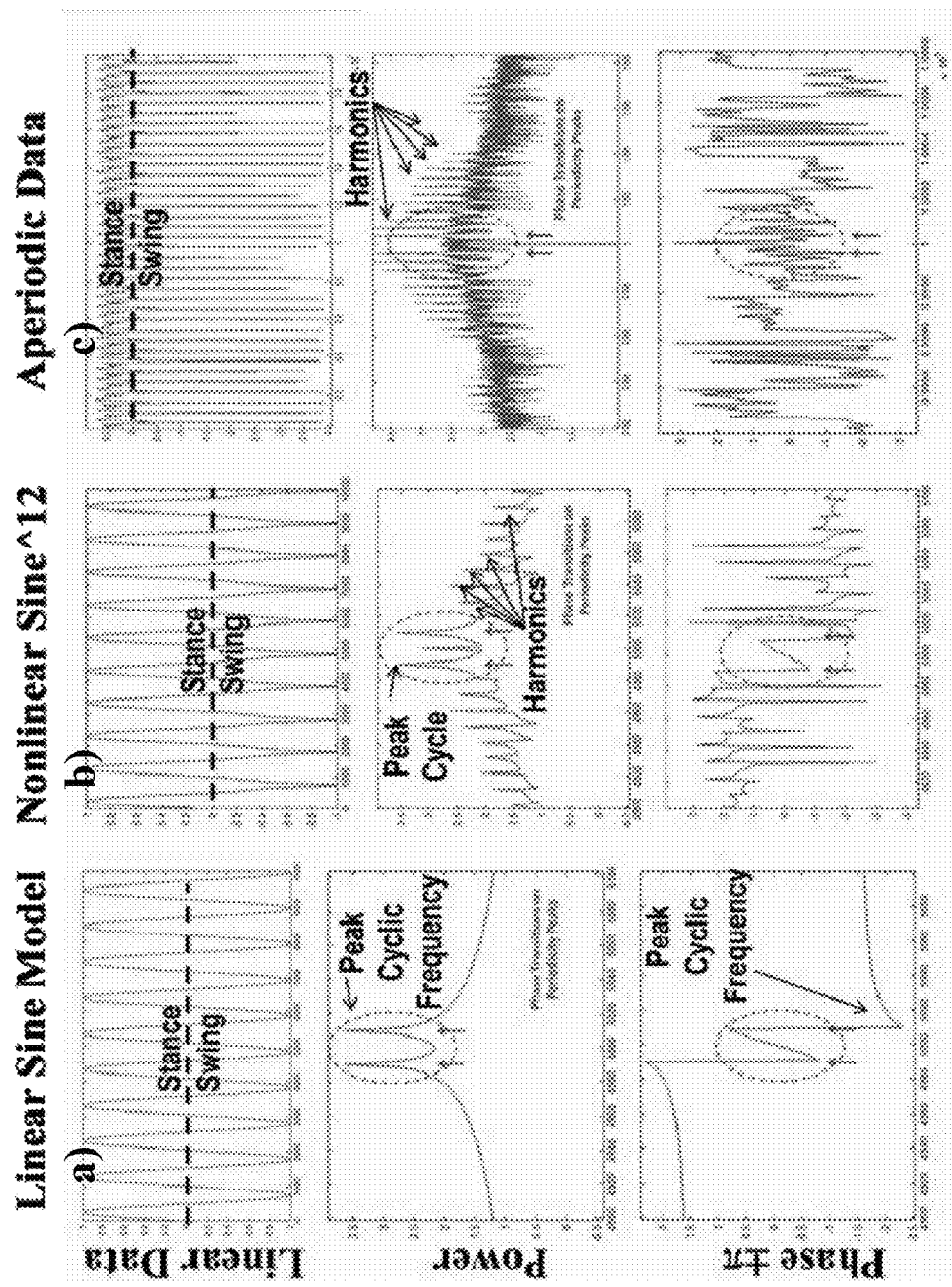
FIGS. 7a, 7b and 7c show Simulated and Real Linear/Nonlinear Gait Dynamics Examples in Time and Harmonic Spectral Amplitude/Phase Synching
Figure 12:
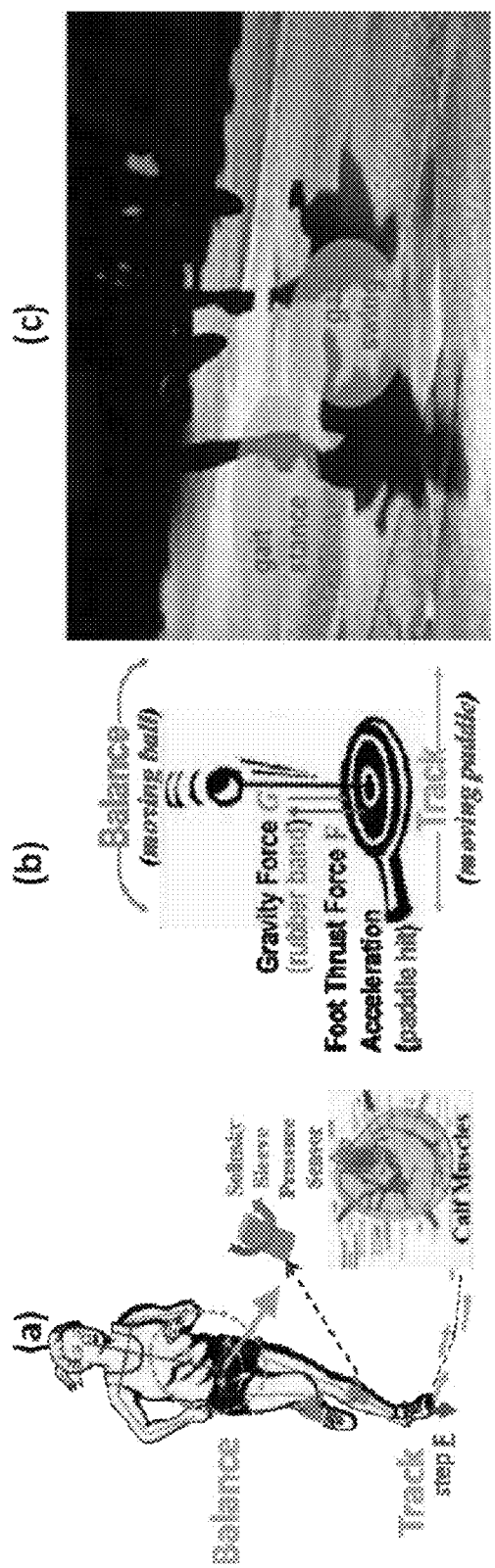
FIGS. 12a, 12b and 12c show Balance and Track Locomotion in Analogy to a Paddleball Toy for Ball Stability/Instability as Changes Affecting Each Other.

The metrics derived from the Balance and Track PST measurements are detailed in ('444 publication, '166 patent), citing figure numbers from '444 publication (3—Fig notation), are made relative to previous biomechanical models and measurements (3—FIGS 6a-6e), and an example of the modeled swing motion nonlinearity is also shown (3—FIG. 7). The sensing technology is shown migrating from Hg loop pressure sensors to bands of MEMS (Micro Electro Mechanical Systems, 3—FIG. 9), with a specific example of Left-Thigh and Left-Calf Hg loop data (3—FIG. 12), showing the correlated motion displayed in the FIG. 5 photographs of the runner, with both parts of the double inverse pendulum in motion. The combined sensor groupings (3—FIG. 9) are on each PCB placed on an angular location around the band (3—FIG. 14) for pressure relative to the muscles (3—FIG. 15, 16), and magnetic and gravitational-acceleration forces (3—FIG. 18). Data measured over a few gait cycles are shown (3—FIG. 21, as pressure for walking and running, and in 3—FIG. 22, as collocated 2D magnetic, gravitational (x, y) measurements). FIG. 6 shows similar data, with point connection lines removed.

Notice in the top part of the FIG. 6, i.e., FIG. 6a with the dashed-line circles, there is the usual increased pressure from the thrusting in the stance phase (StR through TO of FIG. 5), as a partial, linear sine wave structure of the periodic inverted pendulum (upper left side, "PRES walk"), which flattens at the top during running (upper right side, "PRES run"); also note in both walk/run examples the nonlinear motion with a more narrower, valley shaped "sine" wave in the swing phase, with the same half period as the stance, but as a more pointed dip. This is the aperiodic nonlinear motion of the swing phase. The pressure is shown for five PCB measurements, from pressure sensor (PRES) examples $P_i$ (i=1, 2, 3, 4, 5) being synchronously overlaid in time in FIG. 6a, with four periodic stance phases of the single right leg calf sleeve, as half sinusoids in five-colors for different muscle positions around the sleeve (some have noise contamination). One can also see the individual muscle measurement contributions changing within each cycle indicated by a dashed circle, where each muscle contribution to the gait cycle is slightly different in dynamics within the cycle, as if some muscles fire sooner or later in the periodic motion, and also at different times in the swing phase. This overlay is also apparent in the swing phase of both the walk and run data. The walking data is like a standard inverted pendulum model, but for running gait models, the body operates more like a "pogo stick," with both feet off the ground at once in a swing phase, but landing on one at a time in the stance phase, thus showing more difference in the plot through the swing "valley" for each muscle. These variations with pressure sensor measurement around the sleeve can be useful for a more refined characterization in locomotion, such as in patients with hip or knee problems, or for a preference in footprint lay-down, caused by ankle issues. Pressure data differences of neighboring boards in this data region can show a variation within gait period, to monitor trends with the rotation of the limb (from B) in correlation with variations in the muscle component contribution (from $P_{i+1}$-$P_i$).

The two orthogonal sensor measurements of FIG. 6b (i.e., on the left for Bx1 vs. By1 and Bx2 vs. By2; and on the right for Gx1 vs. Gy1 and Gx2 vs. Gy2) are plotted as scattered point pairs in time, over the gait cycles with the swing and stance phases indicated for both sets of boards. Since during the stance motion, the leg is not moving much, the MAG location dots are then in a smaller sized group, as shown for three marked stationary "stance" groups (there is also a fourth group for the four stance pressure markings, grouped just under the "swing" labeling of the swing dot patterns). But in the swing phase, the MAG motion traces out a relative angular pattern reproduced roughly as a retrace in the same structure on each of the cycles shown. This dynamic motion pattern is the 2D projection from the 3D calf motion shown in the earlier runner photographs, which can be combined from the two boards for a 3D MAG angular location position. Similarly, the acceleration data is shown on the right side of the figure, with a similar tight clustering of a gravitational field force during stance, which then expands out as an increased gravitational force grouping, changing to a larger acceleration value, due to the centrifugal force acceleration change during the swing state, causing an apparent "increased" gravitational force, pulling on the leg as it swings (i.e., like at a playground, sliding out and holding with just one's hands, while rotating on the merry-go-round table). Note also, that the pressure shows continuous data changes between swing and stance phases, with nonlinear peaked pressure reductions during swing, being correlated with increased GRAV measurements. This indicates the centrifugal force reduces the sleeve pressure, from decreased circumference during swing. A modeling of this dynamic stance/swing pressure is discussed next.

Force Pressure Simulation Model

A simulation model was developed that recreates the rounded up pressure of the stance, and the downward, narrowed, "valley" pressure of the swing, as shown in FIG. 7. Here on the left (FIG. 7a) is shown a linear sinusoid dynamic for linear periodic motion in an inverted pendulum model, with a stance phase delineated from a swing phase by a dashed line, assuming equal stance and swing time periods. This has a singular spectral peak in the power, shown in the FFT of the data in the second line of this column (marked as two sided frequencies, with a Fourier phase transition at each peak shown in the third line). The nonlinear nature of the swing phase was created with a $12^{th}$ ordered sinusoid synchronized to the fundamental, shown in the center (FIG. 7b) as a replacement part to the linear data on the left side, in just the swing phase. Note that in the second and third rows, this data has added harmonics from the nonlinearity, which also have phase transitions confirming the synchronization. Finally, on the right side (FIG. 7c) is shown the same format as the center simulation model, but here real, aperiodic PST data is shown at the top, with a compression of the stance amplitude 'up' from the dashed line, and as an expansion of the swing amplitude 'down' from the dashed line. Here, the Fourier analysis has similar harmonics and also with aligned Fourier phase transitions. This data supports the model of a self-synchronization form in the swing phase of the gait cycle.

Energy Absorption and Generation During Muscle Force Exertion

Figure 8:
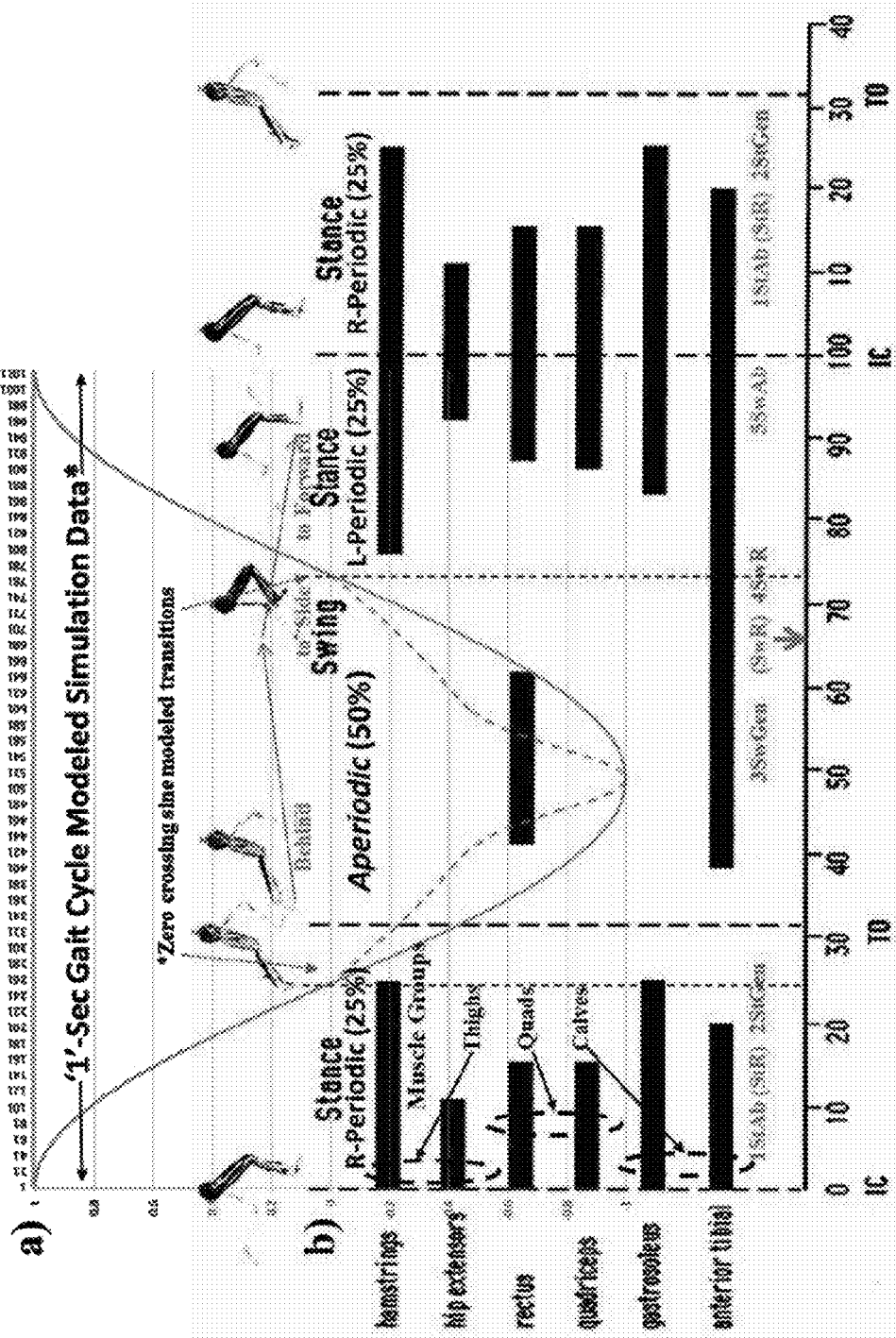
FIGS. 8a and 8b show Modeled Running Muscle Action-Absorption/Work-Generation for Periodic-Stance/Aperiodic-Swing (1.3 cycles).

The feature of the muscles in synchronization, as shown in the modeling of the '1-sec gait cycle' in the simulation and data example of FIG. 7, can be examined further in terms of energy absorption from compressive muscle force 'springs' and energy generation from expansive muscle force springs at a later time. FIG. 8 is a similar drawing to FIG. 5 in terms of the absorption and generation during the gait cycle. However, here in FIG. 8b the cycle is extended into a 1.3 stride time period (IC to TO to IC to TO), with an overlay of various muscle groups contributing to the locomotion. The extra stance-phase time plot allows for these muscle groups to show continuity across the stance from 'R-periodic' on the left side of the figure, to the 'L-periodic and R-periodic' on the right side of the figure in a double support transfer. The FIG. 7 simulation is overlaid here as FIG. 8a for a 1.0 stride-time, and aligned with IC to IC time points. The solid sinusoid line crosses zero, as a dashed curve to show the nonlinear swing phase, where this nonlinear component matches up perfectly to the zero-crossing transitions and what would be the continuation of a linear periodic. Within the errors of this graphic, note that in this aperiodic phase, the nonlinear swing motion is arbitrarily occupying 50% of the cycle to show relationship of the R/L periodic stance phases with the aperiodic swing phase. Note also, that the swing leg, anatomy drawing shows motion from back-to-side-to forward of the other leg in stance as shown in the middle leg drawings about the swing reversal point (SwR, indicated in the bottom of the figure with an arrow). This is the same indication to be shown in FIG. 10 for a Lagrangian energy change. This motion, driven by the rectus and anterior tibial muscles, is not measured on a force plate in gait analysis, and has an enormous contribution to the Work and Action efficiency. It is a means of generating energy for the later stance transfer and handoff to the upper body angular momentum. Extraction of correlation, as metrics of information, is described next.

Balance and Track Metrics

Figure 9:
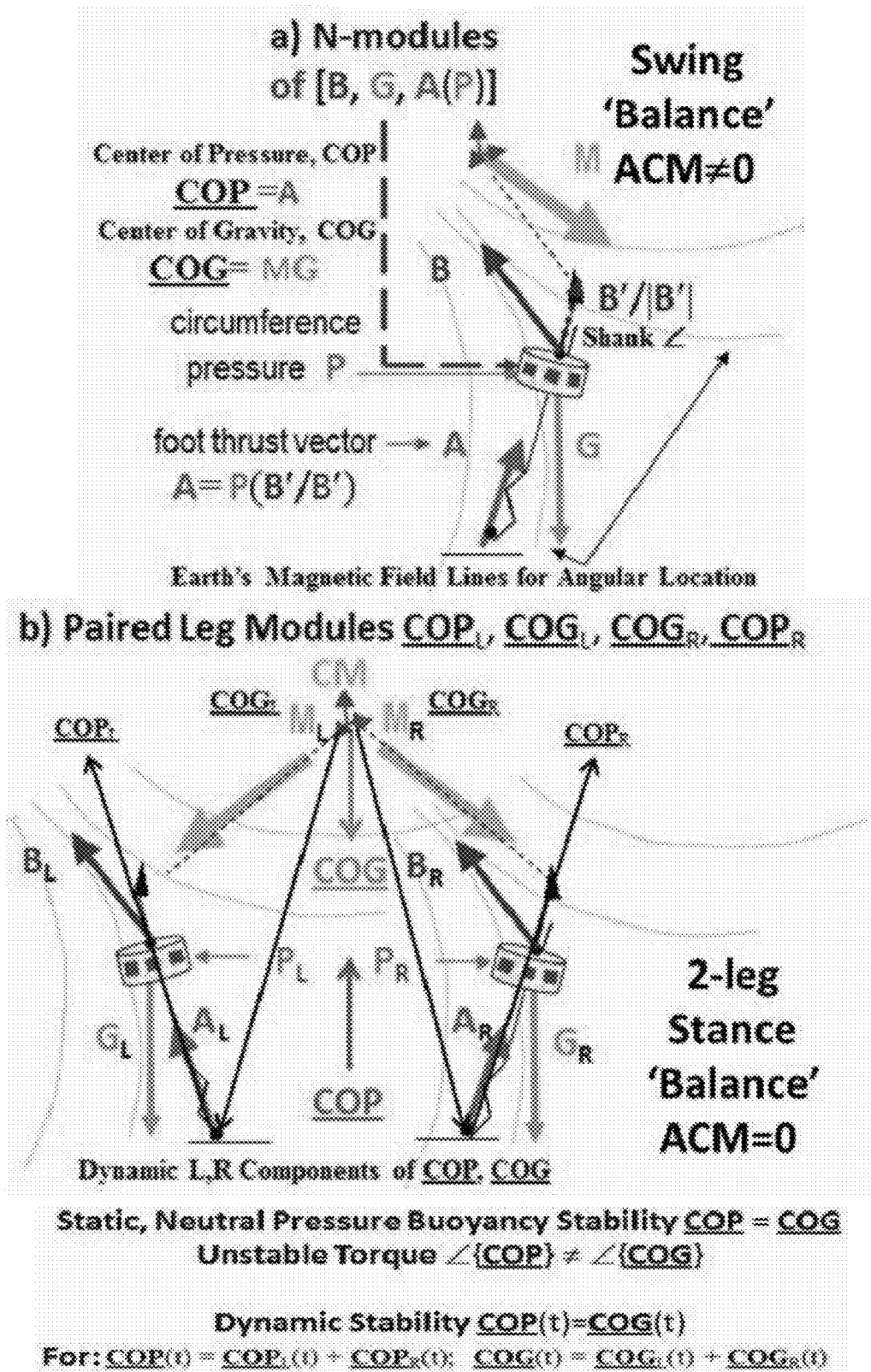
FIGS. 9a and 9b show N-Module Sleeve Measurements for a Single Leg Support and a Double Leg Support, with COG/COP Alignment Defining Balance.

The metrics of balance and track are based on the application of the foot force vector A, created from the pressure measurements of the sleeve, P, and the B vector location, as shown in FIG. 9. Here, the CM is at an M vector endpoint, relative to the sleeve location, shown as a band of rectangular MEMS boards, synchronously measuring the B, G, vectors, and the scalar Pressure (P) from the R/L calf-sensors. By using MAG sensors for the angular orientation of the calf limb, relative to the Earth's magnetic field lines (B'/B') as the "shank angle," this can be combined with P to estimate the actual force vector A, as A=P(B'/B'). The definition for the Center of Pressure (COP) is vector A pointing up. In FIG. 9a, such as for a single foot support during swing, misalignment of A with G shows a vector torque exists to create an unbalance. In FIG. 9b, the COP, COG vectors are symmetrically aligned for both feet shown as occurs in a double support stance. The L-R calf sleeve data thus estimates Balance as a miss alignment between COP and COG, and during single limb stance, angular momentum conversation sustains balance with an offset vector (mean ACM motion over a gait cycle is not zero, without another contribution for Balance). By examining both legs together, the gait cycle is simplified with dynamics as the single foot (swing) in ACM≠0, and double foot (stance) with ACM=0. Dynamic stability is defined by the equations at the bottom of FIG. 9. Changes in Track placement as a foot rotation can also be used in countering ACM torque, as recently observed by Oscar Pistorious (an amputee runner with artificial legs made from flexible staves, as the Cheetah Flex Foot product," aka 'The Blade Runner'), making Olympic 2012 history, by placing $2^{nd}$ in a qualifying 400m race.

On the other hand, the Track metric can be estimated by the uniformity of the foot path placement estimated from the calf rotation swing component when the gravitational vector angle is aligned with the shank angle at maximum pressure during the TO part of the gait cycle. Together with balance, and the temporal identification of the eight-component, time periods of the gait cycle, a continuous estimate of Track and Balance can be made, based on synchronized MEMS sensor data estimates from the sleeve pair. However, the efficiency of Balance and Track can be estimated using the Lagrangian energy and force measurements for each sleeve, based on the space-time changes in the relative two interaction force vectors (G, A) detailed in Equation L3 for the Lagrangian energy (L), and the EOM for the torque vector (t). The definition of L is given in FIG. 10, which also shows variation of KE and PE components in walking (FIG. 10a) vs. running (FIG. 10b).

Figure 11:
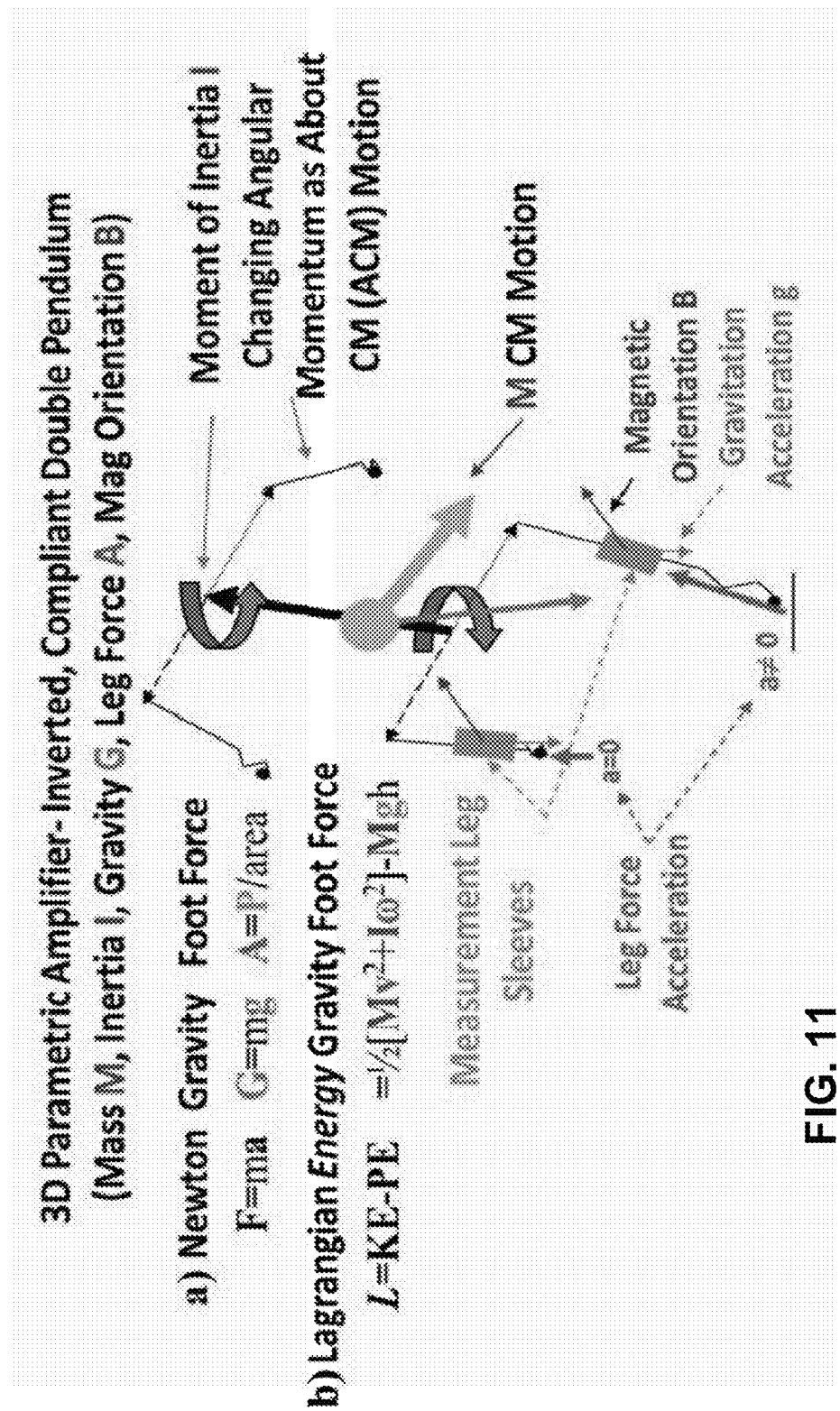

A more detailed description in the force diagram is shown in FIG. 11 for Newton (FIG. 11a) and Lagrangian (FIG. 11b) descriptions. Here, the KE and PE terms in L are defined with the inertial moment of ACM dynamics (a is the acceleration of the reactive force A on the mass M), and the coupling of the ACM to the CM forward translation is represented in a twisting motion from the upper body limb cycles, connecting through the spine to the lower body pelvis, where the limb swing lengths are pumping energy into the dynamics, as a parametric amplifier. This correlated energy transfer in time is an integration of the Lagrangian energy (Action), used as an efficient form of energy transfer for making the applied force change body limb positions in locomotion (Work), defining the muscle efficiency as an algorithm using PST data discussed next.

Action and Work Using Balance and Track Representations

Figure 10:
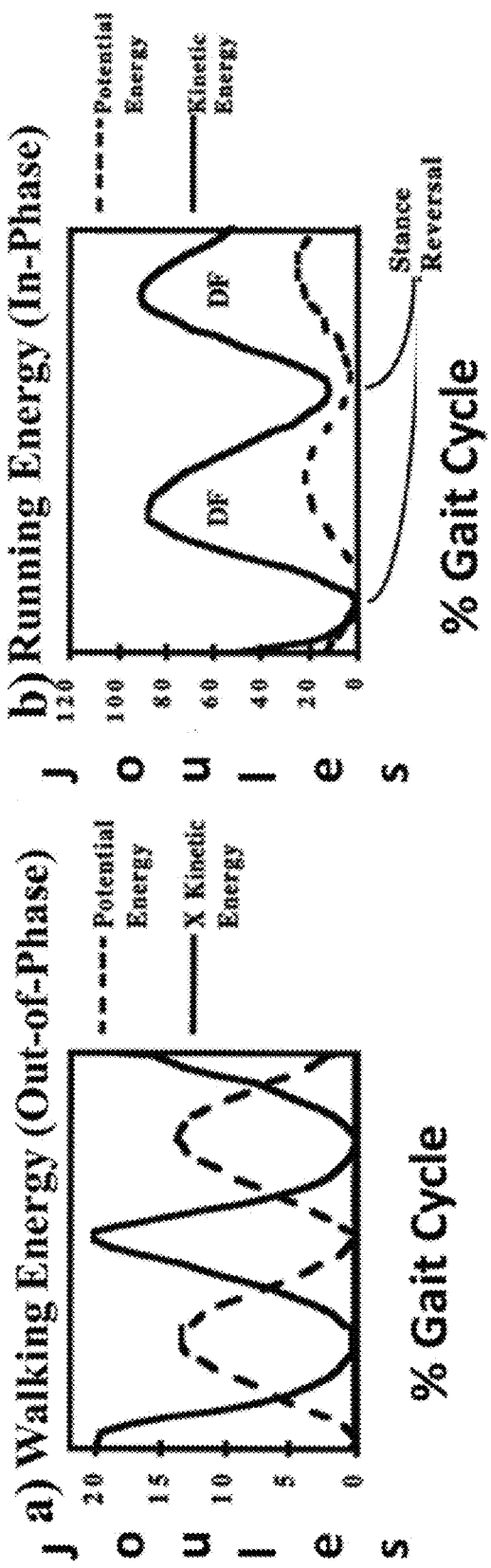
FIGS. 10a and 10b define the Lagrangian Energy, with KE/PE Changes During Gait Cycle Relative to Phasing Differences in Walking and Running FIG. 11 Shows Both Newton Force and Lagrangian Energy Descriptions in Balance and Track Dynamics of Modeled 3D Oscillation.

The description of the Lagrangian in FIGS. 10 and 11 indicate that the dynamics of the locomotion with the upper body motion during the stance and swing phase transitions will have a major impact on the Balance and Track, through the transfer of angular momentum. There is also a utility in this representation, to estimate the Action and Work, defined in the equations below, using the gait cycle representations of FIG. 2. Here, Action (A) integrates L over time, in synchronous timing with the gait time periods shown for the five time points of FIG. 2 (t1, t2, t3, t4, t5). Note that the integrations interweave the L for the total body dynamics of both lower legs, and achieve a representation of the forces for Balance shown in FIG. 9b. Also shown below is the definition of work (W), being the integration of the two vector forces, as separate components in the sleeve measurements, being integrated over the vector dot product of the infinitesimal motion vector direction, dx, with the velocity v estimated from the time derivative sampled integration of velocity (v=dx/dt). The vector integration with a dot product ("•") to dx, is between the stance steps (stationary foot placement in Track), thus allowing for a negative sign between the two components, implying that the A and G vectors are in balance in a double support stance (FIG. 9b) without much forward motion, and are within the changing integration dynamics between the three steps (x1, x2, x3) in the swing phase (FIG. 9a), in a singular support stance (L in x2 to x3, R in x1 to x2).

$$\text{Action} = \int_{t1}^{t5} L \, dt \approx \int_{t1}^{t4} (KE_{Right} - PE_{Left}) \, dt + \int_{t4}^{t5} (KE_{Left} - PE_{Right}) \, dt$$

$$\text{Work} = \int_{x1}^{x3} G \cdot dx - \int_{x1}^{x3} A \cdot dx =$$
$$\int_{f_{B(x)}}^{x3} (G_{Right} - A_{Right}) \cdot dx + \int_{f_{B(x)}}^{x3} (G_{Left} - A_{Left}) \cdot dx$$

Within this frame work of balanced Action and Work, one can compute the locomotion efficiency of the Action being minimized under the Principle of Least Action. In the example of walking and running shown in FIG. 10, the out of phase requires a minimum energy lost in the stance exchange between double and single support, and is more critical in the stance reversal region indicated on the right side of the figure.

This review describes how computational modeling can be combined with noninvasive gait measurements to describe and explain muscle and joint function in human locomotion. Five muscles—the gluteus maximus, gluteus medius, vasti, soleus, and gastrocnemius—have been indicated to contribute most significantly to the accelerations of the center of mass in the vertical, fore-aft, and medio-lateral directions when humans walk and run at their preferred speeds. Humans choose to switch from a walk to a run at speeds near 2 m/sec to enhance the biomechanical performance of the ankle plantar flexors and to improve coordination of the knee and ankle muscles during stance. Muscles that do not span a joint can contribute to the contact force transmitted by that joint and therefore affect its stability. In walking, for example, uniarticular muscles that cross the hip and ankle act to create the adduction moment at the knee, thereby contributing to the contact force present in the medial compartment. Many of these muscles are sensed within the placement of PST sleeves on the limbs.

The example systems and methods described in this application relate to the automation of the general field of determining mammal locomotion metrics, from a simple viewpoint when muscular-driven support members propel the body, being that of linear momentum relative to the ground or other surfaces, defined as Track-movement, and being that of angular-momentum relative to the body, defined as Balance-movement. This is uniquely different from gait analysis because these measurements are made by totally self-contained, strap-on-bands that can be worn in any type of locomotion activity including sports, and also by other mammals, such as horses, and does not require human analysis of any collected data. The example systems and methods incorporate band sensors worn on body limbs with networked RF connectivity to compute, using related sensor data and fundamental physical models, muscular motion across multiple band links and within a group of interacting sports players or racing mammals.

The particular sensing described in these measurements relate to the efficiency-of-retaining a Balanced-action of the upper-body angular momentum during Track-movement, which switches between the two lower body limbs, where previously A is defined as the temporally integrated, expressed Lagrangian energy, and also in the efficiency-of-moving the limbs forward during the placement of the foot, as a work Track-force. Here, W is defined as the actual force being integrated, over the spatial transition-distance of the limb, being moved between the forces of gravity and muscular applied thrusting and extending forces (A), as measured by the combined band sensors worn on the body limbs, being applied for the next periodic track foot-step. Because this real-time measurement and monitoring is being made with a very high fidelity, and is made outside the laboratory in the world of more natural activities, the Track and Balance motion viewpoint allows the measured information to be used in physical and mental health assessment. The metrics are in a database format for easy long-term trend analysis and population demographic characterization. Examples include use in sports training, in therapeutic injury-recovery monitoring (e.g., from either a predicted potential-injury diagnosis, or form post-disorders and post-injury repair assessment), and in general health care and treatment of the elderly. This discussion follows, with a focus on the unique viewpoint of Balance and Track, within the previous discussion of typical Gait Analysis.

Gait Analysis—Placing Feet on a Track

The mammal process of upright locomotion has been characterized for decades with gait analysis using measurements from feet striking force plates during video recordings, being made in simplistic dynamics, such as walking on a treadmill. The physical modeling of forward locomotion is part of biomechanics engineering, using complicated muscle and bone structure anatomy with Newtonian force interaction representations, to characterize the changes from standstill, to walking, running, and sprinting (at maximum speed), by creating a lower body activity, step-sequence of right (R) and left (L) foot placements used to make a Track. As is well known from early horse racing pictures, running is defined as having periods where all feet are off of the ground. The motion is of the body mass center, rising and falling in a periodic cadence between the R-foot on the Track in the stance phase, and then the Balance of the upper body, to transfer the body mass weight to the placement of the L-foot on the Track ahead of the first step. A final transfer of weight back to the R-foot with a second step completes the two-step gait cycle in time, as a stride of stride-length, at a speed, defined by this length and time, within a two legged, spatiotemporal correlation. These descriptions of Balance and Track use an analytic representation in Lagrangian and Newtonian representations for the physical modeling.

The foot placement track dynamic shown in FIG. 12a, is similar to playing with an inverted toy paddle ball shown in FIG. 12b to make an analogy, as a two-step gait cycle of stance shown on the right side in FIG. 12c:

Track is the motion sideways, in position of the paddle and in angle relative to the normal gravitational inclination, and Balance is the ball position relative to the center point directly above the paddle.

Gravity is the force applied by the rubber band in pulling the ball down to the paddle, and the foot-thrust to move the body mass to the other foot, is the paddle hitting force that drives the ball back up into the air. The shadow of the runner's feet positioning in FIG. 12c shows only one, stance foot touching the ground, and the other foot is in a swing phase off of the ground.

Efficient motion is when the ball stays in one position moving up and down in a linear periodic motion directly above the paddle, using a biomechanical model of an inverted pendulum component during the stance phase, oscillating periodically from the ankle/foot-toe, static position. With the knee also being a recognized joint in this modeled motion, this is called a double inverted pendulum. Finally, because the foot placement of the body weight acts like the absorption of motion momentum in compressing a spring when striking the Track, and the re-generation of this absorbed momentum acts like the release of the compressed spring's energy, the model includes a spring for absorbing and generation phases of momentum under conservation. This action creates a change in the circumferential pressure of the calf, which is measured with the PST sleeves, shown as an inset to FIG. 12a (and FIG. 3a), where each calf has a circumference-closure band, and the multiple MEMS pressure sensors are sensitive to individual muscle group expansions/contractions. The change, between stance and swing shown in FIG. 12c, is as if a second paddle hit the ball back into balance, thus indicating the importance of the momentum transfer by the swing phase foot placement for the next track position for stance. Note also that if the paddle is tilted relative to the gravity pull straight down, the ball will be moved out of balance, and can only be corrected by the next 'Track paddle hit' at an opposite tilt.

An informal analysis of human locomotion is to compare the differences between a baby crawling (all four limbs making tracks) and a football player running (usually with one or no feet on the ground). Training humans to move more efficiently and to stay healthy has enormous benefits; in the PST, the goal in these two comparisons is to move in an upright stance at a faster, safer pace, where the sleeve leg pressure measurements are translated into how one moves, and for professional athletes, effected information is from measured changes in hundredths of a sec increments. Inefficient movement develops fatigue, creating stepping errors, inviting a poor cadence in stepping that is an unbalanced motion. This can create injuries; hence, the desire to move upright vs. the inevitable action of falling down.

Thus the human cycle of forward motion is about the dynamics in daily life, through exercise and sports, where dynamic errors cause injuries and out of the ordinary changes can be precursors of mental changes too. The locomotion of placing feet on the ground to move forward is the historic "1 sec" gait cycle, measuring pace, cadence, step-length, step-rate, speed, and stride-length, where improper dynamics have an inefficient gait. The PST is making a unique and previously unavailable measurement. An interesting way of understanding these changes is to look at images of humans in activities with zero, one, or two feet touching the ground:

TWO FEET Extended force—When stationary, we stand on two feet, or transfer energy between feet when moving or swinging a club, racket, bat, etc. for applying an extended body force, which in many instances, this applied force is while on one foot, in such sports as tennis, golf, cricket, lacrosse, baseball, hockey, etc.

ONE FOOT Changing mass direction—The Newtonian physical modeling relates the "hitting" force (F) while moving to creating changes in the mass (M) direction, as an acceleration (a), which in turn reacts back as an unbalancing force to the human dynamics; this is where the Balance is perturbed, and thus perturbs the Track when the feet return to the ground.

ONE FOOT Applying pushing force—The return of one foot to the ground must include a landing of the body force, combined with the angular momentum carried through the limb contact, which is usually referred to as a turn, cut, etc., which changes body motion direction as an extended, "pushing" force to keep balance with tracks in a new direction. Here, basketball, football, soccer, rugby, and other contact sports involve extending forces through the body to catch balls in the air, push balls in the air towards a hoop or another player, or change direction to avoid another player.

ZERO FEET Regaining Balance on return to ground Track-Finally, there are body dynamics of being without any ground contact, such as throwing a ball while in the air, aligning the limbs after leaving a ski jump, or maneuvering on a snow board in the air, which all create a change in angular momentum of Balance, which must be transferred in an unknown manner back to the Track upon contact with the ground.

Even video action garners, jump and move in simulated action environments, and elderly walk and run in low contact environments, with a muscle control being guided under a brain dynamic of requests to engage multiple muscles in creative unity of purpose. These actions benefit from Balance and Track measurements in enhancing the body dynamics to the game feedback, or to monitor the body dynamics for internal mental changes in health.

Gait Analysis—Swinging Feet in Balance

Just as important in the gait cycle of the stance phase, is the other, lower body action, which "magically" moves the back foot off of the Track, and places it ahead of the other foot in the stance phase, just in time before the upright mammal falls over as the transfer of weight in the stance phase begins again. This is the stance compliment phase called the swing phase, which is not periodic, and is referred to as being "aperiodic." While it is easy to refer to this as meeting a physical argument of conservation of upper body angular momentum, the swing phase is anything but a simple, nonlinear action, and is not only not well modeled, but it is also not well measured in the video gait analysis sequences, because multiple cameras are required to describe the 3D motion of the swing leg as it moves back to the stance phase.

Current wearable devices used in gait measurement and recreational activities produce simple data recordings of external force applications, analyzed along with video by a human, to infer characteristics of orderly body limb movement and symmetry, using extensive biomechanical simulation models, but generally without any internal force sensing. The sleeve described herein is used in pairs that correlates motion of both feet through the entire gait cycle and provides information on Balance efficiency in the use of energy dynamic transfer as Action and in Track placement efficiency using the angular momentum of the upper body Balance as Work in lifting and placing feet. An important element of Balance & Track, is not just the stance phase, but more importantly in the swing phase, used to adjust the momentum to reduce force errors from the GRF in re-establishing the next Track.

Sleeve Information Integrated from Pressure Sensor Measurements

A key point of the developed sleeve is the manner in which the human locomotion utilizes energy in achieving efficient work within the gait cycle. This replaces conventional, external gait metrics of force plate data, video cameras, and biomechanical models, with onboard the body, energy and force information from Action and Work computations. Here the gait cycle is just a model of what really happens, to better categorize what is measured with the sleeve sensors. The points for integrated sensor data measurements to produce informed guidance and monitoring requires a precise segmentation of the data as follows:

Gait dynamic characterization exists between a two-step, L-R-L sequence of three-ICs, as the gait cycle, with units of:
1. Gait Speed (time to walk at preferred/quick speed for 20 ft), varying with age (20's to >80's, or frail) and sex from 1.18/1.97-3.57/6.4 (ft/sec) for men and 1.38/1.57-3.47/6.43 for women.
2. Stride-length (1.5 m), step-length (L-heel to R-heel), step-rate (120 steps/min, which is an average speed of 1.5 m/sec stride-rate) are various distances and clocked time as measured by calibrated photographic recordings of IC placements for a set of footsteps while walking and running, usually performed on a treadmill.
3. Three beat, two-step sequence as a cadence in stride, related in mammal locomotion to oxygen uptake and fatigue, with optimal locomotion efficiency, being most efficient at a moderate walking pace.

PST mammal dynamic information, with units of:
1. Balance symmetry averaged over multiple gait cycles as a continuous information output derived from cross leg-stance asymmetric behavior.
    Two-limb correlation analysis for locomotion information
    Optimum conservation of angular momentum in Balance
    Inefficient and abnormal in Balance is asymmetric, or un-Balance
    Track footpath placement errors must be corrected by the swing back to IC, for 're-spinning' the angular momentum wheel, to be in synch with Balance
2. Stance and swing as smooth transitions between periodic and aperiodic muscle pressures derived from lower body muscle force exertion and relative L to R muscle correlations.
    Sleeve pressures in calibrated sensors change about a mean value between stance and swing phases of cadence
    Periodic and aperiodic time periods have statistical discrimination, with individual gait cycle corrections for Balance, and efficient foot step placement to maintain efficient Track
3. Periodic and aperiodic dynamics of cycle change forces and energy use effecting locomotion efficiency.
    Muscle forces change during moving limbs in gravity over distances producing work (W) as the lower body muscles lift and swing the legs after thrusting (A) during TO leaving the supporting gravitational force (G), and StR/SwR absorption/generation of linear momentum (spring in the inverted pendulum).
    Work integrates the force over spatial distance in moving the feet into producing tracks as a Work-Track from (A-G) changes (misaligned vectors have less work from the reduced, projected aligned component).
    Action (A) integrates the Euler-Lagrangian energy (L), from the difference of the kinetic energy (KE) and potential energy (PE), as L=KE-PE over time, where the KE is derived from the mass center, linear dynamics such as forward momentum, and the other mass center nonlinear, angular dynamics, such as angular rotation of upper body inertial momentum, and the PE is derived from the potential changes in gravitational height of the mass center bouncing up and down through stance phases.

Minimizing the use of L energy is an optimization goal to have efficient transfer between linear and nonlinear dynamics (Principle of Least Action), while also minimizing the action (+L) and reaction (−L) over multiple gait cycles, where the work is reduced with balancing foot thrust forces as push-up directions, with gravitational forces as pull-down directions.

The interchange between Balanced-Action making efficient Work-Tracks, is controlled at cognitive and muscle memory levels, but also involves feedback from skin sensing of blood flow and muscle pressure, such as the reduced pressure during the swing phase of the leg. This is an efficient sensing channel not obvious in biomechanical models and is the essence of efficient locomotion.

4. The example sleeve described herein incorporates the spatiotemporal analysis of sensor measurements in correlation between paired limbs in the lower body, and/or also in the upper body, but at a minimum it is with the L-Calf and R-Calf sensing, with RF links used to correlate the individual work and the Action computations shown next.

Figure 13:
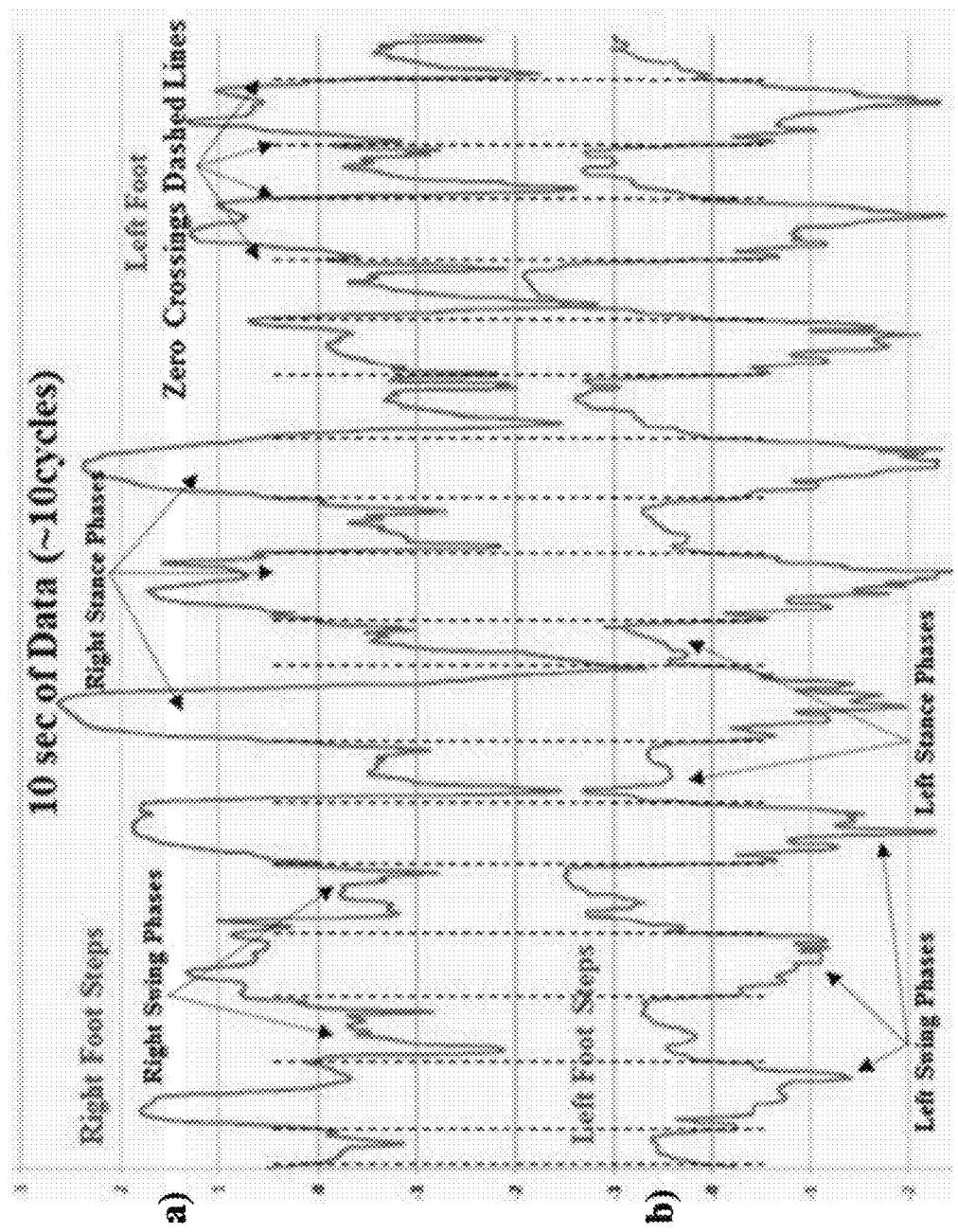
FIGS. 13a and 13b show Earlier PST Data for 10 Sec of Correlated L-R Leg Muscle Pressures in Stance/Swing in Normalized Zero-Value, 10 Gait Cycles.
Figure 14:
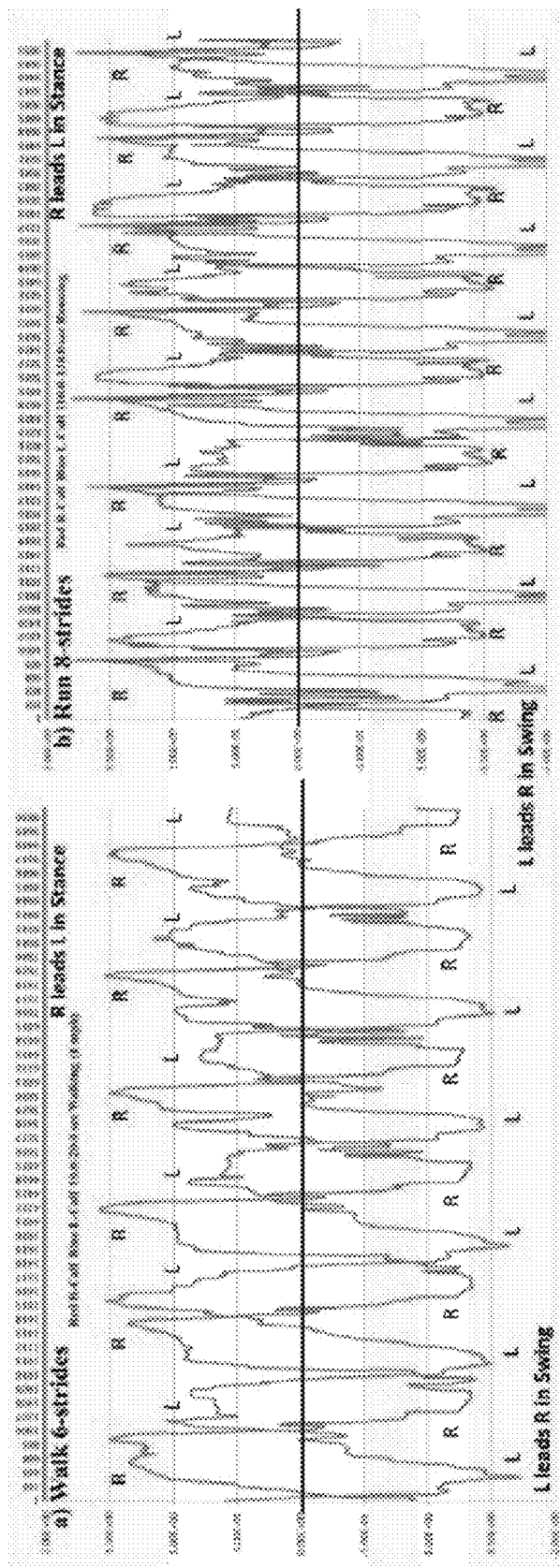
FIGS. 14a and 14b show Correlated Running Pressure Measurements for L-R Calf Pressure in Walking (10 sec/8 cycles) and Running (6 sec/8cycles).
Figure 15:
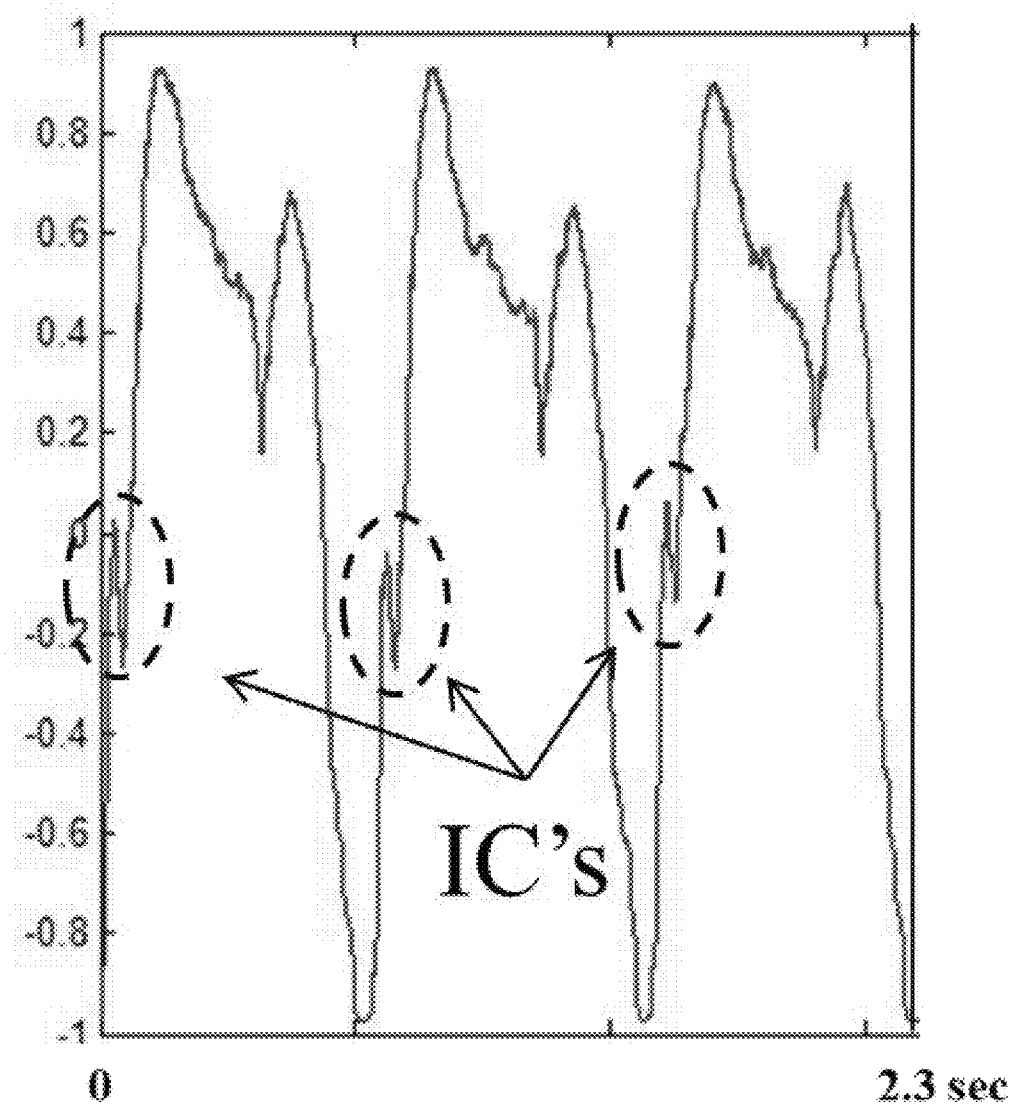
FIG. 15 Shows PST Pressure Sensor Improvements from Earlier Designs with Continuous Flow and Distinct, Reproducible Events (2.3 sec).

PST Action and Work Correlated Computations, where the KE of the swing and thrust gait components and the PE of the stance double support periods contribute to the Action, and the Work is being measured during the singular support stance while moving the swing in a limb motion against momentum and gravity. Example data is presented in relative units of circumference pressure scale change, after scaling of the raw data. Note the following individual and correlated limb discoveries:

1. FIG. 13 for 10 sec/10 cycles of calf pressure data, being shown for both Right (FIG. 13a red color) and Left (FIG. 13b blue color) calf's sleeves, here with:
    Vertical zero-crossing dashed lines delineating the stance phases (rounded sine wave top, pointing up, as rounded peaks more typical of GRF data), and
    In-between swing phases (pointing down, as valleys with more pointed bottoms), as cyclic below the FIG. 13a data, which also correlate with the Right gait phase delineation. The double-hump in the stance is paired with the pointed valley in swing by the opposite leg. Sometimes this pattern is such a 'mirror image' pattern, they seem subnormal, yet this is a similar observance.
2. Another example of correlated data is shown in FIG. 14, with letter labels on valleys (swing) and peaks (stance), for R-leg in red color, marked with "R's," L-leg in blue color, marked with "L's," shown for walking at 1 mph for 10 sec (6 cycles, FIG. 14a,) and running at 5 mph for 10 sec (8 cycles, FIG. 14 b).
    Note the 'double support' of both legs in stance by the crossing of the traces above the mean in walking, and
    Note how the faster running has self-synching of the swing, to very precise valley 'ticks,' while the peaks are moving relative to each other in time location and amplitude.

Figure 16:
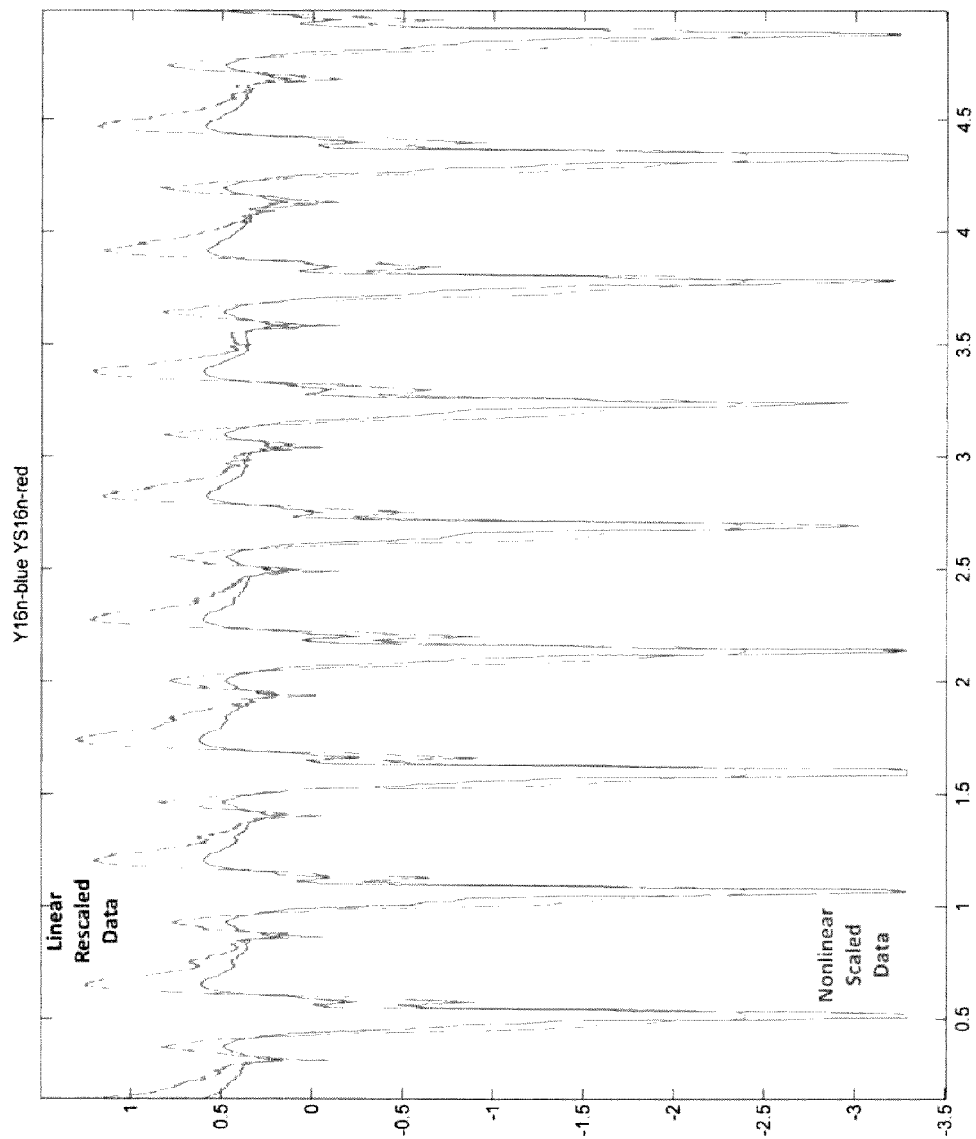
FIG. 16 Compares Nonlinear Scaling to Remove Electronic Distortions of High Fidelity PST Measurement of Gait Cycle Dynamics (8.3 sec).
Figure 17:
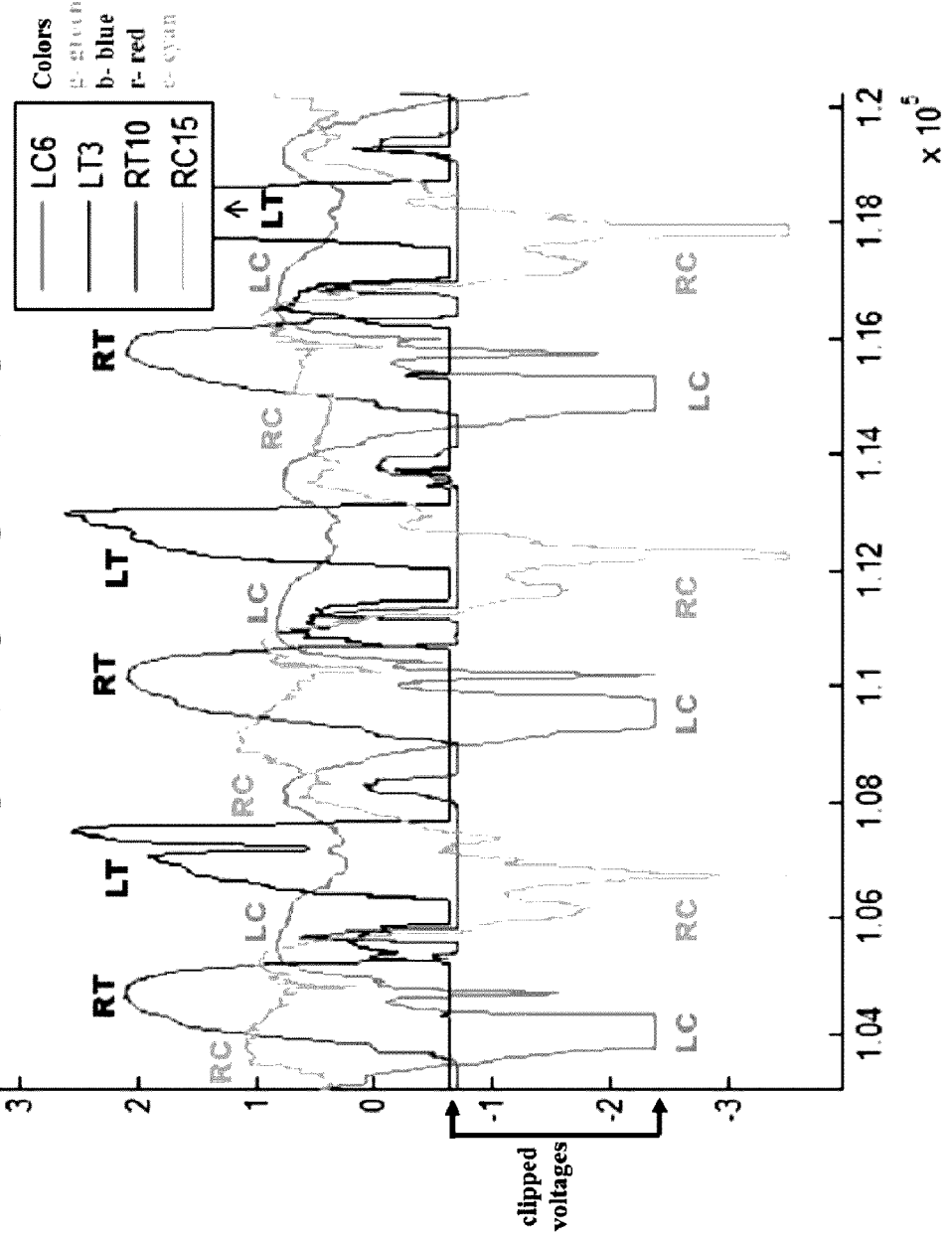
FIG. 17 Shows Four Pressure Sensor's Data, Correlating over All Four Lower Body Limbs, with Replication of Individual Muscle Patterns.

Sensor Fidelity Improvements, included changes in electronics, fabrication of sensors and materials, and placement within the sleeve, allowing for an inherent impulse response at <1 msec. Examples include:
1. Improvements shown in FIG. 15 for a 2.3-sec/3-stride example has increased pressure sensor fidelity, with IC events marked with a dashed circle, which varies slightly in position in walking, and a
2. Re-scaling (red color, upper curve) of this high fidelity data in FIG. 16, shows an improved linear dynamic range. Here, the trends of the stance upward peaks and the swing downward valleys are very precise for the peak and valley time periods, arguing for a 50%/50% swing to stance peak time ratio, except at the zero crossing, the ratio in time is more typical at 23%/70%.
3. More simultaneous sleeves, are shown in a further example of 16 channels of correlated, limb muscle pressures, shown in FIG. 17, for 2.8 sec/3 gait cycles of data; some data was truncated in the sampling as a clipped voltage); hence, only four muscle-aligned, channels are plotted, noted by limb type and board number abbreviation listed in the title.
    Note that the thigh data of FIG. 17, has dominate singular pressure increase from lifting of the lower calf limb during the swing phase, shown being paired with calf data (numbers indicate which MEMS module is measured, i.e., LT3 with LC6 for left correlation, and RT19 with RC15 for right correlation, with thigh leading calf swing.
    Note the correlative alignment of the thigh and calf (RT lagging to LC in swing; LT lagging to RC in Swing; RT and LT in precise periods on falling edge; LC has an amplitude offset artifact that reduced the stance and truncated the swing; RC has a stance peak reduction with subsequent cycles; RT and LT have trailing, secondary peaks.
    Note also there are individual changes in the stance (and thigh lifting phases, during the swing data), which will be corrected with improved electronics in data sampling, described later.

Figure 18:
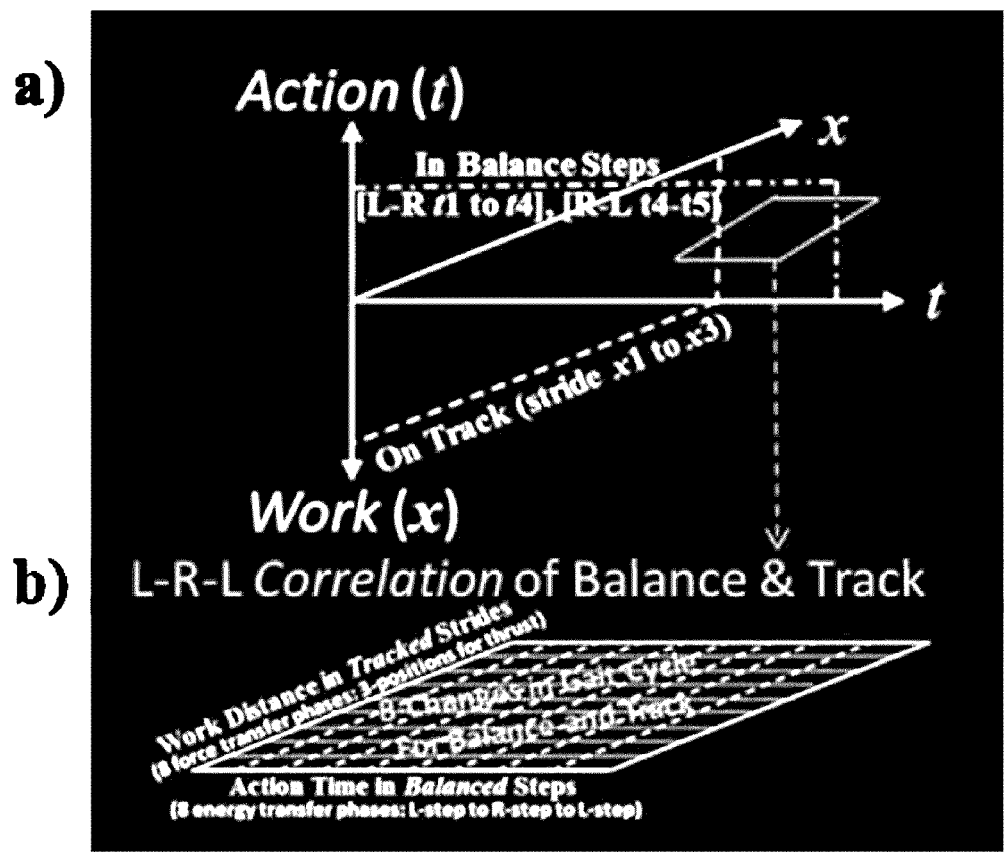
FIGS. 18a and 18b show Modeled Action & Work in 3D Plotting Alignment, as Stride Correlation of Balance & Track Driving Action & Work.

The elements of Action and Work are correlated as well, shown in a model representation in FIG. 18 as a 3D (XYZ) function in FIG. 18a, where the temporal space of the Action from the Lagrangian energy (t-axis along horizontal X-axis, with values along the positive "Z-axis up"), is correlated from the spatial integration of the Work forces of G and A (x-axis along the "Y-axis into the page" with values along the positive "Z-axis down"). Here, in FIG. 18b, the correlation is computed within this overlapping region shown for the 8-cycles of the gait model, but in reality this is just determined by the time change detection synched with the spatial changes. The plot of expected PE and KE in FIG. 10 for running going to zero at Stance Reversal, StR (i.e., L=small+L, 0, or small −L), argues for the ACM dynamic switching to conserve angular momentum at StR.

In the earlier FIG. 14, the walking and running L-R calf pressure correlation examples have considerable peak synchronization, despite the individual gait cycle variations along the stance and swing correlation. A key distinction shown between the walking and running example, is the more precise alignment in the swing phase of the pressure data during running, with very reproducible patterns. On the other hand, the walking data seems to show examples of inter-stride correction of the stance phase pressure useful in retaining Balance, due to L-calf irregular stance pressure causing a correction by the following R-calf sequence of very fast off/on force changes (as short dips during the stance periodic cycle). These data imply the very important use of the swing phase in Balance correction, allowing for regular cadence as a fine tuning governor of an engine, with the stance phase having less importance to the gait cycle details, but can provide the 'course' power engine in locomotion to overcome changes. In a sense, these data are "finger prints" of the individual's locomotion, and can be retained as PST provides Balance and Track information for chronological database monitoring. These details are made more apparent in the correlation of Action and Work being applied to this detail through the computations indicated in FIG. 18.

Detailed Metric Application for PST Data

Figure 19:
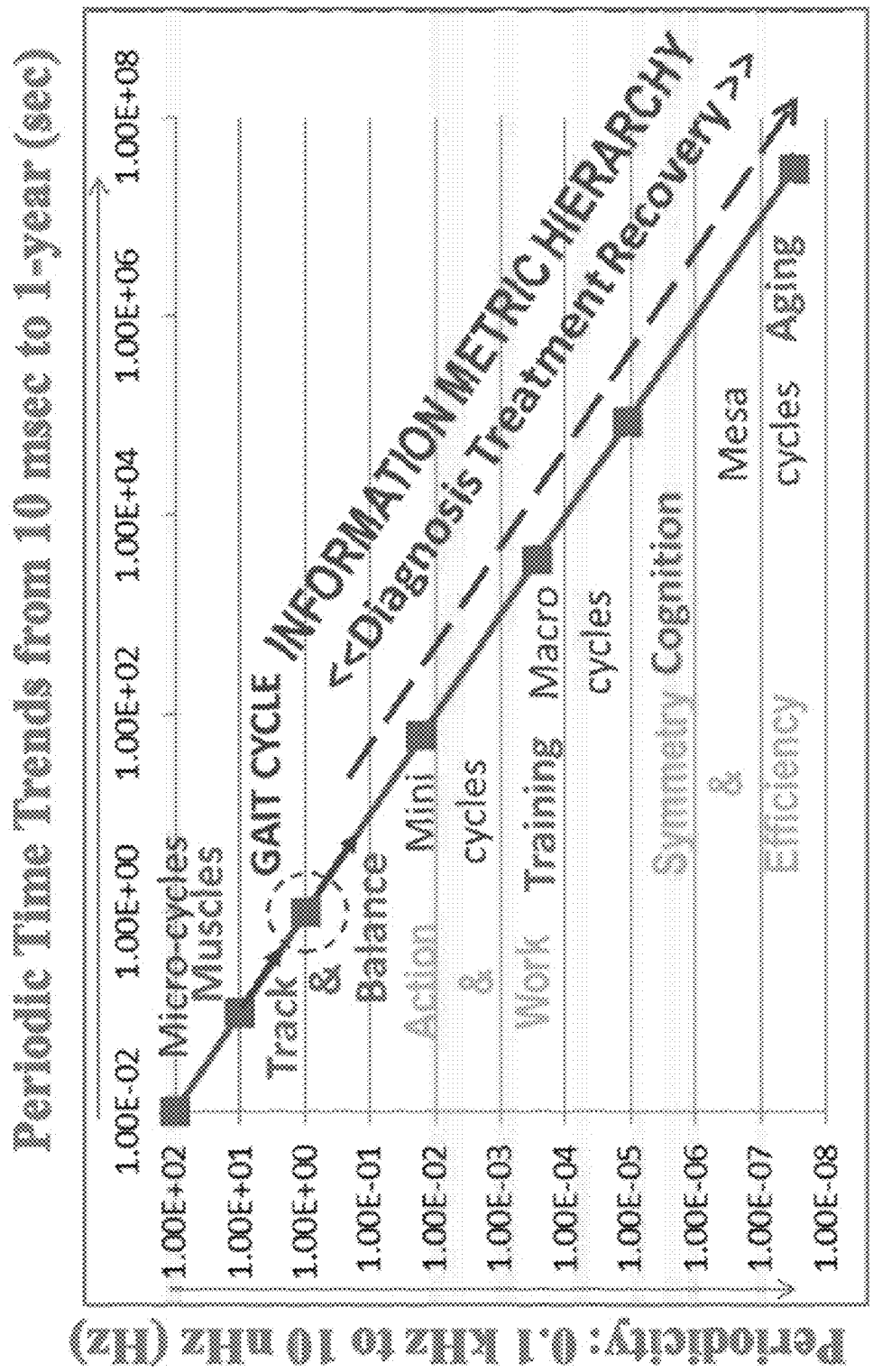
FIG. 19 Shows Frequency of PST Events Relative to Periodic Time Trends (Micro to Mesa as 10 msec to yearly).

The concept of using PST in a variety of data collections and analysis over a variety of time scales, emulates from the definitions of locomotion within standard gait cycle modeling, and the human cognition and muscle memory neurological processes, as used in psychological and physical therapy (PT) modeling. The standard gait cycle consists of two major phases for each lower body leg, being either stance or swing phase for one or the other leg, with a short time spent in double leg support. Within this cycle there is a two-step stride process for the L-step to Right-step, and then back to Left-step. This basic time scale is on the order of 1 sec (1 Hz) in standard walking, with four components each as complete 8-period locomotion for the two phases. There are also possibly more than TO and IC sub-gait time event components, e.g., the roughly 10 msec IC events in FIG. 15 for three strides, being on the order of 100 Hz data sampling required for sufficient representation of detailed representation. However, there are both locomotion scales below this standard scale, being on the order of sub-msec sampling as a micro-scale (e.g., kHz) as seen in EMG neural muscle measurements, and a global, or macro-scale, being over a few strides for an average locomotion assessment of over 10 sec (0.10 Hz). Thus, long term human Balance and Track motion as a diagnosis or training tool, on a scale of minutes, to hours, days, or even a year is required for all of the PST applications possible (i.e., 60 sec to 32 M-sec, or from 1E-02 Hz to 3E-08 Hz, as shown in FIG. 19). The "sweet spot" for this analysis is along the diagonal of five scales (Micro, Gait Cycle, Mini, Macro, and Mesa), with applications relating to fine details in locomotion, indicated in the figure as small time scale applications relating to the body Muscles, and then larger time scales relating Track & Balance, and on into Training, Cognition, and Aging. Action & Work correlation analysis is shown for the Mini-cycle scales, because it relates sequences of the gait cycle to longer integrations of B&T, and Symmetry & Efficiency are shown at the Macro-cycle scales, because they relate to longer periods between events on the asymmetry of the gait and the efficiency of the amount of Work produced from the Action of the Lagrangian energy. Here, a finer trend is of interest, and small changes must have significance in the longer term estimates.

Obviously, the variations in locomotion analysis over this micro to mesa scale of FIG. 19 covers ten orders of magnitude in time and frequency, which is unusual in normal human analysis, as this is equivalent to a gait cyclic period of 1.5 msec covering a distance of 1 mm to $10^4$ km (e.g., 5 km/hr for 2000 hr). The process of covering such a large output of data to analyze in an automated fashion is to analyze events of scale, based on the precision of the swing phase and stance phase reversals from FIG. 8 and FIG. 10 (StR, SwR), as measured in the PST examples. Beyond the sweet spot of the diagonal shown for the Gait Cycle, there is an ever expanding development over the trend analysis that creates an Information Metric Hierarchy, shown in FIG. 19 along the diagonal moving from Diagnosis applications to Treatment and then to long term Recovery.

Figure 20:
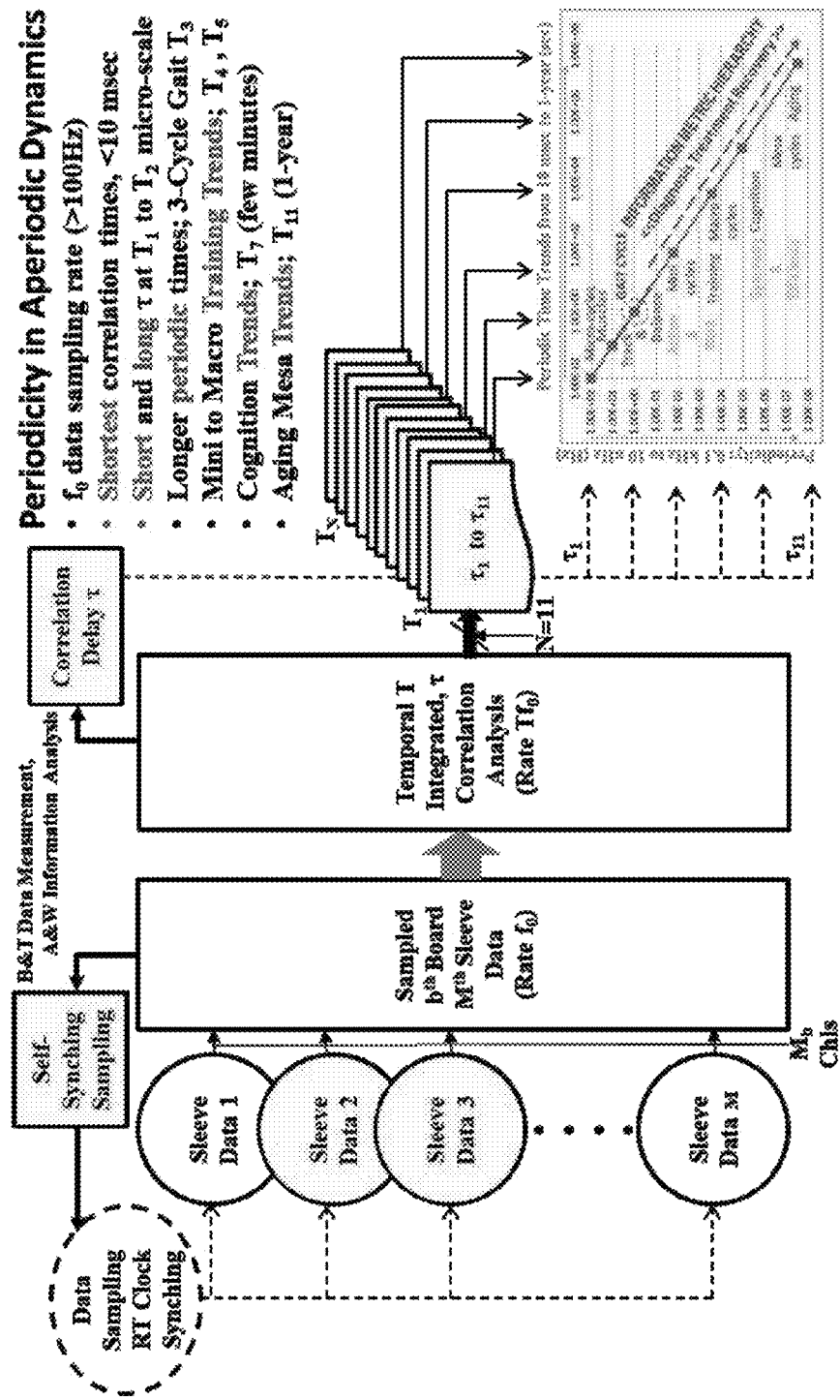
FIG. 20 Shows Multi-scaled Parameters for Applications Using Self Synching Sampling in Temporal Integration of Tau-Lagged Correlation.

FIG. 20 incorporates the scales of FIG. 19, into a sensor processing design for many different bands, beginning on the left side with a self-synching of the data sampling at a fixed data rate ($f_0$) across M sleeves having a unique $b^{th}$ board ID, for a set of many channels indexed as $M_b$ being feed into the first stage of the data processing. This process is output to the correlation analysis stage for time integration (T) at correlation lags (t). The parameters in FIG. 20 are set for eleven bands to cover the space of FIG. 19, and are set for a set of eleven lags within each of the eleven integration times, to cover the breadth of the trends, and are optimized for the diagonal, 7-11 sets shown on the right, lower side of FIG. 20. Specific parameter constraints are listed based on early data results.

Figure 21A:
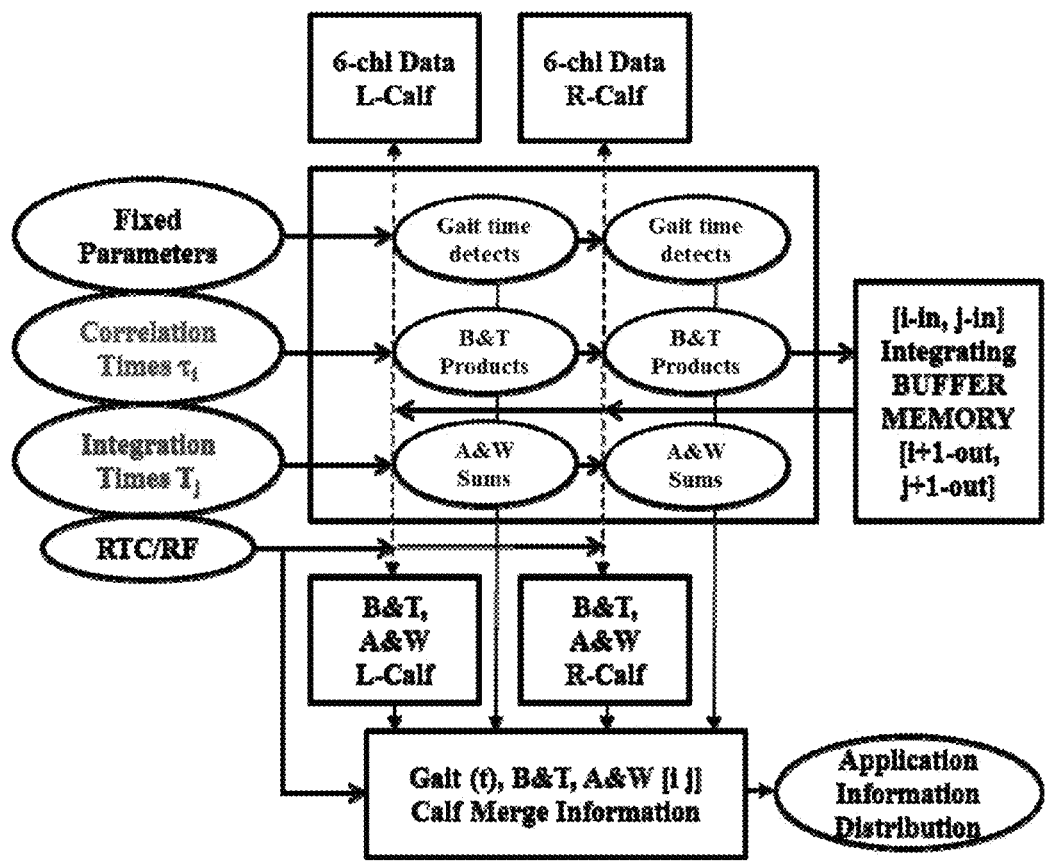

FIGS. 21a and 21b-1 through 21b-5 show the algorithm flow to process the data using the parameters of FIG. 20, as shown in FIG. 21a algorithms, and in FIGS. 21b-1 through 21b-5, examples of single calf pressure are shown that span examples of events from 10 msec, <300 msec, <3.5 sec, <100 sec, and >100 sec. In each of these scales, the data continues to show synchronized frequency dependence in the nonlinearities of the swing data near the valley, similar to a clock ticking, also shown in the spectral plot peaks and phase synchronization transitions. The algorithm that operates on this data set, shown in FIG. 21a, involves many orders in integration time and time lag correlation. The data examples shown in FIGS. 21b-1 through 21b-5 are better displayed and marked in two time trends of events for each scale, ranging from msec to minutes, using the swing "tick" sequential variations, and the stance peak ridge trends, as shown in blue, red, and brown markings. The algorithm is centered around the gait time period for event detections, using a real time clock in each sleeve (RTC) being synchronized with the RF communication exchange for minimizing errors in the cross/within channel correlations.

Figure 22:
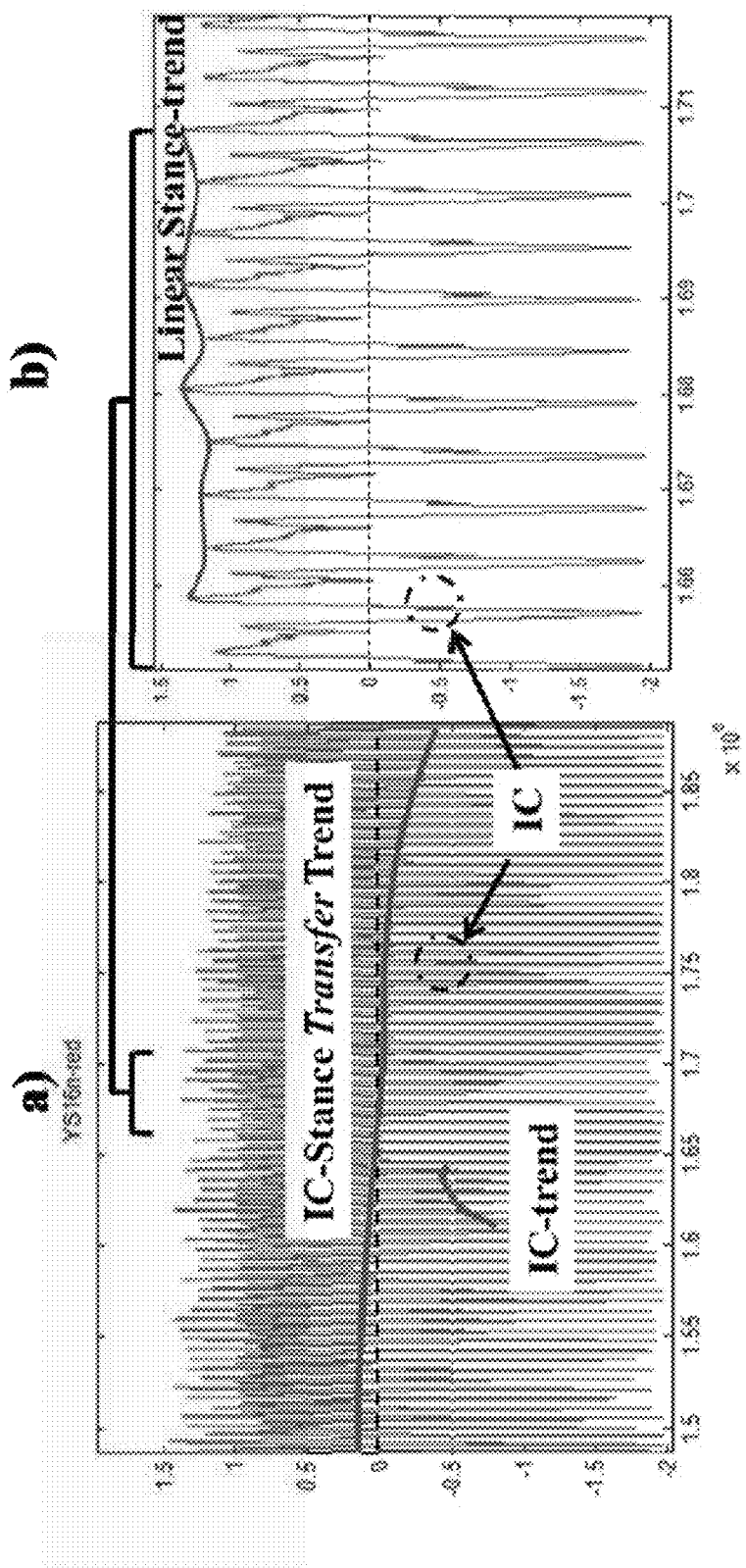
FIGS. 22a and 22b show Close-up of FIG. 21 Data Patterns in IC Trends of Swing and Stance Peak Levels (117 cycles).

With a parameter selection set for the diagonal setting in correlation and integration ($\tau_i$, $T_j$), the gait cycle events are feed into a parallel processing to compute the B&T products and the A&W sums as integrations in time and space respectively, with a Buffer Memory to facilitate a realtime output rate of this processing. In this case the channel set is based on a left and right calf set of measurements, which are then merged for distribution in various applications. A higher resolution of the last data example in FIG. 21b-5 at the bottom, lasting for over 10 minute trends, is shown in FIG. 22 in more detail, where the IC event and the peak and valley correlations are shown with trends over 100's of cycles in both stance and swing peak and valley changes (FIG. 22a) and still with an identification of an IC event trend (FIG. 22b) and peak stance trend. Product summary details follow.

Product Summary

Figure 23:
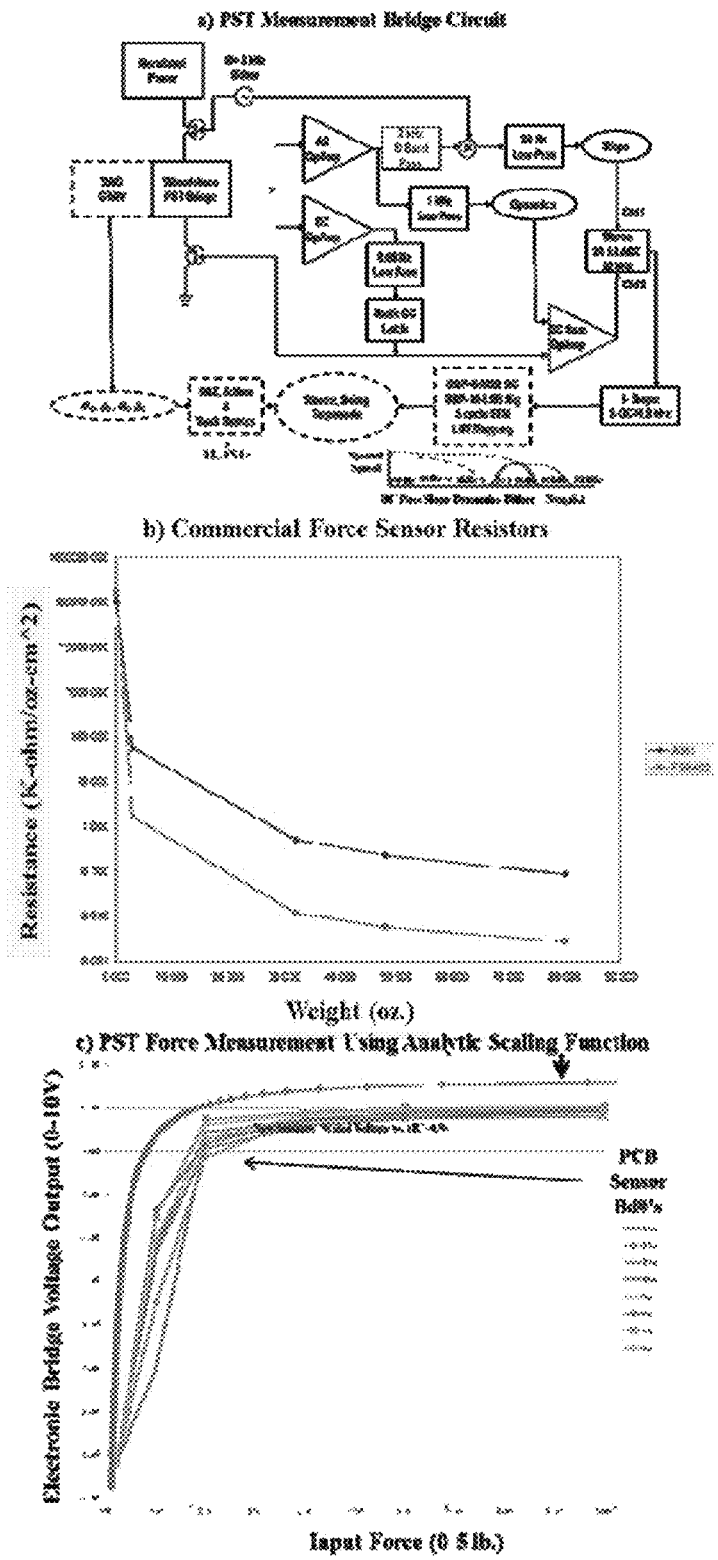
FIGS. 23a, 23b and 23c show a Notional Circuit Design Approach Using a 3-HF/LF Band Merge for 24 bit Accuracy in Pressure Feature Bands to 16 kHz, and Calibrated Data Scaling Using Analytic Functions.

The PST technology is based on a precise means of measuring limb muscle pressure concurrent with Earth's magnetic and gravitation field angular location, and vector acceleration on the body COG and linear momentum (CM), and angular velocity and acceleration of the inertia (ACM). The high fidelity of the pressure sensing allows for the many analysis scales of sampling to not loose long term trends, as would be typical in an averaging algorithm over periodic gait cycles. It is the aperiodic cycle of the swing events which creates this internal locomotion 'ticking' from both muscle and mental performance. Thus, the pressure sensor measurement circuit and analytic, calibrated scaling removes nonlinear outputs as shown in FIG. 23. FIG. 23a shows a Wheatstone and electronics design expected to further improve current fidelity dynamic range, and to operate at over 24 bits of data sampling at 16 kHz rates (vs. current 16 bits, theoretically going from 96 dB to 144 dB) along time variations within the three frequency bands shown (LF in 0.05 Hz, HF in 20-1 kHz, and HF in 2-4 kHz, at 16 kHz data sampling). The known problem in current Commercial Force Sensing Resistors, shown in FIG. 23b for translating force to resistance, requires an inverse resistance analog scaling (i.e., 1/resistance, shown as "R" in the figure) to remove this nonlinear effect (current commercial designs use a positive feedback circuit in the electronic operational amplifier circuits), but were shown to have an increase in electronic noise, causing current PST work to use a different approach. FIG. 23c shows an analytic scaling function used in software of the data processor shown in FIG. 20, and applied to data in FIG. 16. This function was determined with precise, calibrated sampling, established across a number of PST sensors and estimated to a R^-0.9 variation, to retain the PST sensitivity in a linear manner for precise swing and phase data computations.

Figure 25:
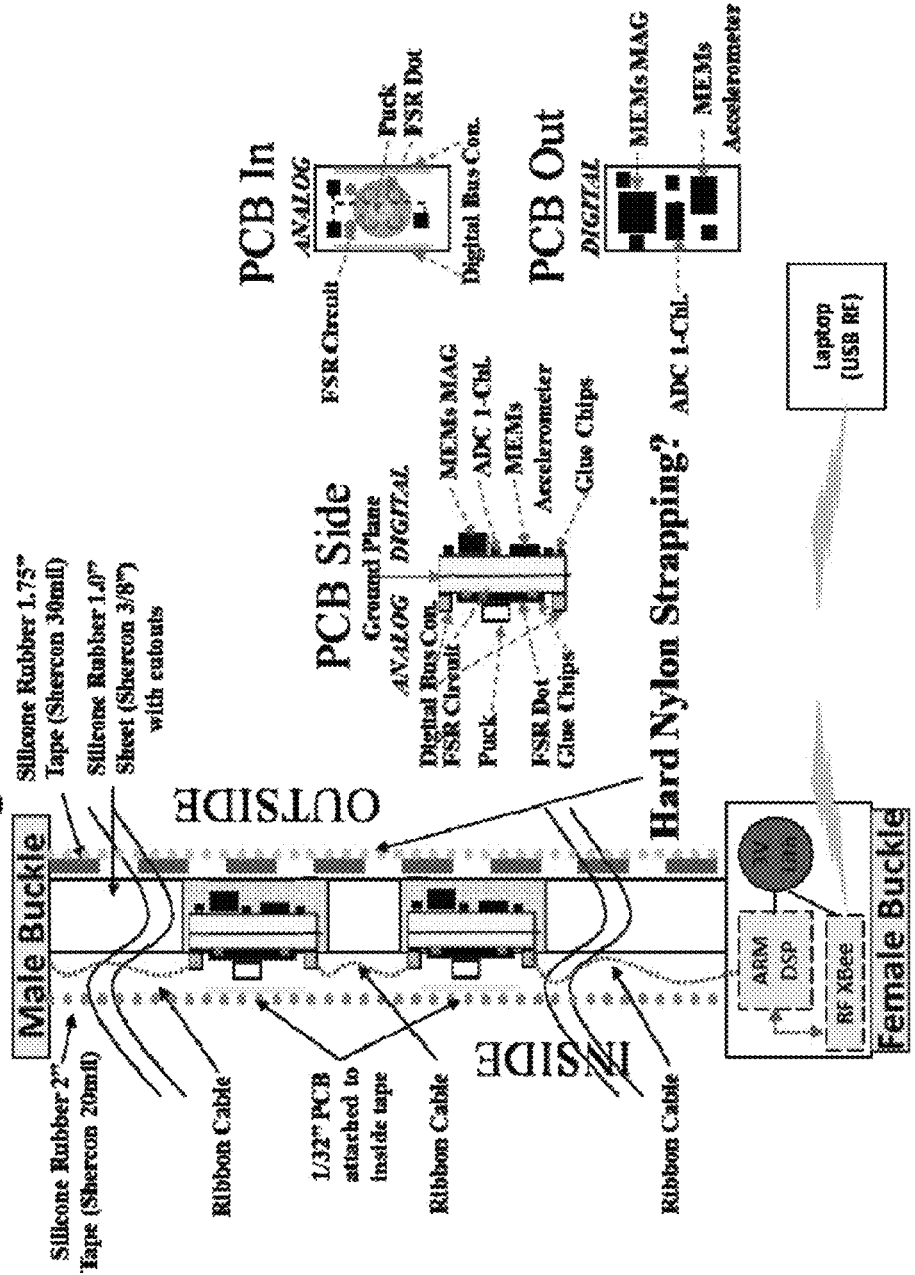
FIG. 25 Shows a Mechanical Design Used in a Preproduction Design for Sleeve Fabrication, Electronics, and Assembly.

FIG. 24 shows an example of a female model sitting in a chair in the upper left corner taken as sequence images from a video, attaching the preproduction sleeve to each leg and then standing up and starting to walk on a treadmill for testing. The images frame through the R-heel strike at IC through stance, while the left leg is in swing, and then the right leg goes through swing while the left leg is in stance, ending with IC to start the cycle over again. There is also an example of raw data shown on the computer screen, during data collection, with a single, 1-second of walking gait cycle data being shown for the right sleeve of five muscle groups similar to the data shown in FIG. 6. The lower part of FIG. 24 lists benefits of the PST in a product and various RF connectivity used by the individual, the trainer, and even the medical practioner, using the various product computation and display technologies that are used in the PST product applications. While the computing hardware will change over time, FIG. 25 shows a diagram of MEMS and PCB construction for an example sleeve construction and fabrication for comfortable sleeve attachment. The FIG. 25 sleeve band with multiple individual printed circuit boards (PCB) each integrating two 2D MEMs sensors with a single force sensitive resistor (FSR), being electronically measured with a circuit like that shown in FIG. 23a. In particular, the boards each include a magnetometer, a gravitometer (accelerometer) on an outer side and a force (pressure) sensor on the inner side. An adjustable buckle or Velcro strap tightens the band. The sensors are connected to a processor (e.g., an ARM digital signal processor), which processes the sensor signals for PST metrics of B&T and A&T, as well as typical gait metrics. RF communication is used for sleeve to sleeve communication for computing these metrics locally (e.g., Bluetooth (e.g., processor-USB to RF transceiver from Targus, IOgear, Sabrent), or using ANT+ (to a wrist watch, e.g., TIMEX Ironman), and for longer distances like to a laptop for example, using wireless communication to a computer via a radio module such as from the XBEE family available from Digi International, or a Qualcomm Life Internet link to the cloud.

Other example constructions for sensing the various parameters described herein are shown in U.S. Pat. No. 7,610,166 and U.S. Patent Publication No. 2011/0208444 (the contents of each of which are incorporated herein in their entirety).

Specific applications for the PST in some of the connectivity shown in FIG. 24 include examples of application users: for training in Professional Sports (5000 players in ball sports), Professional Horse Racing (5000 horses, not including instrumenting the jockeys and riders), ACL injuries in diagnosis in pre-Op and post-Op, treatment, and physical therapy (200K surgeries per year, with some being a repeat operation), stroke, back disorders, brain disorders, Elderly care, which has shown the first signs of dementia (i.e., cognitive model: brain commanding system function, muscle memory executes action-measuring muscles measures brain), including Alzheimer's disease, may not be a faulty memory, but problems with balance and walking, according to a new study by UWA, Group Health Coop, found senior citizens who participated were three times less likely to develop dementia if they maintained their physical function at high levels (total users at >10M), and all of the semi-professional, collegiate, and even high school for training and testing for predisposition in ACL injuries from gender (females have a worse Q-angle). The PST can be tailored for these applications with minor software changes, including for the long term analysis examples shown the trends of FIG. 19.

PST System Concept

The described systems, methods, and techniques may be implemented in digital electronic circuitry, computer hardware, firmware, software, or in combinations of these elements. Apparatuses and systems embodying these techniques may, for example, include appropriate input and output devices, a computer processor, and a computer program product tangibly embodied in a non-transitory machine-readable storage device for execution by a programmable processor. A process embodying these techniques may be performed by a programmable processor executing a program of instructions to perform desired functions by operating on input data and generating appropriate output (e.g., visual output, aural output, and/or tactile output). The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Non-transitory storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, speciallydesigned ASICs (application-specific integrated circuits), logic circuits, gate arrays and the like.

As discussed in detail above, one of the most important activities humans do is to think about what they observe from their "sensors", and how they use that information in general to move on with their life. An important aspect of this is self-controlled sensing, the ability to move under own power and have the freedom to go where we want, do what we want when we get there, and see/hear what we want as sensory perception of our observations from a better observation point. This is the dynamic of human locomotion, and is fundamental to our thinking and our life's desires.

Humans move like a locomotive traction-engine pulls a train, by creating friction forces on the ground with our feet, because that is the only place we can change our mass location by exerting a force. But because we stand upright, we have to place our feet in front as steps, to move another point down the path of our intended direction, as mentally reaching forward. The connection between the human brain and our sensor perception for locomotion is one and the same: no sensing means no locomotion; no-locomotion means no-brain stimulation. We Locomote by falling down in the general direction we want to go, but in order to not end up on the ground, we place another foot in front to catch us; otherwise we would end up crawling. This is a rather crude method, but it works for every human body, and locomotion is guided by all the sensors as a unitary action. Our feet in bipedal walking or running locomotion, surprisingly are not very sensitive to what shoes we wear, because the body is so adaptable.

While human bio-mechanic models today are extremely complex, we are just beginning to understand and predict how we do it. It is well known that the human is self-synchronizing in a manner that the brain just guides the locomotion goals and the sensing make corrections and change local directions to our muscle memories. But the muscles also tell what is going on by the feedback pain of steps, and twisting and turning, stretching other body action that is perceived. This upper body dynamic throws the legs to where they need to be, as a corrected trajectory and not a rifle precision. Thus, errors in the brain appear as errors in locomotion and errors in the locomotion can appear as problems in the traction engine to create frictional forces.

Thus, the best way to understand locomotion is to measure how the forces on the ground that make the friction with the feet are created and changed. The example systems and methods described above measure the calf muscles which are a major contribution to the foot thrusts in locomotion. The precision of this locomotion is tied to the precise manner that the swing of the leg in planting the foot on the ground is where necessary precision is applied and corrected as needed.

The example systems and methods described herein enable the combining of MEMS 3D gravitational measurement (G) and magnetometer measurements (B), with pressure (P) measurements in spatiotemporal integrations for estimating action (A) and work (W) using event detections of peak Stance and valley Swing events, along with 'triangular' curve shape area estimation, scaled relative to "zero" P measurements, and estimating Balance and Track transitions on ground contact for $d\omega/dt=0$.

The example systems and methods also enable distinguishing between three modes of PST pressure sensing during locomotion based on feet touching the ground, namely, Two Feet, as an in stance on both feet (double limb support), and while extending a force moving to one foot, e.g., hitting a ball; One Foot, as a) the hitting impulsive action creates an unbalancing, reactive force, or b) when applying a pushing force, which is less impulsive in time, it creates a direction for continued force application, e.g., throwing a ball on one leg, or having contact with another large mass body; and Zero Feet, as in regaining balance on return to track of one or two feet that must dissipate or redistribute the angular momentum.

The example systems and methods also enable incorporating the modeling of locomotion, with the energy absorption and generation model, within the Action and Work efficiency metric under these three modes, whereby the transfer of angular momentum (ACM) changing Balance is correlated with the transfer of linear momentum (CM) changing Track such that these transfers use the PST identification time of maximum swing extension force (maximum centrifugal force), and these transfers use the PST identification time of the minimum stance foot-step force (trailing zero crossing from peak pressure).

The example systems and methods also enable periodic and aperiodic time boundary detection using HOS correlation on PST data.

The example systems and methods also enable combining the B&T and A&W computations in a PST sleeve localized manner, in order that the two paired PST parts can be reconstructed as a complete, correlative estimate (e.g., R-Thigh to L-Thigh, R-Calf to L-Calf, R-Thigh to R-Calf, L-Thigh to L-Calf, and further upper body limb intra-correlation pairing in a similar manner, inter-correlation pairing with lower body limbs, computations of symmetry, computations of efficiency, and computation of optimized locomotion for local visual, aural, or electrical stimulus feedback.

The example systems and method also enable combining multiple PST module measurements on the same limb sleeve to separate angular circumference contributions from local muscle pressure, as a further metric in muscle physiology for determining how the locomotion structures and effectors use energy as net cost of transport, defined as the energy needed to move a given Track distance, per unit body mass.

The example systems and methods also enable calibration of PST using a simple jump after attaching the sleeves to the limbs to start the system from a sleep mode, perform an alignment with the magnetic North and jump again, and then perform a 90° rotation to magnetic West, followed by the last jump before beginning movement. Here, the jump aligns the GRAV MEMS within all PST modules on all bands, and then the rotation does the same for the MAG MEMS, and finally the last jump is compared to the first in the PRES MEMS to calibrate all the sensors in relative location at three "step" in double support mode events, which are a signal to the processing to derive calibration parameters before processing data. These parameters are updated depending on the application, or stored and reused at the control of the user.

The example systems and method also enable integration in PST of force amplifier to FSR as a directly attached puck to resistive sensing material. This is used in combination with the built-in backing material of the sleeve and the buckle adjustment to achieve a comfortable and yet snug fit.

The example systems and methods also enable combining local PST PCB MEMSW gravitational measurements (G) and magnetometer (B) 3D vector measurements with pressure P, to estimate foot thrust force A, following the equations in the figures and the selected time constants for integration and lag defined by each.

The example systems and methods also enable combining B, G for paired thigh and calf PST sleeves to estimate a dynamic "Q-angle," defined over a gait period from stance into swing back to stance separately for each leg, as the 3D MAG location of each limb, with motion corrections.

The PST described herein provides application specifics for the data processing algorithms as typical constants:
1) Sensor type and placement.
2) Information extraction details; algorithms, processing, time scales, spatial integrations, data flow parameters for change-detection algorithms.
3) Information display and database organization and analysis tailored for each application.
4) Computing of correlation in sensor dynamics with both second-order and fourth-order (in excess as a higher-ordered statistic, HOS). These are used in:
   Additional modeling of combined limb correlations used in algorithms defined by second order:
      i. calves/thighs, forearm/biceps,
      ii. shoulder-(collar-bone (clavicle), humerus (the upper arm bone), and scapula (shoulder blade), rotary cuff joint)
      iii. pelvis-(hip-bone (coxal-bone), sacroiliac-joint, sacral-sromontory; hip joint)
   Additional modeling of combined limb correlations used in algorithms defined by fourth order:
      i. upper-body/lower-body,
      ii. twisting-spine (ACM) foot-placement (CM)
      iii. joint centered motion in elbow/knee, shoulder/hips.
5) Gait applications in physical therapy, with the addition of the swing measurement and L-R leg correlation analysis from using PST metrics.
6) ACL injury in preventive medicine applications and training for predisposition to injury, using PST metrics.
7) Sports training and equipment development applications, using PST metrics.
8) Pre-/post-operative diagnosis, treatment, and recovery assessment, using PST metrics.
9) Mental impairment applications (stroke, Alzheimer's, brain damage), using PST metrics.
10) Elderly and aging applications (foot drop, feet stuck to floor, unbalance, and asymmetric gait), using PST metrics.

Thus, the technology described herein can provide enhanced sports performance coupled with injury avoidance as continuous, two-beat gait information from paired leg measurements. For example, as described herein, PST provides paired sensors in sleeves on lower body calves. Calf sensors with local feedback can, for example, coordinate a runner's stride to have an efficient pace and warn of potential weakening that could lead to injury. In addition, the technology described herein can provide for new measurements such as precise proprioception muscle action measurements. Such measurements can be used, for example, to evaluate central nervous system disorders.

The technology described herein can be widely utilized by professionals and amateurs in sports training and risk assessment including racing, jumping, hiking; team and individual sports including, but not limited to, basketball, baseball, lacrosse, hockey, soccer, tri-athletics, golf, tennis, football, and the like, at all levels (e.g., high school, college, professional, recreational) and including all styles (e.g., bike, skateboard, ski, run, swim, barefoot).

The technology described herein is also useful for practitioners in orthopedic ACL surgery, diagnosis, rehabilitation, and recovery, as well as researchers in locomotion and gait analysis, health care workers, medical elderly care professionals. The technology can also be used in central nervous system (CNS) diagnosis, monitoring, and treatment of conditions including, but not limited to, dementia, fall down, stroke, spine, lower back, Alzheimer's disease and the like.

In the past, locomotion analysis used photographs, force plates, shoe pads and video to collect data to review and understand how people move. This is technologically equivalent to filming a car's tires to determine where it is going. The technology described herein provides on-board internal locomotion sensing that is fast, inexpensive, provides real-time feedback, can be used outdoors, and measures both stance ground reaction force (GRF) and swing phase (free leg motion) without cameras.

Figure 26:
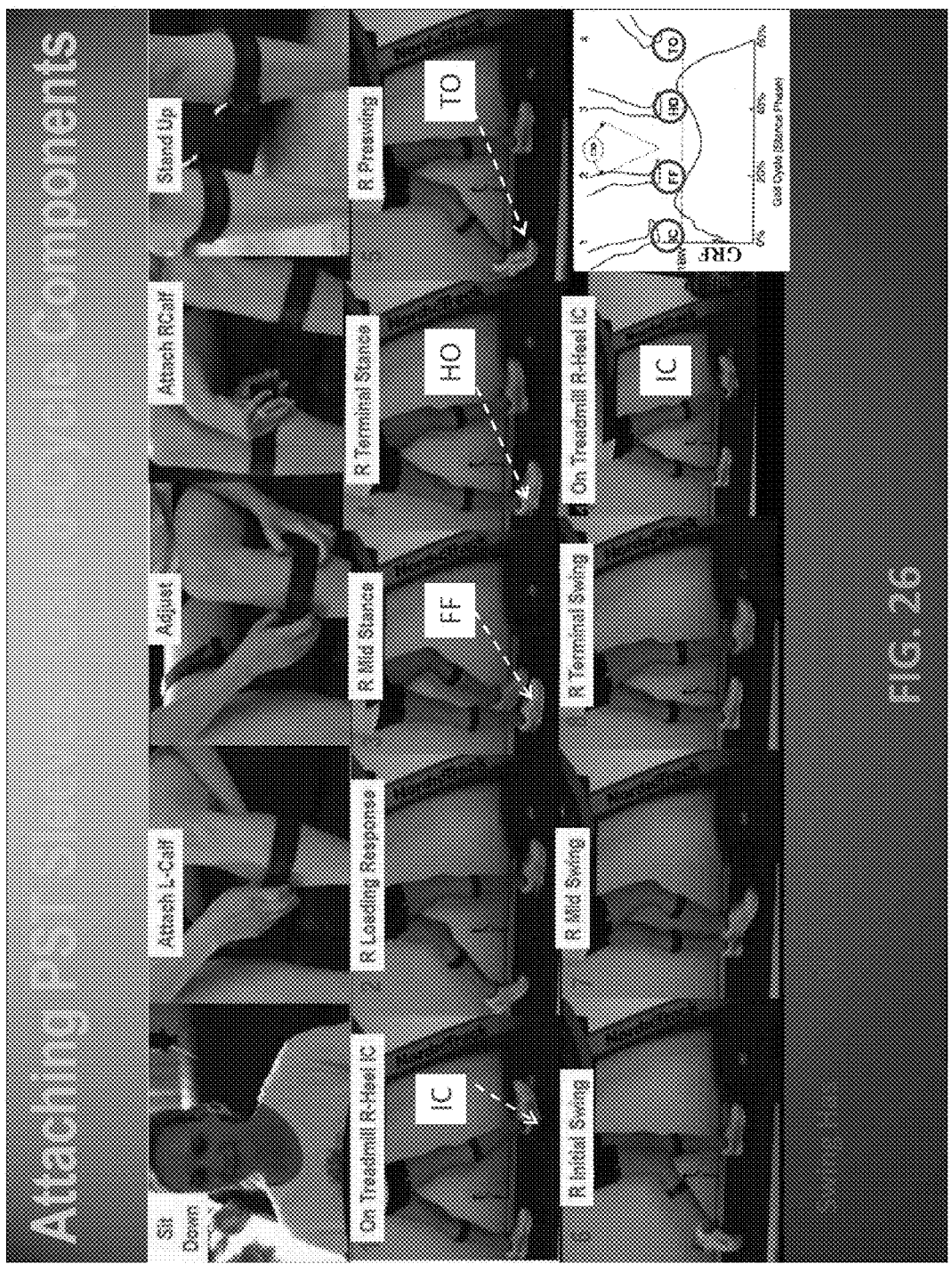
FIG. 26 shows eight cycle components of gait.

With reference to FIG. 26, stance only measures four gait parts of Initial Contact (IC), Flat (full) Foot (FF), Heel Off (HO) and Toe Off (TO). The technology described herein provides measurements that enable an understanding of how people move with continuous swing phase from stance phase as a single stride evaluation. The technology measures continued muscle contraction after TO, and proprioception feedback correction before Swing Reversal Transition (SwRT) before IC.

With reference to FIG. 24, the technology described herein provides unique measurement of swinging leg motion, measuring muscle and brain activity and connects to existing network/readout devices to provide informative health metrics. An example implementation includes RF-linked sensors placed on belt and the sensor count may vary depending on the application from amateur sport to orthopedic diagnostics and physical therapy. Product categories include sports, ACL injury PT-treatment, elderly, 'game exercise', navigation and the marketplace application corresponds to a software modification relating to the number of sensors and readout information. The technology utilizes correlation between pairs of sleeves attached to thighs, calves, forearm and/or biceps and watch/laptop RF connectivity, for example, may provide connection by telecom to cloud computing, server historic analysis, database mining, pre/post op medical comparison, trainer monitoring of team players and the like.

The technology described herein uses a model to interpret the measurements and provide user feedback in real time. The model incorporates correlation analysis between paired limbs using an RF link (e.g., computation may occur in a watch or cell phone or other computer device). The technology can tie all data to a singular event in stride for each limb, being the SwRT (TSwR) "tick" to relate all stride data in an absolute time reference. The technology uses physically modeled Action and Work to estimate efficiency and incorporates estimates of upper body balance as the difference in summed 3D vectors for each leg in 3D gravity (G), to that of the estimated 3D leg thrust force (A) using a calibrated sleeve contraction/expansion as amplitude and the vector angle from a calibrated magnetic leg shank angle.

Figure 27:
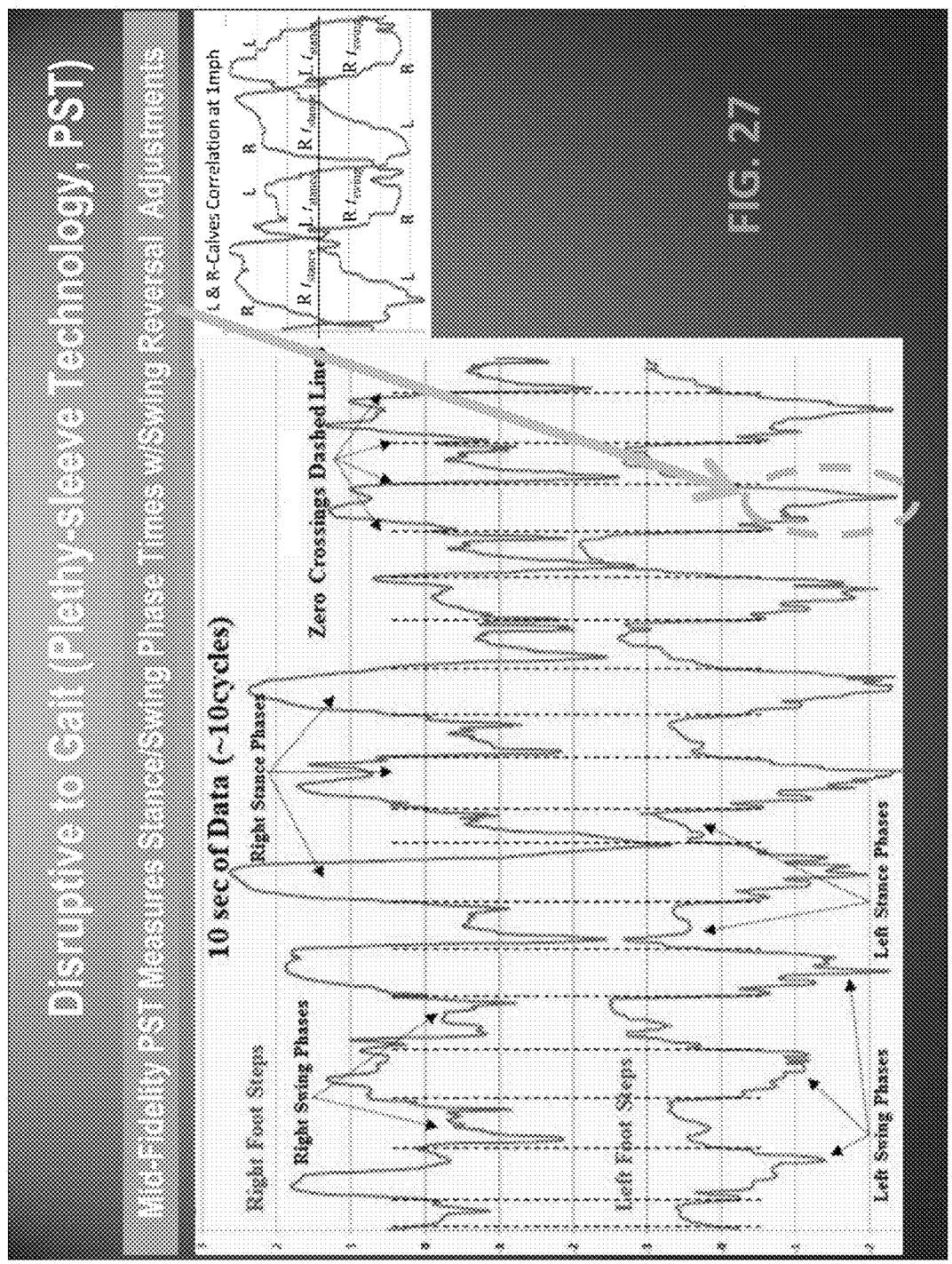
FIG. 27 shows example mid-fidelity PST measurements of stance/swing phase reversal adjustments.

With reference to FIG. 27, both left/right calf data shows correlation of stance synchronization transfer and SwRT valleys in half-stride period synch, with zero-crossings of data marked with dashed line. Mid-fidelity PST measures stance/swing phase with times with swing reversal adjustments (indicated in dashed ellipse) of minimum data valley, and proceeded with a bump corresponding to the proprioception feedback adjustment.

Figure 28:
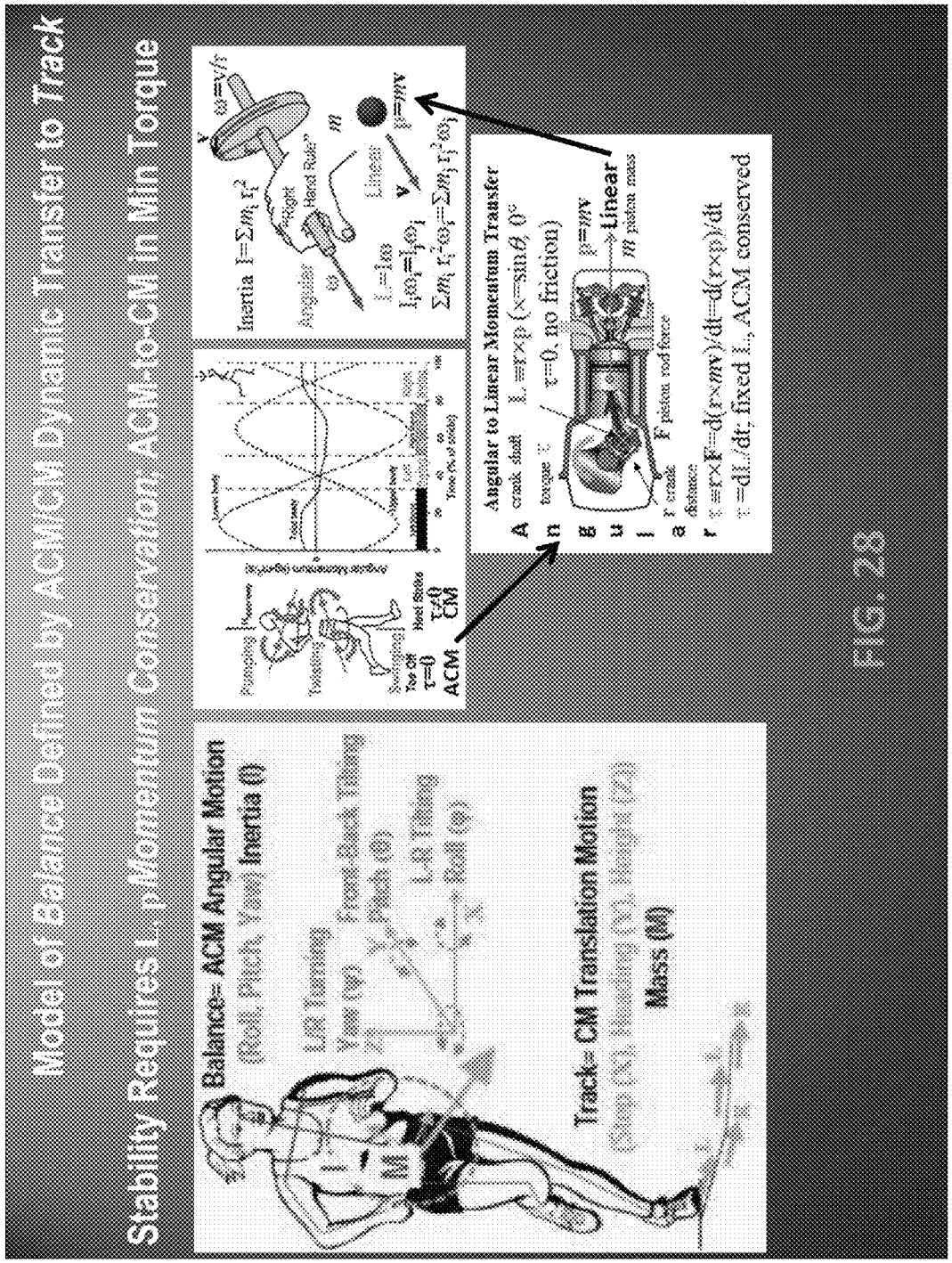
FIG. 28 shows an example model of balance.

As summarized in FIG. 28, the model uses an about center of mass dynamic (ACM) from angular momentum of twisting spine moving upper body shoulders to swing arms to 'pump' lower body pelvis to swing thighs, translating the swinging momentum to a linear momentum for the center of mass (CM) forward motion with a track of footsteps with minimum friction (e.g., as in a piston linear thrust transfer from a cam rotation) to minimize side friction forces and maximizes forward locomotion forces.

With reference to FIG. 14, further examples of left/right stance transfer and swing dynamics show correlated SwRT with proprioception that changes in stride time period between walking and running, accompanied with a different foot thrust force shown with running (as well known), but the detail shows muscle changes during the stride to be used in Balance and Track computations, noted by peak stance amplitudes, and minimum swing amplitudes (valleys).

Figure 29:
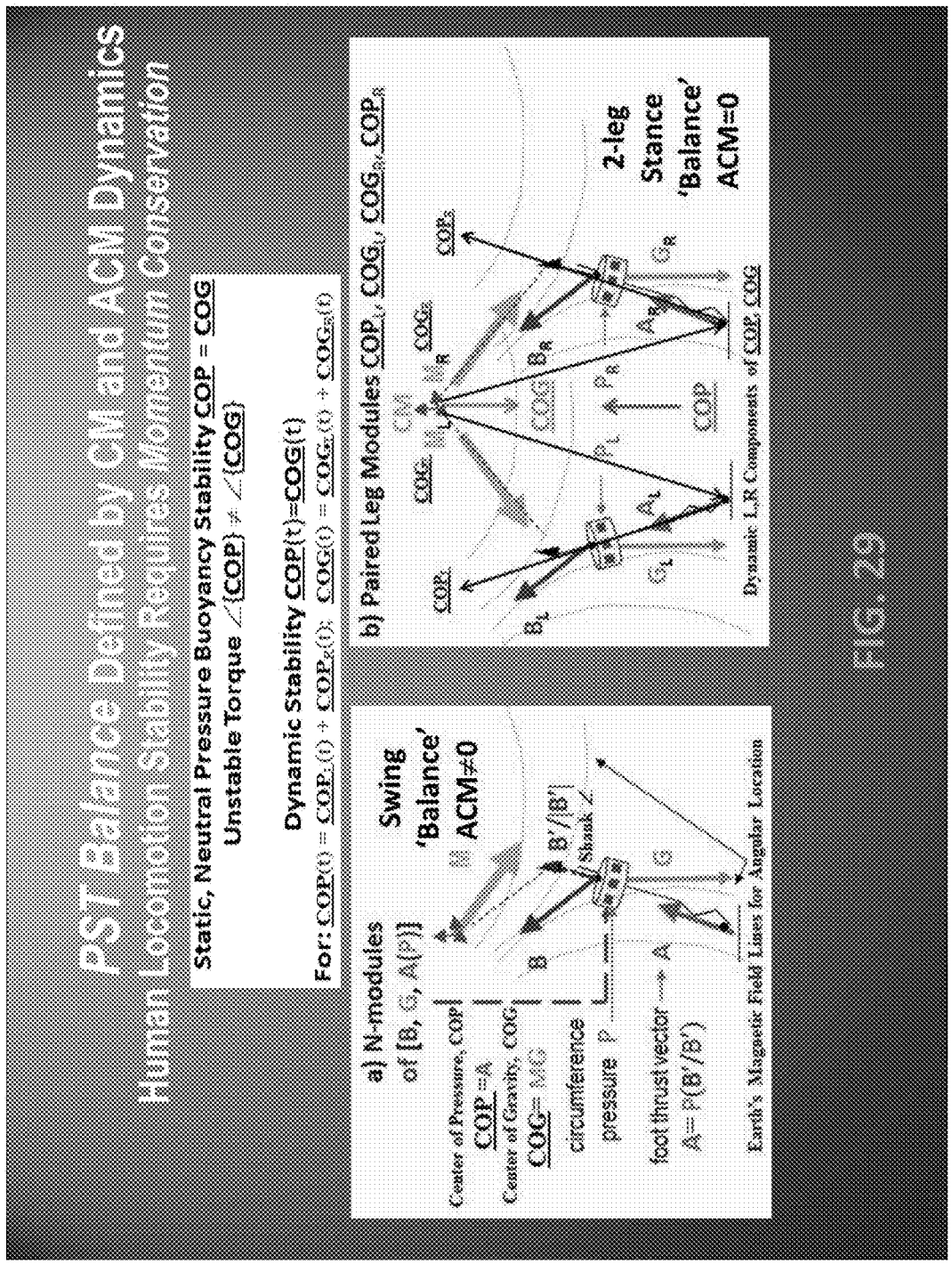
FIG. 29 shows balance defined by CM and ACM dynamics.

With reference to FIG. 29, vector force equations as G and A differences show the estimation of a single sleeve on the left, balancing on one leg in the swing mode, where the ACM is creating an angular momentum for balance, and with sleeves on each calf on the right in a double stance mode, which is only 20% of the time. The equations show that the Center of Pressure (COP) for both L-left, R-right legs (COPL, COPR) dynamically in time (t) balance the Center of Gravity (COGL, COGR), to continuously maintain balance for COP=COG. This is a dynamic stability between the forces and the angles of the body, which includes the balance of the angular momentum of ACM switching between the swing and the linear momentum CM establishing a stance balance.

Figure 30:
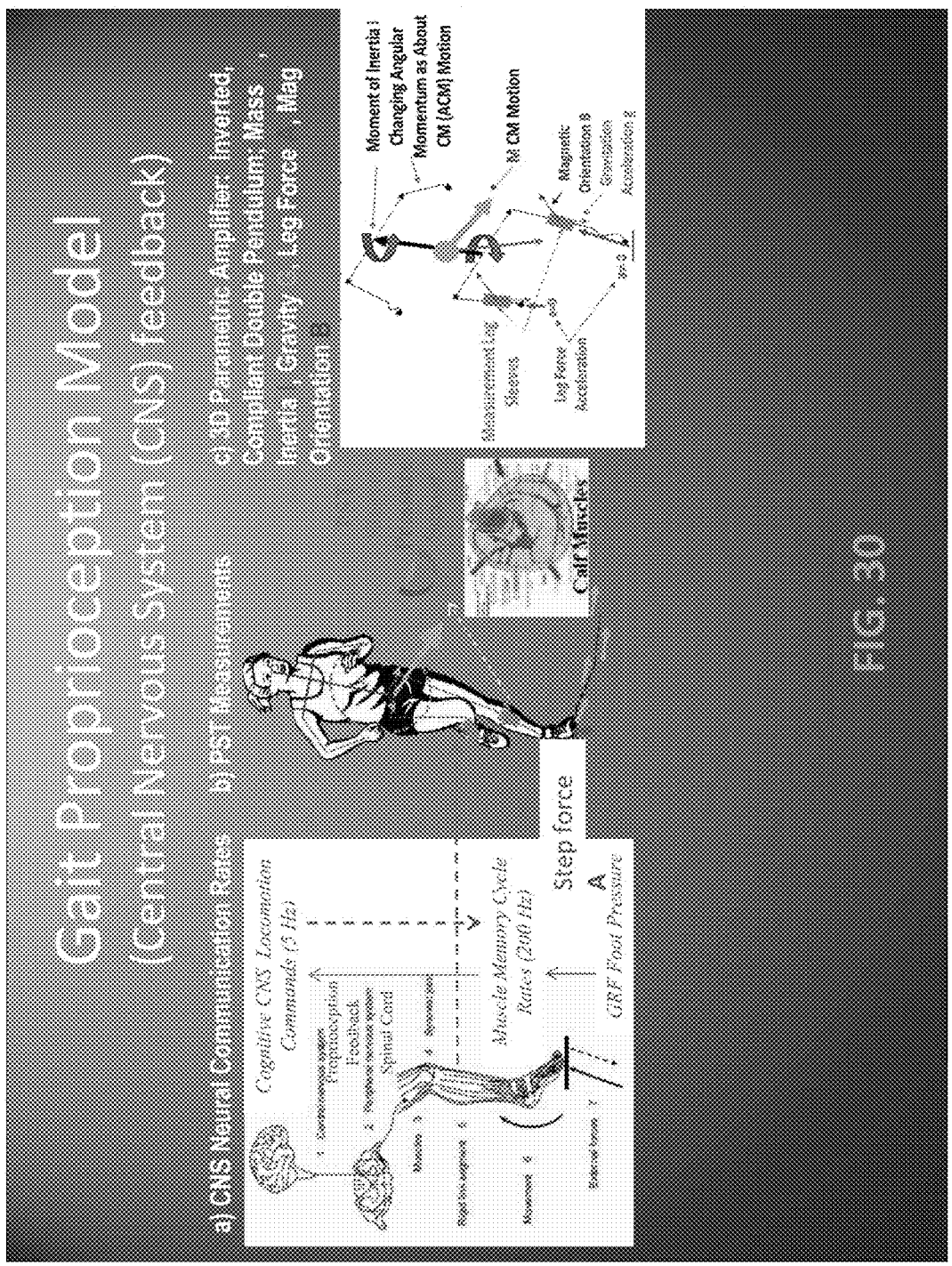
FIG. 30 illustrates an example gait proprioception model.

With reference to FIG. 30, proprioception is a feedback from the limb position and speed dynamics up the spine to the brain, used in corrections controlling the locomotion dynamics just before the SwRT point valley, as a small peak 'bump' as an expansion in the sleeve pressure, where this balance is a parametric amplifier synchronization of the upper body and lower body pumping, which is seen in the sleeve data.

Figure 31:
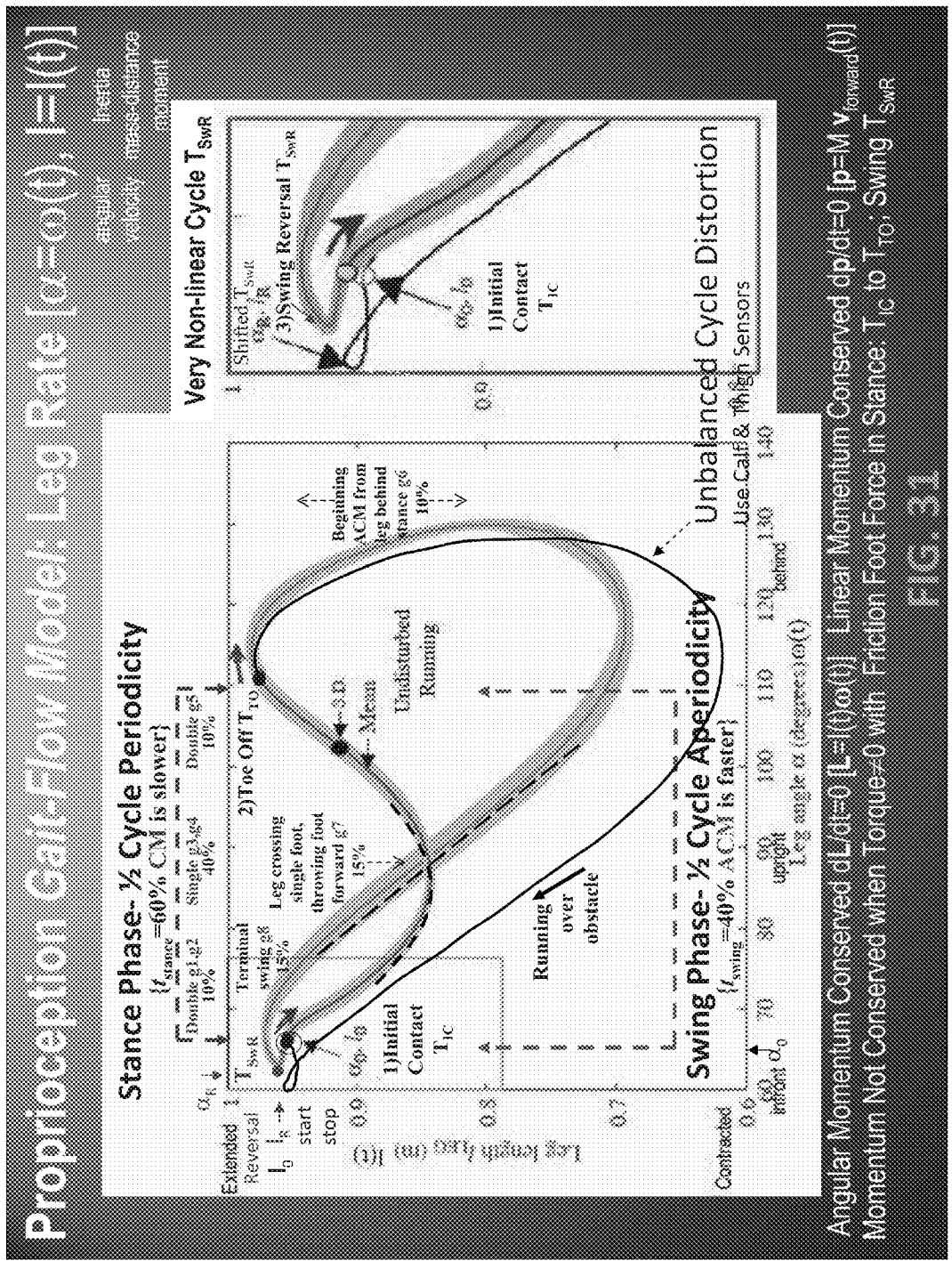
FIG. 31 illustrates a proprioception gait flow model.

With reference to FIG. 31, the model uses a graphic dynamic to determine balance and track in another way, where the horizontal axis is the leg angle from the hip to the toe, and the vertical axis is the Leg angle being upright at 90 degrees. The eight (8) phases of the gait stride cycle are also indicated for one leg, and an example of distorted dynamics is shown in the thin line, particularly in the upper left corner of the plot, just before the IC part of the cycle, here with conservation of angular momentum (L) defined in this model as a torque free (no friction) period in time (t) as (dL/dt=0). Any deviation here is a reduction in efficiency, so this data derived from the sleeve measurements is another means of developing metrics of efficiency in momentum transfer from linear thrust forward to angular rotation in swinging the leg.

Figure 32:
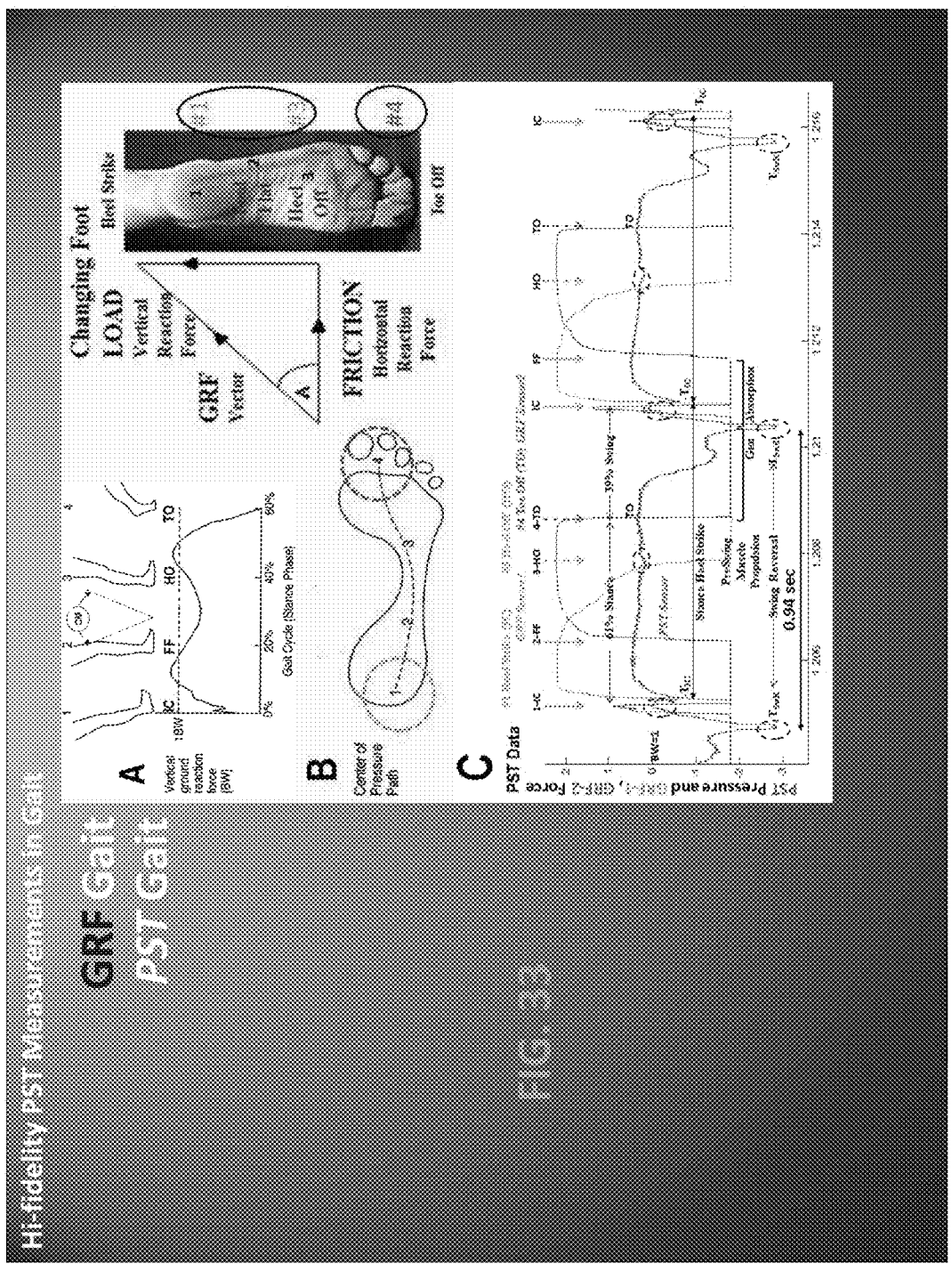
FIG. 32 shows details of proprioception muscles involved in locomotion.

FIG. 32 provides details of the proprioception muscles involved in locomotion, showing that a major part of these dynamics are part of the PST metrics in CM changes and calf muscle stretch.

Figure 33:
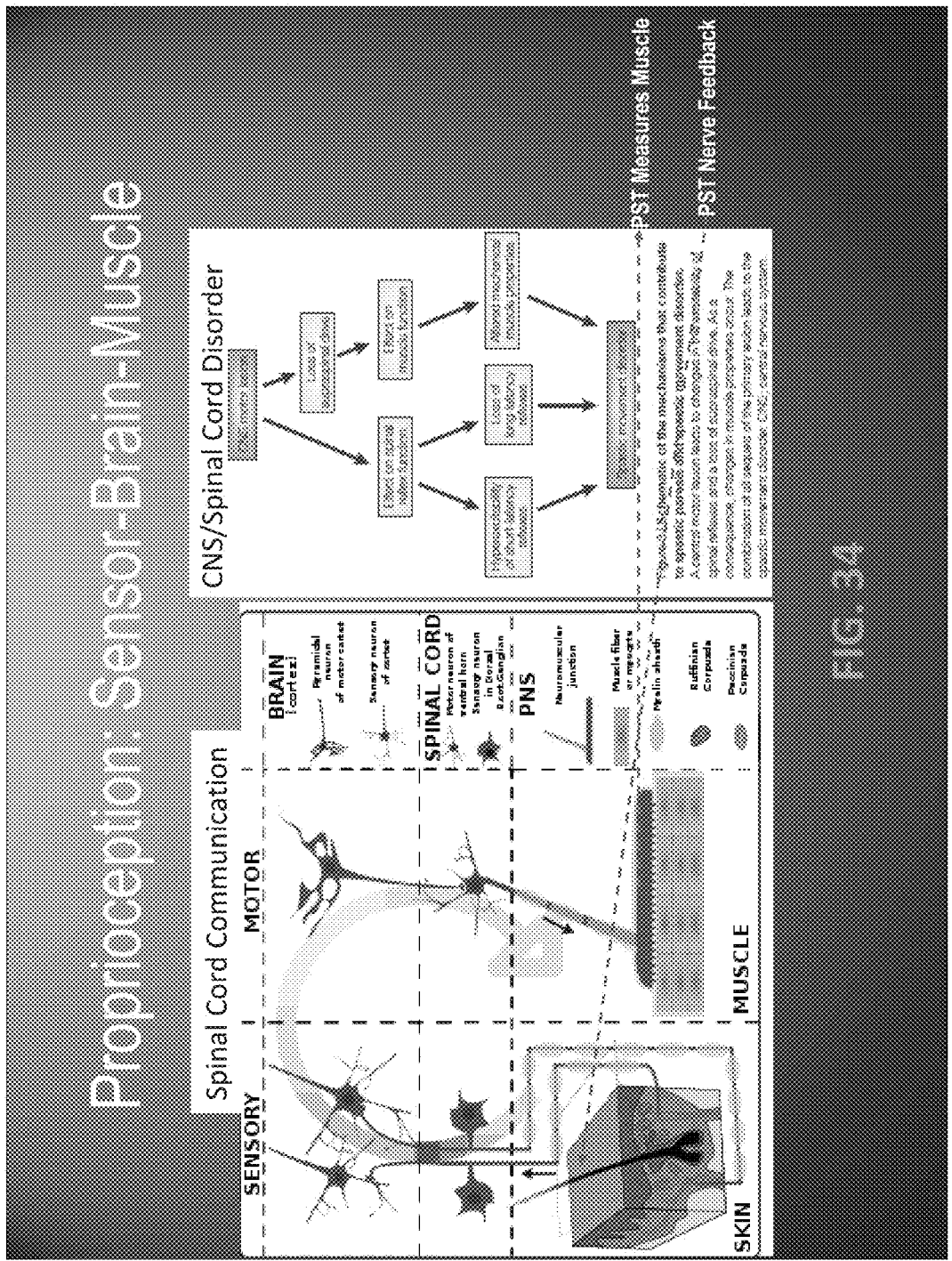
FIGS. 33a, 33b and 33c show example PST measurements in gait.

With reference to FIG. 33, using a force sensor placed in a runner's shoe at the heel and toe, data is collected to show the precise measurement with the sleeve data, of when the A force of COP is applied, without using a force plate and treadmill. The four stance phases of the gait cycle are accurately indicated, and the extended pressure shown during swing, just after TO is the retained muscle contraction of the sleeve data for having a better inertia to swing the leg forward at a faster manner; this detail is so quick that it is not observed in the camera dynamics used by gait labs and is a unique discovery. The proprioception bump is clearly shown for three steps, and this precision is combined with adjustments in SwRT to have an almost zero angular momentum at IC when the foot returns to the ground as the next IC step. The pressure sensor on the foot is shown in the blue/green positions and the sleeve data is in red.

Figure 34:
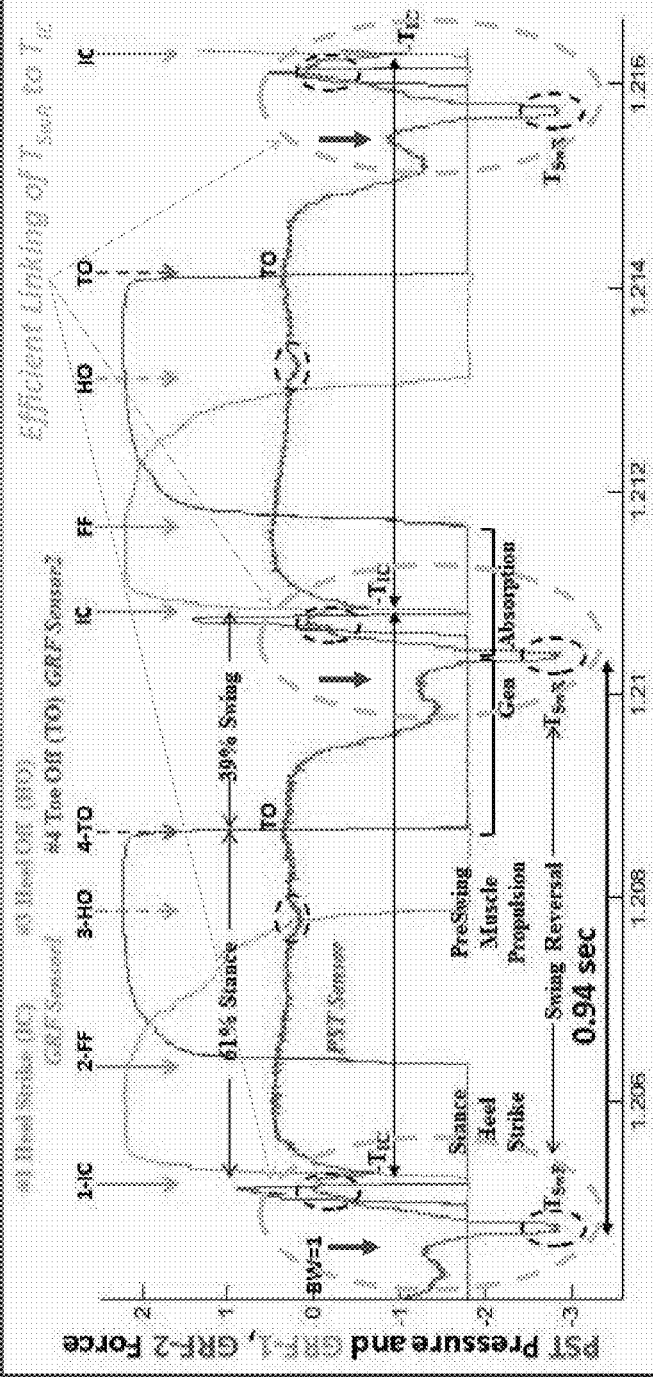
FIG. 34 shows details proprioception modeling.

FIG. 34 shows details of the proprioception modeling indicating how the PST sleeve can be part of detecting errors in this feedback from diseases of the spine and brain disorders, sensory receptors, peripheral nerves, dorsal roots, and central nervous system pathways, which can incorporate a feedback shown to the nerves in the skin for signaling the brain to improve gait disorders.

FIG. 8 shows the specific muscles being measured in comparison with the nonlinear aspects with a model of the gait being dominated by the rectus muscles during the unique swing phase measurements, and how this dynamic is tied specifically to the energy absorption and generation about the SwR Time (number 4 shown with an arrow).

Figure 35:
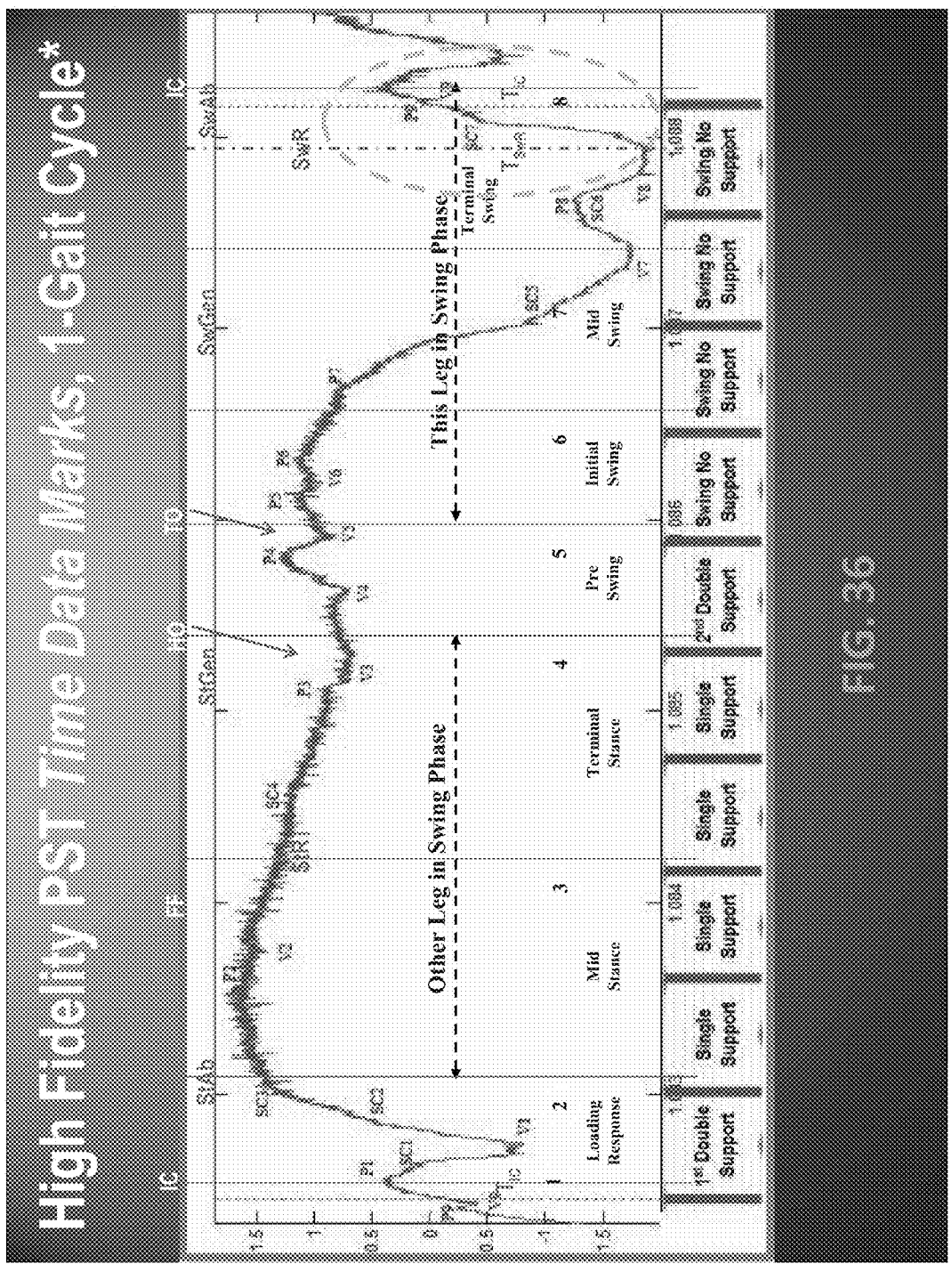
FIG. 35 shows an example high fidelity PST with ground reaction force over two gait cycles.

In FIG. 35, the relationship between the SwR time (TSwR) and the IC time (TIC), bounding the detailed part of the whole gait cycle, where the momentum transfer must be conserved during the short time the foot touches the ground (less than 10 msec), with the whole event being captured with a total time of 20 msec, as a useful metric for each step making a Track of foot paths.

In FIG. 36, the same full cycle is shown with a very precise marking of the events during the cycle, of linear slope changes (SC) peaks (P) and valleys (V), comprising 25 events to characterize the stride within the absolute time of the SwRT. Energy absorption (Ab) and generation (Gen) are also indicated along with the typical eight (8) parts of the 1-sec cycle (shown with vertical marks at 0.1 sec), with a fidelity of individual muscle changes on the order of full-width peak and valley of only 30 msec, and slope changes in under 10 msec, as a series of reproducible data every second with a fidelity of below 1%.

In FIG. 37, both thigh and calf bands are shown to indicate how both muscles show the thigh-lifting (T) as a peak and the calf (C) swinging as a valley phase in/out of synch (for L/R sides, and C/T sleeves).

FIG. 38 shows a similar set of data as in FIG. 37, but here all sixteen (16) sensors are used, with a very precise timing of the four muscle measurements on the 4 limb locations demonstrating a self-synchronization in the gait cycles.

FIGS. 22(a) and 22(b) show a detail of the gait cycles shown over 100 strides shown various scales of variations in trends in the IC location amplitude, and the peak stance pressure and valley swing extension. This is useful data to archive for use in monitoring patients.

FIG. 39 shows PST data event time scales, with short events becoming scaled to be part of a larger trend, from 10 msec to 5 sec to 5 min.

FIG. 19 shows a categorization of data scales using the data analysis of earlier figures, but here being "rolled" up in the analysis for decade scales of various cycles shown in red, to trend analysis output from muscle to Track and Balance to Training in Action & Work Efficiency, and Cognition in Symmetry & Efficiency, as well as the longest scale is for observing Aging.

Figure 40:
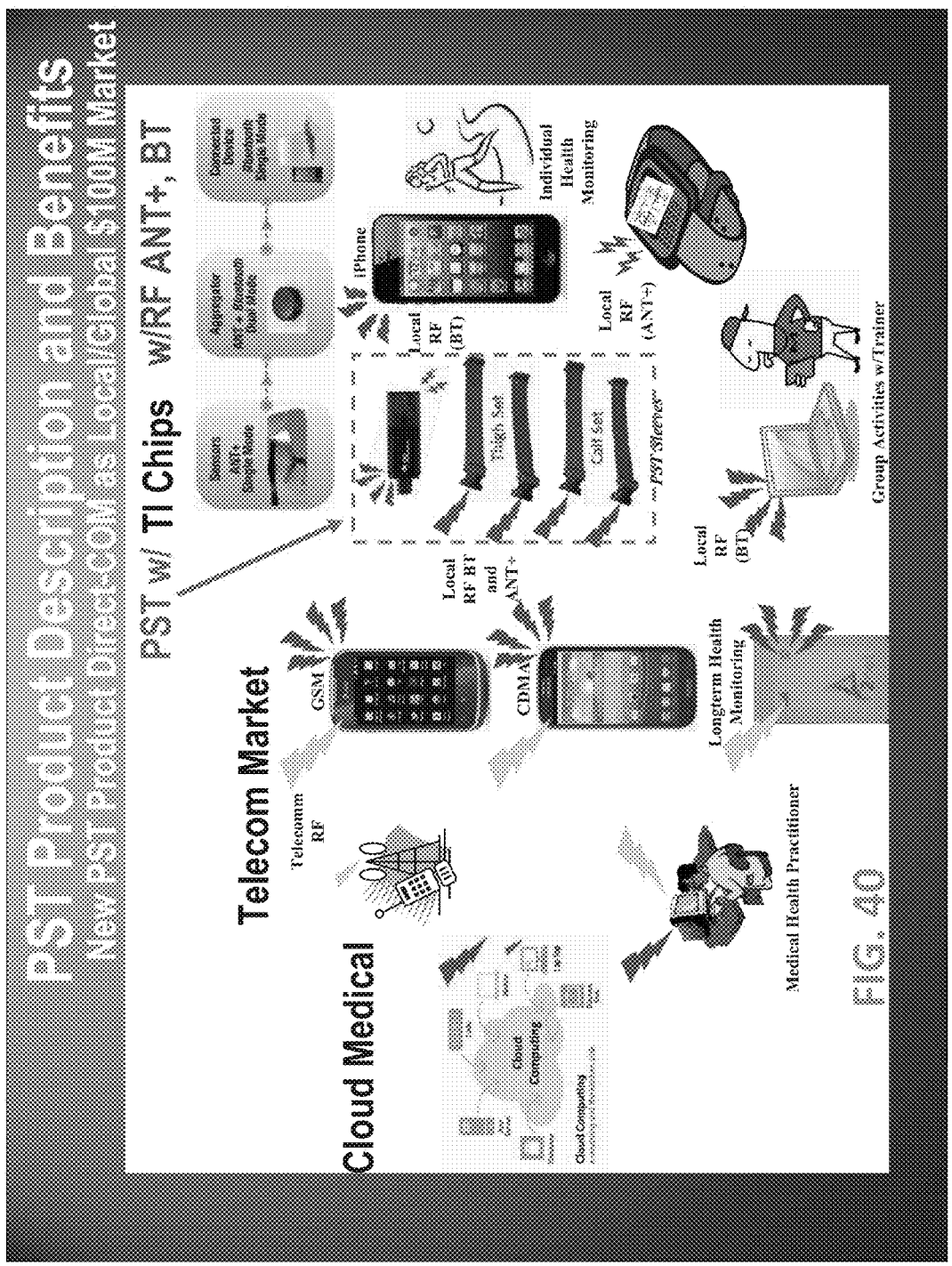
FIG. 40 shows an example arrangement of a PST system.

FIG. 40 shows a means of transmitting the data stream of the measurements using a Bluetooth RF link to a gate way to the telecom, such as from a cell phone, and on into the cloud, where the data is placed on a server for the medical and sports professionals can analyze the results across historical trend and population or team trends.

FIG. 41 shows an example device package as a standalone device, to be placed inside a sock or on a sleeve band for multiple calf measurements or just one, where the unit is battery powered using an inductive charging and also has onboard processing, such that the correlation of the paired sleeves involves just comparing the peaks, slopes and valleys for correlation.

FIGS. 2 and 18(*a*) and 18(*b*) highlight various unique aspects as a product of strap-on sleeves to monitor calf muscles for:

a. correlating left-right leg gait stance & swing phases
b. ANT+ to watch to display information
c. information provides real-time, graphic user feedback
d. corrections to run faster with less injury
e. health improvement in efficiency and symmetric balance
f. precursors to potential injury prevention FIG. 42 shows the unit data analysis with RF connectivity, set up for variable integration and analysis time scales, between two sleeves and between the watch or cell phone into a longer RF telecom connectivity.

FIG. 43 show an example of unit data analysis with parametric control of the processing for many time scales with connectivity for an eight-unit calf correlation example.

The systems and methods described herein are described in connection with certain non-limiting example embodiments. The following claims are not limited to these example embodiments, but on the contrary, are intended to cover various modifications and equivalent arrangements.

I claim:

1. A system comprising:
one or more sleeves, each configured for attachment to a leg and comprising a pressure sensor, an accelerometer and a magnetometer;
a processor for processing sensor signals from the pressure sensor, the accelerometer and the magnetometer to estimate action (A) and work (W) using event detections of peak stance and valley swing events associated with leg movement, wherein the processor detects small changes during swing from brain feedback of proprioception sensing of the lower body component locations and movement dynamics to adjust the swing reversal behavior with feedback for a minimum off-unbalance and use of friction in stepping forward with each stance step.

2. The system according to claim 1, wherein each sleeve comprises a board to which the pressure sensor, the accelerometer and the magnetometer are affixed.

3. The system according to claim 2, wherein the magnetometer and accelerometer are affixed to a first side of the board and the pressure sensor is affixed to a second, opposite side of the board.

4. The system according to claim 1, wherein each sleeve further comprises a wireless module for communication with the processor.

5. The system according to claim 1, wherein the processor detects small changes in the muscle contractions and expansions in conjunction with leg orientation to the ground, which are used to automatically assess locomotion efficiency and abnormal or disordered behavior.

* * * * *